(12) United States Patent
Miyashita et al.

(10) Patent No.: US 12,286,444 B2
(45) Date of Patent: Apr. 29, 2025

(54) ORGANIC COMPOUND AND ORGANIC LIGHT-EMITTING DEVICE

(71) Applicant: CANON KABUSHIKI KAISHA, Tokyo (JP)

(72) Inventors: Hirokazu Miyashita, Kanagawa (JP); Naoki Yamada, Tokyo (JP); Yosuke Nishide, Kanagawa (JP); Jun Kamatani, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 795 days.

(21) Appl. No.: 17/517,194

(22) Filed: Nov. 2, 2021

(65) Prior Publication Data
US 2022/0135595 A1    May 5, 2022

(30) Foreign Application Priority Data

Nov. 2, 2020  (JP) .................................. 2020-183750

(51) Int. Cl.
| | |
|---|---|
| *C07D 519/00* | (2006.01) |
| *H10K 85/60* | (2023.01) |
| *H10K 50/11* | (2023.01) |
| *H10K 101/10* | (2023.01) |
| *H10K 101/30* | (2023.01) |
| *H10K 101/40* | (2023.01) |

(52) U.S. Cl.
CPC ......... *C07D 519/00* (2013.01); *H10K 85/636* (2023.02); *H10K 85/6572* (2023.02); *H10K 85/6574* (2023.02); *H10K 85/6576* (2023.02); *H10K 50/11* (2023.02); *H10K 2101/10* (2023.02); *H10K 2101/30* (2023.02); *H10K 2101/40* (2023.02)

(58) Field of Classification Search
None
See application file for complete search history.

(56) References Cited

U.S. PATENT DOCUMENTS 9,269,911 B2 * 2/2016 Horiuchi ............ H10K 85/6576

FOREIGN PATENT DOCUMENTS

| CN | 110642732 A | * | 1/2020 | ............ C07C 225/22 |
| CN | 113004298 A | * | 6/2021 | ............ C07D 405/04 |
| WO | WO-2020057480 A1 | * | 3/2020 | ............ C07D 493/04 |

OTHER PUBLICATIONS

Machine translation of CN-113004298-A, translation generated Aug. 2024, 9 pages. (Year: 2024).*
Kamel, M., et al., "Synthesis of some Dinaphthoxanthones, Benzonaphtoxanthones and Benxofuroxanthones", Egypt. J. Chem., 1973. pp 91-100, vol. 16, No. 2.

* cited by examiner

*Primary Examiner* — Robert S Loewe
(74) *Attorney, Agent, or Firm* — Canon U.S.A., Inc. I.P. Division

(57) ABSTRACT

An organic compound represented by formula [1] or [2]:

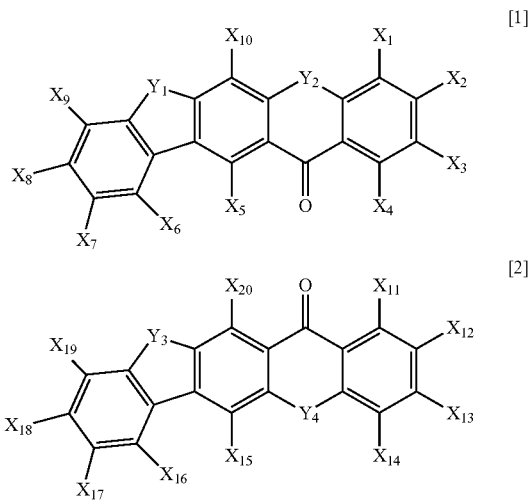

where $X_1$ to $X_{20}$ are each independently selected from a hydrogen atom, a halogen atom, and alkyl, alkoxy, amino, aromatic hydrocarbon, heterocyclic, aryloxy, heteroaryloxy, silyl, and cyano groups, in which at least one of $X_1$ to $X_{10}$ and at least one of $X_{11}$ to $X_{20}$ are each an amino group or a group containing an amino group; $Y_1$ and $Y_3$ are each oxygen, sulfur, selenium, tellurium, a carbonyl group, or a $CR_1R_2$ group and are optionally the same or different, in which $R_1$ and $R_2$ are each independently selected from a hydrogen atom, a halogen atom, and alkyl, alkoxy, amino, aromatic hydrocarbon, heterocyclic, aryloxy, heteroaryloxy, silyl, and cyano groups, and $Y_2$ and $Y_4$ are each oxygen, sulfur, selenium, or tellurium and are optionally the same or different.

20 Claims, 10 Drawing Sheets

FIG. 1

| COMPOUND | STRUCTURE | HOMO DISTRIBUTION | LUMO DISTRIBUTION | ENERGY DIFFERENCE BETWEEN $S_1$ AND $T_1$ (eV) |
|---|---|---|---|---|
| EXEMPLIFIED COMPOUND B-1 | 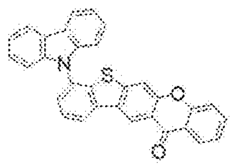 | | | 0.26 |
| EXEMPLIFIED COMPOUND B-2 | 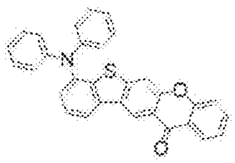 | | | 0.15 |
| EXEMPLIFIED COMPOUND B-3 | 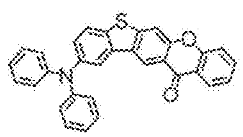 | | | 0.15 |
| EXEMPLIFIED COMPOUND B-4 | 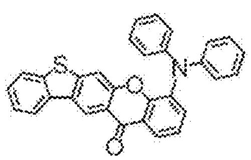 | | | 0.32 |
| EXEMPLIFIED COMPOUND B-5 | 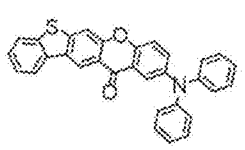 | | | 0.32 |
| EXEMPLIFIED COMPOUND C-1 | 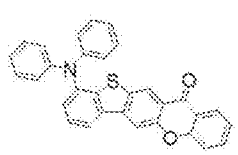 | | | 0.25 |
| EXEMPLIFIED COMPOUND D-1 | 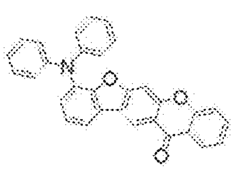 | | | 0.19 |
| COMPARATIVE COMPOUND 1 | 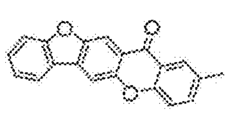 | | | 0.72 |

FIG. 2

| COMPOUND | STRUCTURE | DIRECTION PERPENDICULAR TO MOLECULAR PLANE | DIRECTION OF MOLECULAR PLANE | MOLECULAR ASPECT RATIO |
|---|---|---|---|---|
| EXEMPLIFIED COMPOUND B-1 | 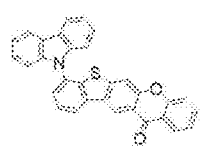 | | | 1.8 |
| EXEMPLIFIED COMPOUND D-1 | 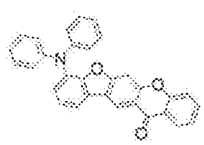 | | | 1.7 |
| EXEMPLIFIED COMPOUND B-26 | 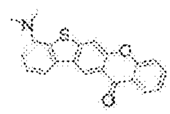 | | | 4.0 |
| COMPARATIVE COMPOUND 1 | 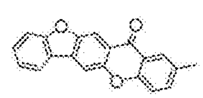 | | | 8.3 |

FIG. 3

| COMPOUND | STRUCTURE | MOLECULAR WEIGHT | DIRECTION OF MOLECULAR PLANE | MOLECULAR ASPECT RATIO |
|---|---|---|---|---|
| EXEMPLIFIED COMPOUND D-5 | 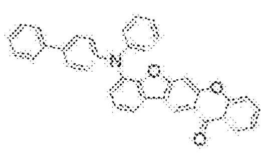 | 529.60 | | 1.6 |
| EXEMPLIFIED COMPOUND D-6 | 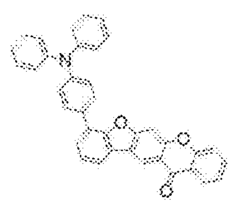 | 529.60 | | 2.4 |

ORGANIC COMPOUND AND ORGANIC LIGHT-EMITTING DEVICE

BACKGROUND OF THE INVENTION

Field of the Invention

The present disclosure relates to an organic compound and an organic light-emitting device.

Description of the Related Art

Organic light-emitting devices (hereinafter, also referred to as "organic electroluminescent devices" or "organic EL devices") are electronic devices each including a pair of electrodes and an organic compound layer disposed between these electrodes. Recently, organic light-emitting devices have made remarkable progress and have achieved low-driving voltage, various emission wavelengths, and fast response time. The use thereof has enabled the development of thinner and lighter light-emitting apparatuses. Regarding the improvement of the efficiency of light-emitting devices, devices containing high-efficiency materials, such as phosphorescent materials and delayed fluorescent materials, have been reported. Egyptian Journal of Chemistry (1973), 16(2), 91-100 (Non-Patent Literature 1) describes compound A-1 below.

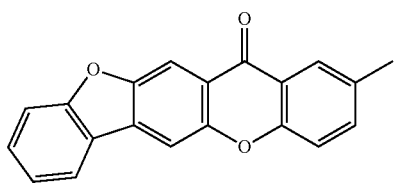

A-1

When compound A-1 described in Non-Patent Literature 1 is used for light-emitting layers of organic light-emitting devices, there is a disadvantage with luminous efficiency.

SUMMARY OF THE INVENTION

The present disclosure has been accomplished in light of the foregoing disadvantage. The present disclosure provides an organic compound and an organic light-emitting device that have excellent luminous efficiency. The present disclosure also provides an organic light-emitting device excellent in driving durability characteristics. According to one aspect of the present disclosure, there is provided an organic compound represented by formula [1] or [2]:

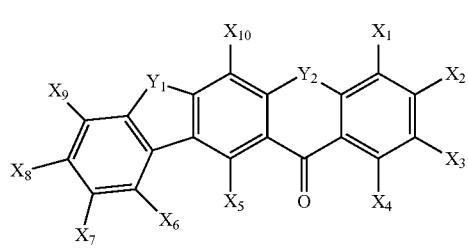

[1]

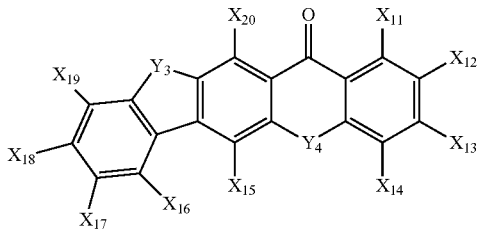

[2]

where in formula [1] or [2], $X_1$ to $X_{20}$ are each independently selected from a hydrogen atom, a halogen atom, a substituted or unsubstituted alkyl group, a substituted or unsubstituted alkoxy group, a substituted or unsubstituted amino group, a substituted or unsubstituted aromatic hydrocarbon group, a substituted or unsubstituted heterocyclic group, a substituted or unsubstituted aryloxy group, a substituted or unsubstituted heteroaryloxy group, a silyl group, and a cyano group, in which at least one of $X_1$ to $X_{10}$ and at least one of $X_{11}$ to $X_{20}$ are substituted or unsubstituted amino groups or are groups containing substituted or unsubstituted amino groups, and groups bonded to nitrogen atoms of the substituted or unsubstituted amino groups are optionally taken together to form a ring structure; $Y_1$ and $Y_3$ are each oxygen, sulfur, selenium, tellurium, a carbonyl group, or a $CR_1R_2$ group and are optionally the same or different, in which $R_1$ and $R_2$ are each independently selected from a hydrogen atom, a halogen atom, a substituted or unsubstituted alkyl group, a substituted or unsubstituted alkoxy group, a substituted or unsubstituted amino group, a substituted or unsubstituted aromatic hydrocarbon group, a substituted or unsubstituted heterocyclic group, a substituted or unsubstituted aryloxy group, a substituted or unsubstituted heteroaryloxy group, a silyl group, and a cyano group; and $Y_2$ and $Y_4$ are each oxygen, sulfur, selenium, or tellurium and are optionally the same or different.

Further features of the present disclosure will become apparent from the following description of exemplary embodiments with reference to the attached drawings.

BRIEF DESCRIPTION OF THE DRAWINGS

FIG. 1 is an energy difference between $S_1$ energy and $T_1$ energy of exemplified compounds, and HOMO distribution and LUMO distribution of the exemplified compounds.

FIG. 2 is molecular aspect ratios, and molecular models at a molecular plane direction and at a direction perpendicular to the molecular plane direction.

FIG. 3 is molecular aspect ratios, and molecular models at a molecular plane direction.

DESCRIPTION OF THE EMBODIMENTS

Organic Compound

Figure 4:
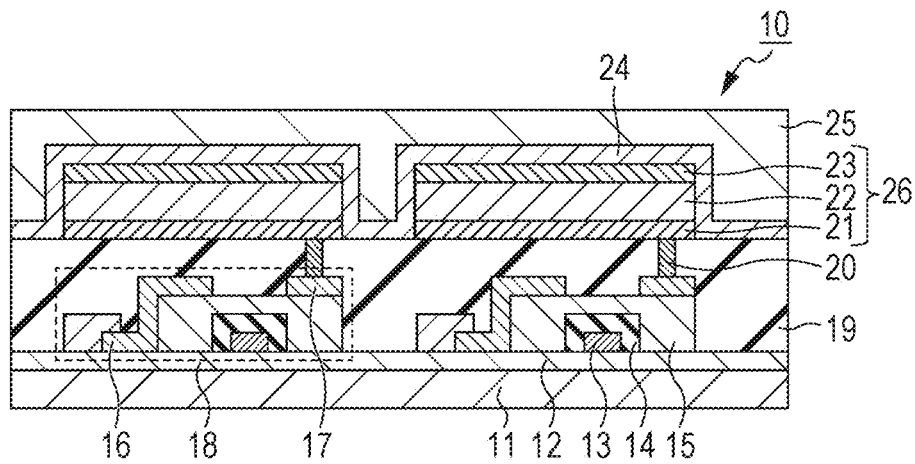
FIG. 4 is a schematic cross-sectional view of an example of a display apparatus including organic light-emitting devices according to an embodiment of the present disclosure.

An organic compound according to an embodiment will be described. The organic compound according to this embodiment is represented by formula [1] or [2].

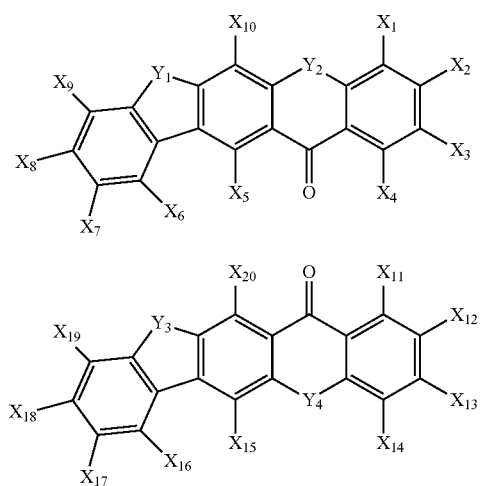

$X_1$ to $X_{20}$ $X_1$ to $X_{20}$ are each independently selected from a hydrogen atom, a halogen atom, a substituted or unsubstituted alkyl group, a substituted or unsubstituted alkoxy group, a substituted or unsubstituted amino group, a substituted or unsubstituted aromatic hydrocarbon group, a substituted or unsubstituted heterocyclic group, a substituted or unsubstituted aryloxy group, a substituted or unsubstituted heteroaryloxy group, a silyl group, and a cyano group. At least one of $X_1$ to $X_{10}$ and at least one of $X_1$ to $X_{20}$ are each a substituted or unsubstituted amino group or a group containing a substituted or unsubstituted amino group. Groups bonded to nitrogen atoms of the substituted or unsubstituted amino groups may be taken together to form a ring structure.

Non-limiting examples of the halogen atom include fluorine, chlorine, bromine, and iodine.

Non-limiting examples of the alkyl group include a methyl group, an ethyl group, a n-propyl group, an isopropyl group, a n-butyl group, a tert-butyl group, a sec-butyl group, an octyl group, a cyclohexyl group, a 1-adamantyl group, and a 2-adamantyl group. As the alkyl group, an alkyl group having 1 to 10 carbon atoms can be used.

Non-limiting examples of the alkoxy group include a methoxy group, an ethoxy group, a propoxy group, a 2-ethyloctyloxy group, and a benzyloxy group. As the alkoxy group, an alkoxy group having 1 to 10 carbon atoms can be used.

Non-limiting examples of the amino group include an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N,N-dinaphthylamino group, an N,N-difluorenylamino group, an N-phenyl-N-tolylamino group, an N,N-ditolylamino group, an N-methyl-N-phenylanino group, an N,N-dianisolylamino group, ab N-mesityl-N-phenylamino group, an N,N-dimesitylamino group, an N-phenyl-N-(4-tert-butylphenyl)amino group, an N-phenyl-N-(4-trifluoromethylphenyl)amino group, an N-piperidyl group, a carbazolyl group, and an acridyl group.

Examples of the amino group include amino groups each having any of structures illustrated below. In the following structural formulae, each * represents a binding position.

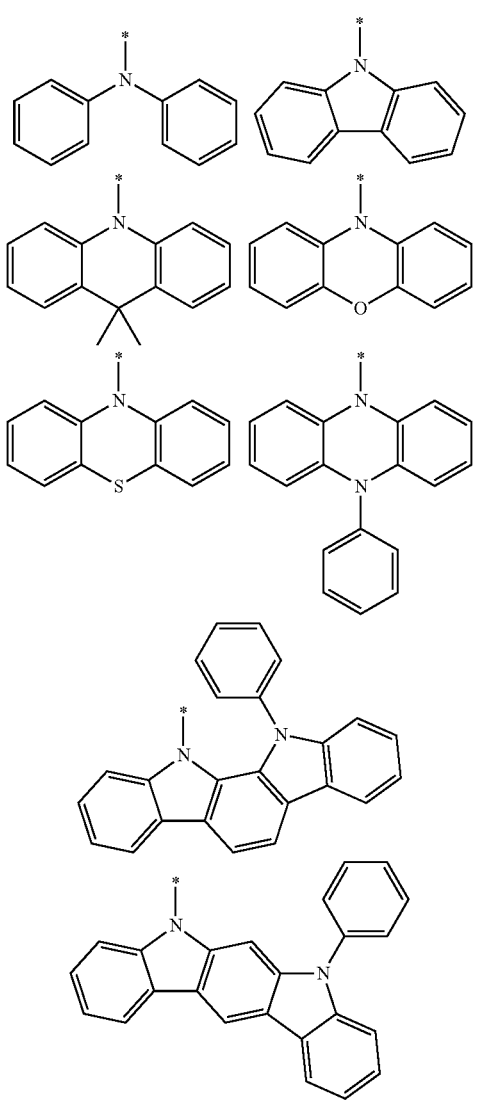

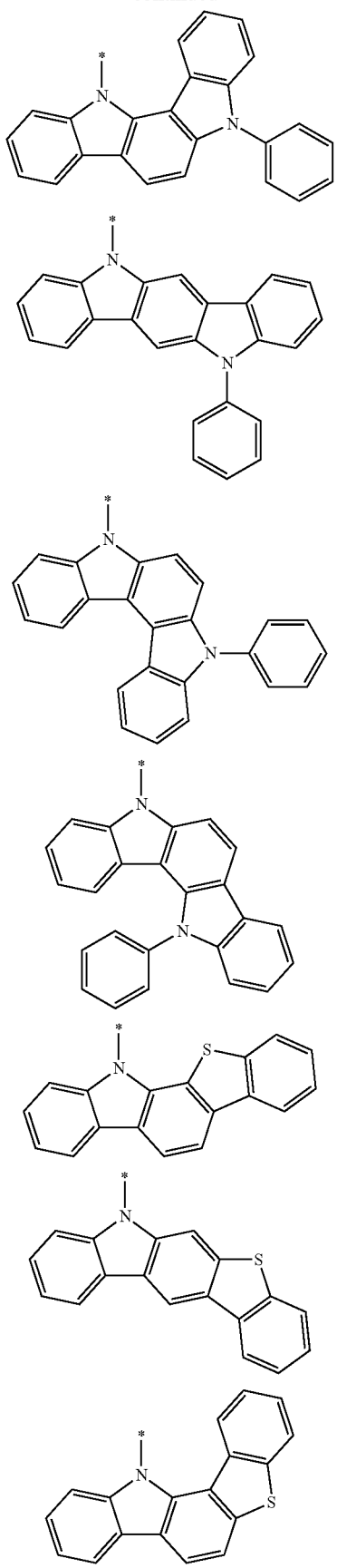
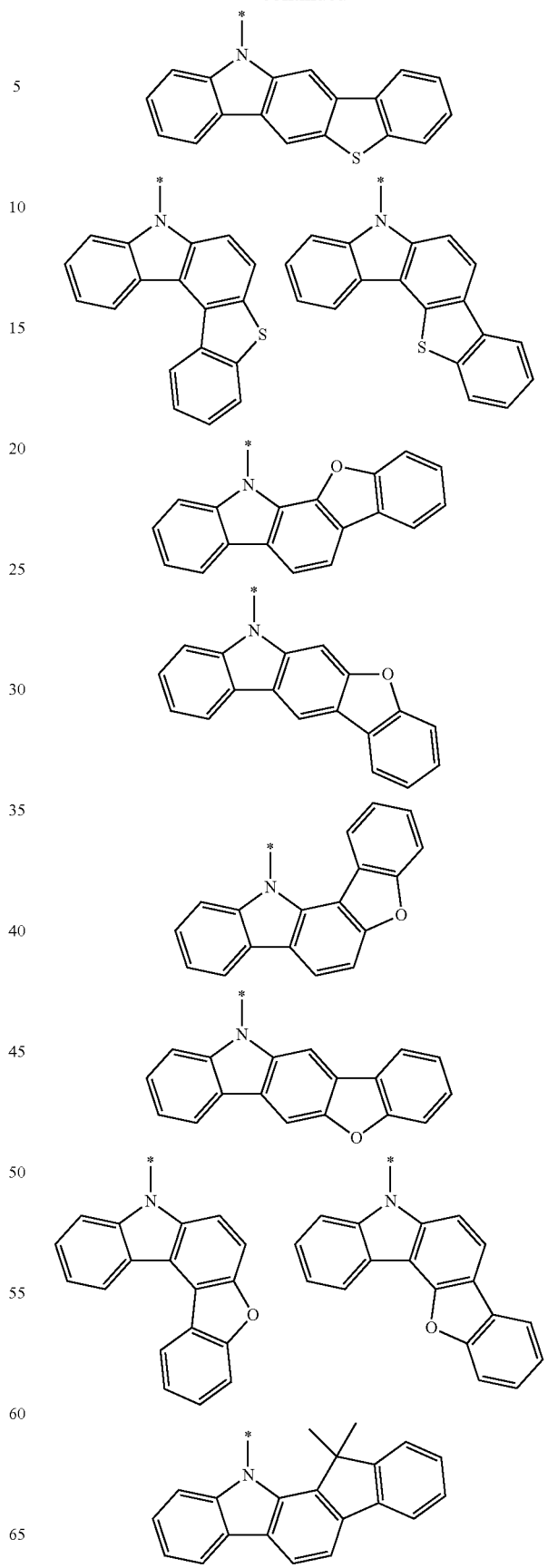

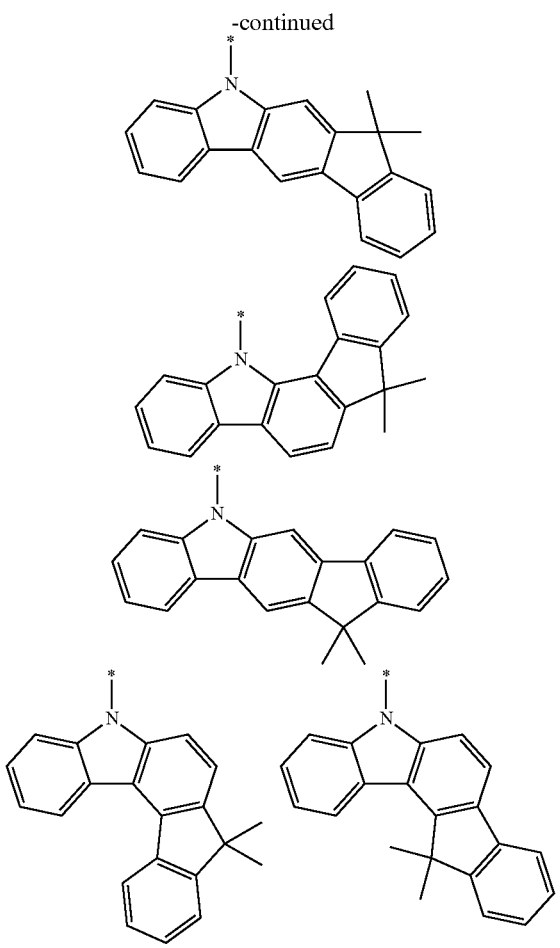

Non-limiting examples of the aromatic hydrocarbon group include a phenyl group, a naphthyl group, an indenyl group, a biphenyl group, a terphenyl group, a fluorenyl group, a phenanthryl group, a triphenylenyl group, a pyrenyl group, an anthracenyl group, a perylenyl group, a chrysenyl group, and a fluoranthenyl group. As the aromatic hydrocarbon group, an aromatic hydrocarbon group having 6 to 60 carbon atoms can be used.

Non-limiting examples of the heterocyclic group include a pyridyl group, a pyrimidinyl group, a pyrazinyl group, a triazinyl group, a benzofuranyl group, a benzothiophenyl group, a dibenzofuranyl group, a dibenzothiophenyl group, an oxazolyl group, an oxadiazolyl group, a thiazolyl group, a thiadiazolyl group, a carbazolyl group, an acridinyl group, and a phenanthrolinyl group. As the heterocyclic group, a heterocyclic group having 3 to 60 carbon atoms can be used.

Non-limiting examples of the aryloxy group include a phenoxy group and a naphthoxy group. Non-limiting examples of the heteroaryloxy group include a furanyloxy group and a thienyloxy group.

Non-limiting examples of the silyl group include a trimethylsilyl group and a triphenylsilyl group.

Non-limiting examples of substituents that may be further contained in the alkyl group, the alkoxy group, the amino group, the aromatic hydrocarbon group, the heterocyclic group, the aryloxy group, and the heteroaryloxy group include alkyl groups, such as a methyl group, an ethyl group, a n-propyl group, an isopropyl group, a n-butyl group, and a tert-butyl group; aralkyl groups, such as a benzyl group; aromatic hydrocarbon groups, such as a phenyl group, a biphenyl group, and a naphthyl group; heterocyclic groups, such as a pyridyl group, a pyrrolyl group, a pyrazinyl group, and a triazinyl group; amino groups, such as a dimethylamino group, a diethylamino group, a dibenzylamino group, a diphenylamino group, and a ditolylamino group; alkoxy groups, such as a methoxy group, an ethoxy group, and a propoxy group; alkoxy groups, such as a methoxy group, an ethoxy group, and a propoxy group; aryloxy groups, such as a phenoxy group; halogen atoms, such as fluorine, chlorine, bromine, and iodine atoms; and a cyano group. Groups bonded to nitrogen atoms of the amino groups that may be further contained may be taken together to form a ring structure.

At least one of $X_6$ to $X_9$ and At least one of $X_{16}$ to $X_{19}$ can each be a substituted or unsubstituted amino group or a group containing a substituted or unsubstituted amino group and can each be a substituted or unsubstituted amino group. $X_1$ to $X_4$ and $X_{11}$ to $X_{14}$ can each be a hydrogen atom, a substituted or unsubstituted alkyl group, a phenyl group, a biphenyl group, a naphthyl group, a pyridyl group, a pyrazinyl group, a triazinyl group, fluorine, or a cyano group.

$Y_1$ to $Y_4$ $Y_1$ and $Y_3$ are each oxygen, sulfur, selenium, tellurium, a carbonyl group, or a $CR_1R_2$ group and may be the same or different. $Y_1$ and $Y_3$ can each be oxygen, sulfur, or a $CR_1R_2$ group.

$R_1$ and $R_2$ are each independently selected from a hydrogen atom, a halogen atom, a substituted or unsubstituted alkyl group, a substituted or unsubstituted alkoxy group, a substituted or unsubstituted amino group, a substituted or unsubstituted aromatic hydrocarbon group, a substituted or unsubstituted heterocyclic group, a substituted or unsubstituted aryloxy group, a substituted or unsubstituted heteroaryloxy group, a silyl group, and a cyano group.

Specific examples of the halogen atom, the alkyl group, the alkoxy group, the amino group, the aromatic hydrocarbon group, the heterocyclic group, the aryloxy group, the heteroaryloxy group, and the silyl group that are represented by $R_1$ and $R_2$ are, but not limited to, the same as those described for $X_1$ to $X_{20}$. As the alkyl group, an alkyl group having 1 to 10 carbon atoms can be used. As the alkoxy group, an alkoxy group having 1 to 10 carbon atoms can be used. As the aromatic hydrocarbon group having 6 to 60 carbon atoms can be used. As the heterocyclic group, a heterocyclic group having 3 to 60 carbon atoms can be used. Specific examples of substituents that may further be contained in the alkyl group, the alkoxy group, the amino group, the aromatic hydrocarbon group, the heterocyclic group, the aryloxy group, and the heteroaryloxy group are, but not limited to, the same as those described for $X_1$ to $X_{20}$.

$Y_2$ and $Y_4$ are each oxygen, sulfur, selenium, or tellurium and may be the same or different. $Y_2$ and $Y_4$ can each be oxygen or sulfur.

A method for synthesizing an organic compound according to this embodiment of the present disclosure will be described below. The organic compound according to the embodiment of the present disclosure is synthesized, for example, by a reaction scheme described below.

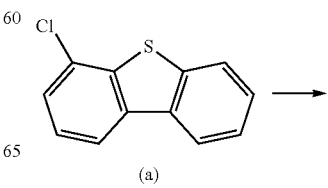

(a)

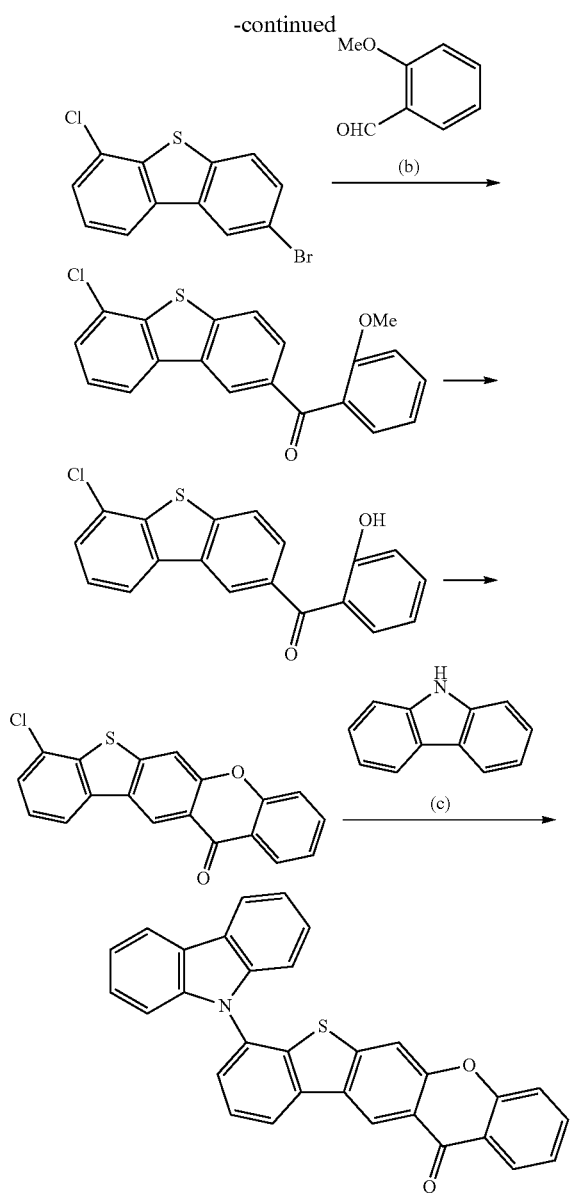

Here, each of the compounds represented by formulae [1] and [2] can be synthesized by appropriately changing compounds (a) to (c). The synthesis method is not limited thereto.

The organic compound according to the embodiment has features described below. The use of the organic compound according to the embodiment for an organic light-emitting device allows the organic light-emitting device to have high luminous efficiency and excellent driving durability characteristics. A basic skeleton in this embodiment is a skeleton in which in the compound represented by formula [1] or [2], $X_1$ to $X_{20}$ are each a hydrogen atom, and when $Y_1$ and $Y_3$ are each a $CR_1R_2$ group, $R_1$ and $R_2$ are each a hydrogen atom.

(1) A structure in which an electron-withdrawing carbonyl group is fused to a fused-ring skeleton containing a five-membered ring is included as a basic skeleton, and at least one of $X_1$ to $X_{10}$ and at least one of $X_{11}$ to $X_{20}$ are each an electron-donating amino group or a group containing an electron-donating amino group, so that the energy gap between $S_1$ and $T_1$ is small.

(2) The carbonyl group-containing structure having a high degree of flatness is included as the basic skeleton, and at least one of $X_1$ to $X_{10}$ and at least one of $X_{11}$ to $X_{20}$ are each an amino group that reduces the flatness or a group having an amino group that reduces the flatness, so that the molecular aspect ratio is low, and the molecular association is less likely to occur.

These features will be described below.

(1) A structure in which an electron-withdrawing carbonyl group is fused to a fused-ring skeleton containing a five-membered ring is included as a basic skeleton, and at least one of $X_1$ to $X_{10}$ and at least one of $X_{11}$ to $X_{20}$ are each an electron-donating amino group or a group containing an electron-donating amino group, so that the energy gap between $S_1$ and $T_1$ is small.

The inventors have focused on the electron distribution of the highest occupied molecular orbital (HOMO) and the lowest unoccupied molecular orbital (LUMO) of the compound represented by formula [1] or [2] in creating the organic compound.

As presented in FIG. 1, in each of exemplified compounds B-1 to B-5, C-1, and D-1, which are compounds according to the embodiment, a moiety occupying the electron orbital distribution of HOMO and a moiety occupying the electron orbital distribution of LUMO are separated. In other words, it can be seen that a portion occupying both the HOMO and LUMO is small.

This leads to a small overlap integral and a small energy difference between the excited singlet state ($S_1$) and the excited triplet state ($T_1$). Specifically, the energy gaps between $S_1$ and $T_1$ of B-1 to B-5, C-1, and D-1 are as small as 0.26 eV, 0.15 eV, 0.15 eV, 0.32 eV, 0.32 eV, 0.25 eV, and 0.19 eV, respectively. In contrast, the energy gap between $S_1$ and $T_1$ of comparative compound 1 is as large as 0.72 eV. Comparative compound 1 is compound A-1, which is described in Non-Patent Literature 1.

The above feature is the effect due to the fact that the five-membered ring-containing fused-ring skeleton as the basic skeleton contains an electron-withdrawing carbonyl group and an electron-donating amino group as a substituent. In contrast, in the structure that does not contain an amino group, such as comparative compound 1, a moiety occupying the electron orbital distribution of the HOMO and a moiety occupying the electron orbital distribution of the LUMO are not separated. This results in a large energy gap between $S_1$ and $T_1$.

The above electron orbital distributions of the HOMO and the LUMO were visualized using molecular orbital calculations. As the molecular orbital calculation method, the density functional theory (DFT), which is widely used at present, was used with the B3LYP functional and 6-31G* as the basis function. The molecular orbital calculation method was performed using Gaussian 09 (Gaussian 09, Revision C.01, M. J. Frisch, G. W. Trucks, H. B. Schlegel, G. E. Scuseria. M. A. Robb, J. R. Cheeseman, G. Scalmani, V. Barone, B. Mennucci, G. A. Petersson, H. Nakatsuji, M. Caricato, X. Li, H. P. Hratchian, A. F. Izmaylov, J. Bloino, G. Zheng, J. L. Sonnenberg, M. Hada, M. Ehara, K. Toyota, R. Fukuda, J. Hasegawa, M. Ishida, T. Nakajima, Y. Honda, O. Kitao, H. Nakai, T. Vreven, J. A. Montgomery, Jr., J. E. Peralta. F. Ogliaro, M. Bearpark, J. J. Heyd, E. Brothers, K. N. Kudin, V. N. Staroverov, T. Keith, R. Kobayashi, J. Normand, K. Raghavachari, A. Rendell, J. C. Burant, S. S. Iyengar, J. Tomasi, M. Cossi, N. Rega, J. M. Millam, M. Klene, J. E. Knox, J. B. Cross, V. Bakken. C. Adamo, J. Jaramillo, R. Gomperts, R. E. Stratmann, O. Yazyev, A. J. Austin, R. Cammi, C. Pomelli, J. W. Ochterski, R. L. Martin, K. Morokuma. V. G. Zakrzewski, G. A. Voth, P. Salvador, J. J. Dannenberg, S. Dapprich, A. D. Daniels, O. Farkas, J. B. Foresman, J. V. Ortiz, J. Cioslowski, and D. J. Fox, Gaussian, Inc., Wallingford CT, 2010), which is widely used at present. In this specification, hereinafter, the same method is employed for molecular orbital calculations.

As described above, each of the compounds according to the embodiment is characterized in that the difference between $S_1$ and $T_1$ is small. When the compound according to the embodiment is used in the light-emitting layer of an organic light-emitting device, the device having high luminous efficiency is provided. The reason for this is as follows: For excitons consisting of singlet and triplet excitons in a ratio of 1:3, the triplet excitons, which undergo thermal deactivation normally, can be used for delayed fluorescence from the excited singlet state due to the small energy difference between $S_1$ and $T_1$. For reverse intersystem crossing to convert the triplet excitons into the excited singlet state, a smaller energy difference between $S_1$ and $T_1$ is advantageous because of a smaller energy barrier. The compound according to the embodiment is advantageous for that condition. Thus, the device having high luminous efficiency can be provided.

(2) The carbonyl group-containing structure having a high degree of flatness is included as the basic skeleton, and at least one of $X_1$ to $X_{10}$ and at least one of $X_{11}$ to $X_{20}$ are each an amino group that reduces the flatness or a group having an amino group that reduces the flatness, so that the molecular aspect ratio is low, and the molecular association is less likely to occur.

The inventors have focused on the flatness of the compound represented by the formula [1] or [2] in creating the organic compound. The basic skeleton of the compound according to the embodiment has a structure in which an electron-withdrawing carbonyl group is fused to a fused-ring skeleton containing a five-membered ring, and thus the structure has a high degree of flatness. The high degree of flatness easily causes molecular stacking. In other words, molecular association may occur easily. In organic light-emitting devices, molecular association leads to a decrease in efficiency due to concentration quenching. It is also disadvantageous for reverse intersystem crossing. This is because triplet-triplet exciton annihilation (TTA) due to energy transfer of triplet excitons between molecules occurs easily, and reverse intersystem crossing to singlet excitons does not easily occur.

The inventors have found that an amino group is introduced as a substituent. The introduction of an amino group can reduce the molecular aspect ratio and the molecular association.

The molecular aspect ratio used in the embodiment is defined as the ratio of the maximum molecular length (molecular diameter) in the xy-plane containing the basic skeleton to the molecular length (molecular thickness) in the z-axis direction perpendicular to the xy-plane containing this basic skeleton, i.e., molecular aspect ratio=(molecular diameter)/molecular thickness). In other words, a higher molecular aspect ratio results in a higher degree of flatness. A lower molecular aspect ratio results in a lower degree of flatness and can reduce molecular association. Specifically, the molecular aspect ratio is preferably 5.0 or less, more preferably 3.0 or less. The molecular lengths of the molecular diameters and the molecular thicknesses were calculated from the molecular lengths in ball-and-bond representations using molecular structures determined from optimized structure calculations.

FIG. 2 presents the comparison results of the molecular aspect ratios. FIG. 2 indicates that the molecular aspect ratios of exemplified compounds B-1, D-1, and B-26 according to the embodiment are 1.8, 1.7, and 4.0, respectively, whereas the molecular aspect ratio of comparative compound 1 is as high as 8.3. This is due to the presence of an amino group as a substituent.

As described above, since the compound according to the embodiment has a low molecular aspect ratio, molecular stacking is less likely to occur, and thus molecular association is less likely to occur.

The above feature is also effective in improving the amorphous nature of the organic compound. In the case where the compound according to the embodiment is used in the organic layer of an organic light-emitting device, a stable amorphous film that is less likely to crystallize is formed, and the organic light-emitting device has high durability without the occurrence of crystallization even in the case of long-term operation.

The above feature is also effective in improving sublimability. The improvement of sublimability enables the purification of the material by sublimation and the production of an organic light-emitting device by vapor deposition. This can reduce the amount of impurities contained in the organic light-emitting device and can inhibit deteriorations in luminous efficiency and driving durability due to impurities.

The organic compound can further satisfy the conditions (3) and (4) described below.

(3) At least one of $X_6$ to $X_9$ and at least one of $X_{16}$ to $X_{19}$ are each an amino group or a group containing an amino group.

This is because when condition (3) above is satisfied, the distance between the electron-withdrawing carbonyl group in the basic skeleton and the electron-donating amino group as a substituent is increased, thus resulting in improved separation of the electron orbital distributions of the HOMO and LUMO described in feature (1) above. This results in a smaller energy gap between $S_1$ and $T_1$. Specifically, as presented in FIG. 1, the energy gaps between $S_1$ and $T_1$ of exemplified compounds B-2 and B-4 are 0.15 eV and 0.32 eV, respectively. It can be seen that the energy gap between $S_1$ and $T_1$ of exemplified compound B-2, in which any of $X_6$ to $X_9$ is an amino group, is smaller than that of exemplified compound B-4, in which any of $X_1$ to $X_4$ is an amino group. This is advantageous for reverse intersystem crossing and increases delayed fluorescence, so that a device with high luminous efficiency can be provided.

(4) At least one of $X_6$ to $X_9$ and at least one of $X_{16}$ to $X_{19}$ are each an amino group.

This is because when condition (4) above is satisfied, the steric hindrance between the basic skeleton and the amino group, which is a substituent, results in a larger molecular thickness and thus a lower molecular aspect ratio described in feature (2) above. This can reduce the degree of molecular flatness to reduce the molecular association, resulting in a reduction in concentration quenching. In addition, TTA can be reduced to promote the reverse intersystem crossing. Thus, the highly efficient light-emitting device can be provided. The low degree of molecular flatness leads to improved amorphous nature and sublimability and thus is also advantageous for durability characteristics.

FIG. 3 presents the comparative results of the case where an amino group is bonded to the basic skeleton and the case where a group containing an amino group is bonded to the basic skeleton. The molecular aspect ratios of exemplified compounds D-5 and D-6 are 1.6 and 2.4, respectively. These compounds have the same molecular weight and contain an amino group or a group containing an amino group at the same substitution position. It can be seen that exemplified compound D-5, in which an amino group is bonded to the basic skeleton, has a lower molecular aspect ratio.

Moreover, the compound can be a compound that satisfies condition (5) below.

(5) At least one of $X_6$ to $X_9$ and at least one of $X_{16}$ to $X_{19}$ are each an amino group having any of the following structures, where each * represents a binding position.

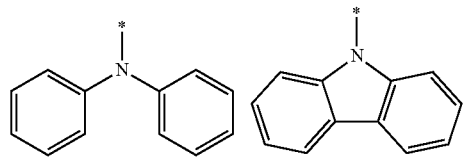

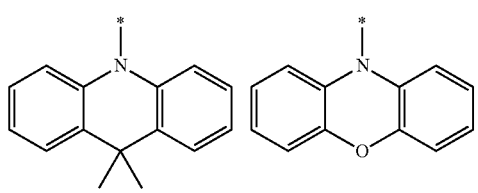

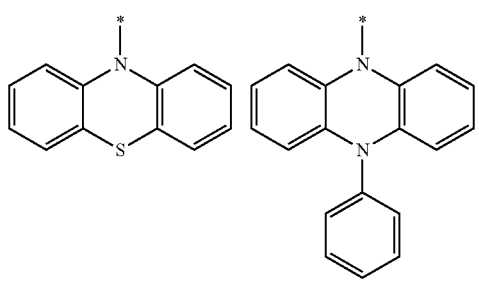

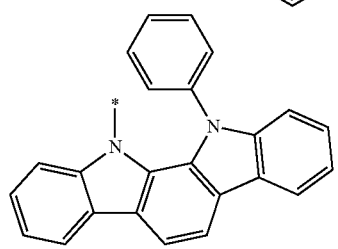

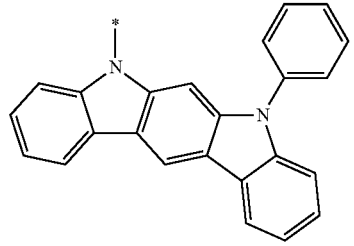

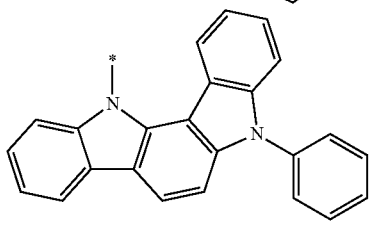

-continued

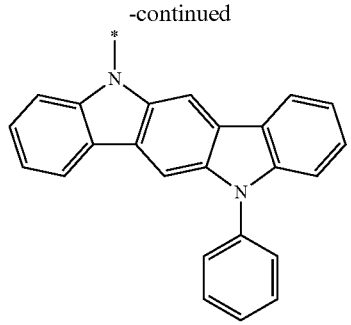

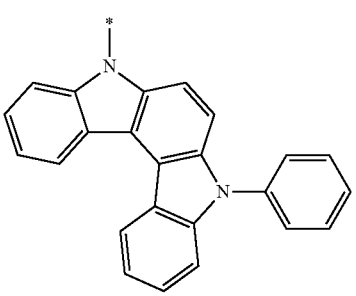

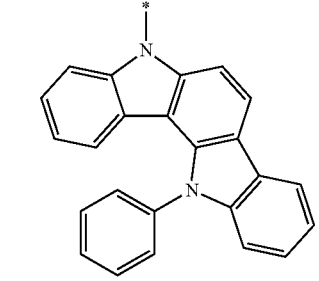

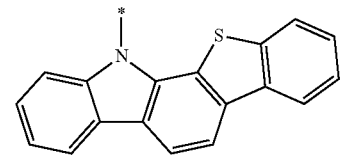

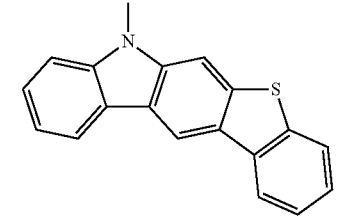

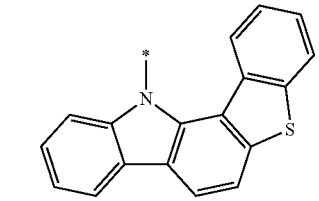

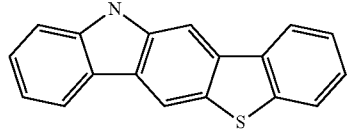

-continued

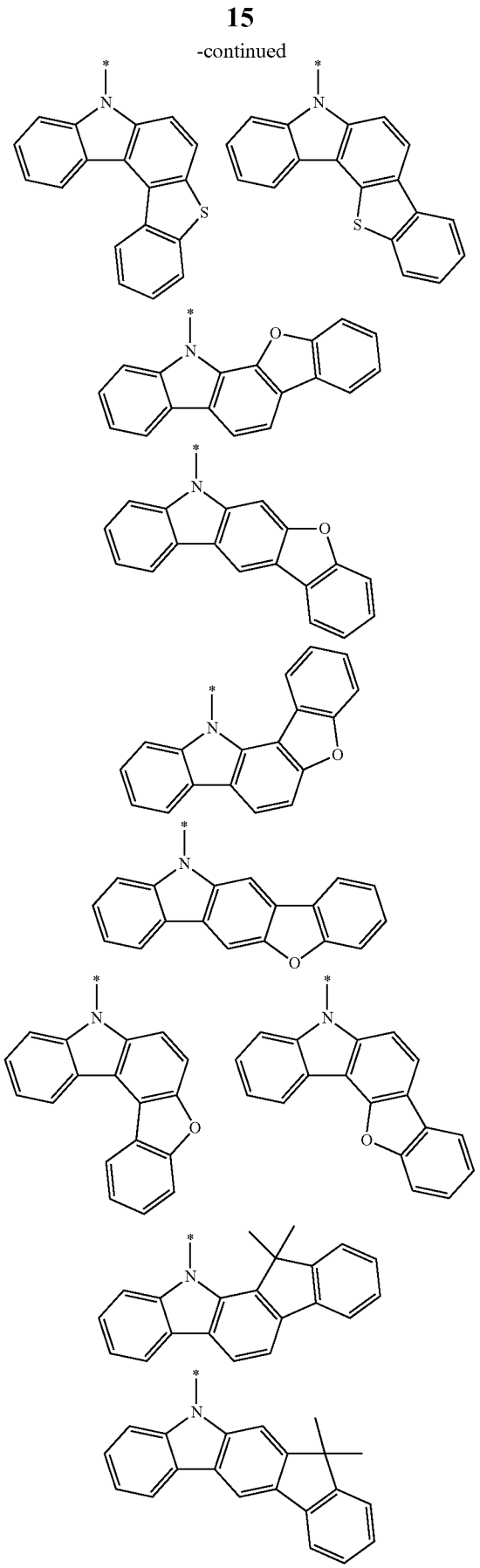

-continued

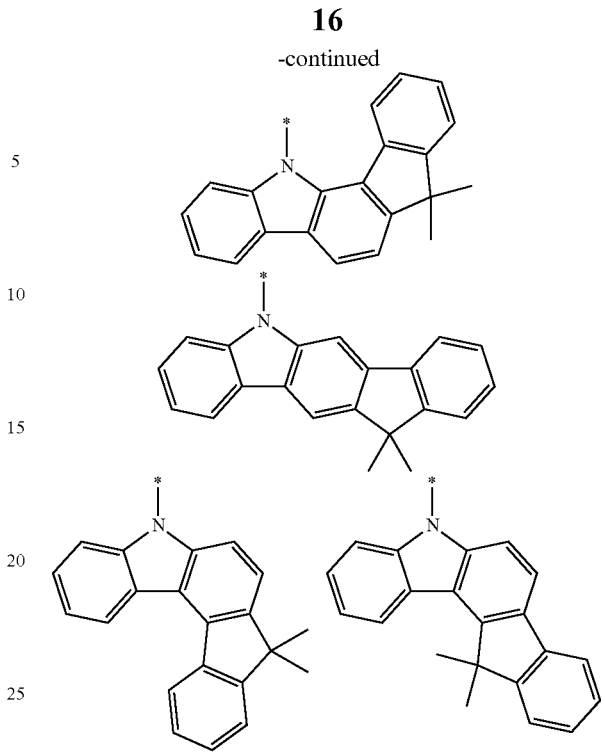

This is because when condition (5) above is satisfied, the presence of the amino group as a substituent leads to a larger molecular thickness, thereby resulting in a low molecular aspect ratio, which is described in feature (2) above. Specifically, as presented in FIG. 2, the molecular aspect ratios of exemplified compounds B-1 and B-26 are 1.8 and 4.0, respectively. It can be seen that exemplified compound B-1, in which the substituent amino group is selected from amino groups having the above structures, has a lower molecular aspect ratio. This can reduce the degree of molecular flatness to reduce the molecular association. Thus, TTA can be reduced to promote the reverse intersystem crossing. This is advantageous for higher efficiency of the device. The low degree of molecular flatness leads to improved amorphous nature and sublimability and thus is also advantageous for durability characteristics.

Furthermore, the compound according to the embodiment can be used in the light-emitting layer of an organic light-emitting device. In this case, the compound has the following features.

(6) The compound according to the embodiment is mixed with a host material in the light-emitting layer to facilitate exciton recombination of the compound according to the embodiment, thereby providing the light-emitting device with high efficiency.

(7) The mixture of the compound according to the embodiment and the host material in the light-emitting layer and the presence of a light-emitting material provide the light-emitting device with high efficiency and high color purity.

(8) The use of a hydrocarbon compound as the light-emitting material provides the light-emitting device with high efficiency and good durability characteristics.

Features (6) to (8) above will be described below.

(6) The compound according to the embodiment is mixed with a host material in the light-emitting layer to facilitate exciton recombination of the compound according to the embodiment, thereby providing the light-emitting device with high efficiency.

The compound according to the embodiment is a compound containing an electron-withdrawing carbonyl group and an electron-donating amino group. When the compound according to the embodiment is mixed with the host material in the light-emitting layer of the organic light-emitting device, the light-emitting layer is an electron-trapping light-emitting layer due to the contribution of the electron-withdrawing properties or a hole-trapping light-emitting layer due to the contribution of the electron-donating properties.

Accordingly, in the light-emitting layer, electrons or holes fed from a transport layer are trapped by the compound according to the embodiment, and exciton recombination occurs. As described in feature (1) above, the compound according to the embodiment has a small energy difference between $S_1$ and $T_1$, can efficiently produce delayed fluorescence in the light-emitting layer, and can use a larger number of triplet excitons for light emission.

In particular, when the host material is a hydrocarbon compound, the LUMO level of the compound according to the embodiment tends to be lower (farther from the vacuum level) than that of the host material, or the HOMO level of the compound according to the embodiment tends to be higher (closer to the vacuum level) than that of the host material. For this reason, electrons or holes are more easily trapped, resulting in higher efficiency. The hydrocarbon compound is a compound that consists of only carbon and hydrogen in its molecule.

As described in feature (2) above, the compound according to the embodiment is less likely to undergo molecular association, and thus is less likely to undergo concentration quenching in the host material. This effect leads to the prevention of quenching due to exciton interaction when the compound according to the embodiment is in the excited state, and is effective in efficiently producing delayed fluorescence in the light-emitting layer.

(7) The mixture of the compound according to the embodiment and the host material in the light-emitting layer and the presence of a light-emitting material provide the light-emitting device with high efficiency and high color purity.

The use of the light-emitting layer that contains the compound according to the embodiment and that is doped with a light-emitting material having a high emission quantum yield or doped with a light-emitting material whose emission spectrum has a spectrum suitable for exhibiting high color purity provides a light-emitting device having even higher efficiency and high color purity. In this case, the compound according to the embodiment needs to be contained in a concentration sufficient to preferentially trap electrons and holes in the light-emitting layer in order to facilitate exciton recombination. The concentration of the organic compound according to the embodiment in the light-emitting layer needs to be preferably 0.1% or more by mass and 45% or less by mass, more preferably 1% or more by mass and 35% or less by mass. The light-emitting material having a smaller doping concentration is less susceptible to the influence of concentration quenching and a change in emission spectrum due to the intermolecular interaction. Thus, the light-emitting layer can be doped with the light-emitting material other than the compound according to the embodiment. The doping concentration of the light-emitting material is preferably 0.01% or more by mass and 20% or less by mass, more preferably 1% or more by mass and 15% or less by mass. Accordingly, it is possible to provide the light-emitting device with high efficiency and high color purity.

(8) The use of a hydrocarbon compound as the light-emitting material provides the light-emitting device with high efficiency and good durability characteristics.

The compound according to the embodiment contains a strong electron-withdrawing carbonyl group. Because of this, as a light-emitting material serving as a dopant described in feature (7) above, a light-emitting material that does not contain an electron-donating amino group can be used, and a hydrocarbon compound can be used. The reason for this is that an amino group-containing light-emitting material may interact with the carbonyl group of the compound according to the embodiment in the light-emitting layer to cause a decrease in luminous efficiency due to exciplex formation and a change in the emission spectrum of the light-emitting material, thereby deteriorating the color purity of the light-emitting device.

An amino group-containing light-emitting material is easily oxidized due to its low ionization potential and thus has poor device durability. For this reason, a hydrocarbon compound can be used as a light-emitting material, and a five-membered ring-containing fused polycyclic compound can be used. This is because the structure is less susceptible to oxidation due to its higher ionization potential. The hydrocarbon compound is a compound consisting of only carbon and hydrogen in its molecule.

As described above, the high-efficiency organic light-emitting device can be provided by mixing the compound according to the embodiment with the host material in the light-emitting layer. Here, the light-emitting material may be the compound according to the embodiment. In addition, a light-emitting material may be mixed, and the compound according to the embodiment may function as an assist material. The use of a light-emitting material with good color purity makes it possible to provide an organic light-emitting device with high efficiency and high color purity. When the host material is a hydrocarbon compound, the compound according to the embodiment can easily trap electrons and holes to contribute to higher efficiency.

Specific examples of the organic compound according to the embodiment are illustrated below. However, the present disclosure is not limited thereto.

B-1

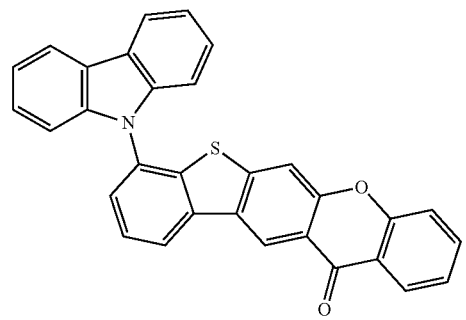

B-2
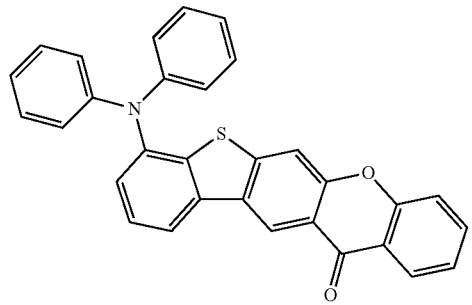
B-3
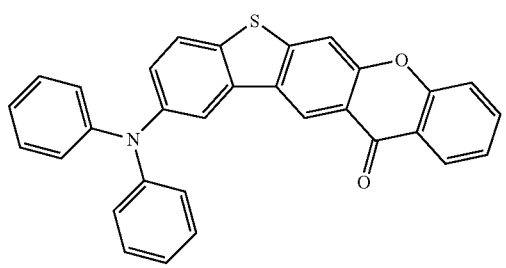
B-4
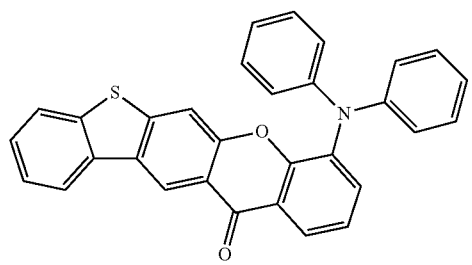
B-5
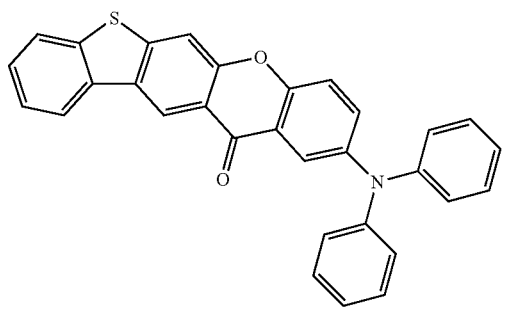
B-6
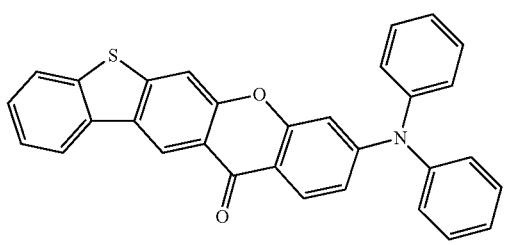
B-7
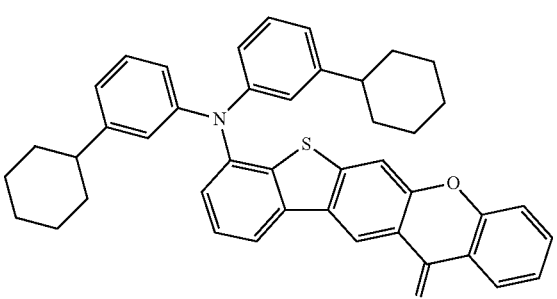
B-8
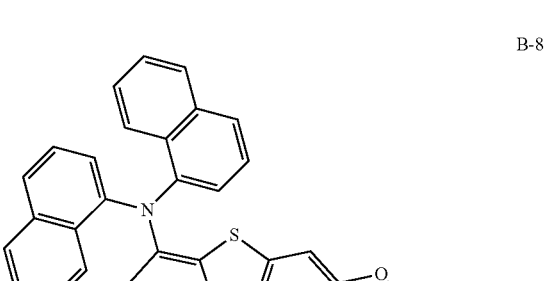
B-9
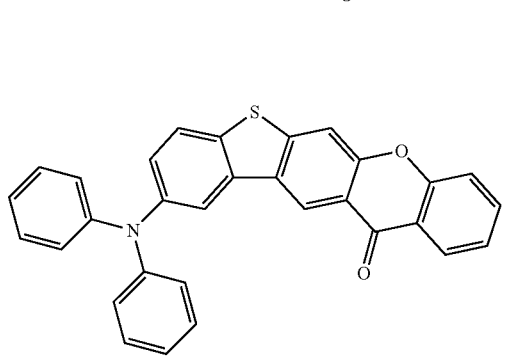
B-10
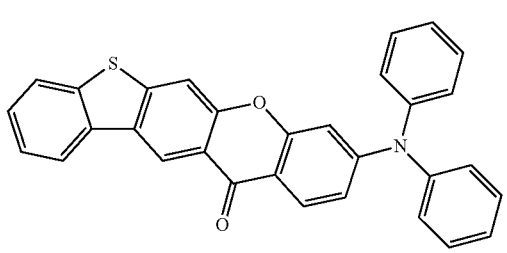

B-11
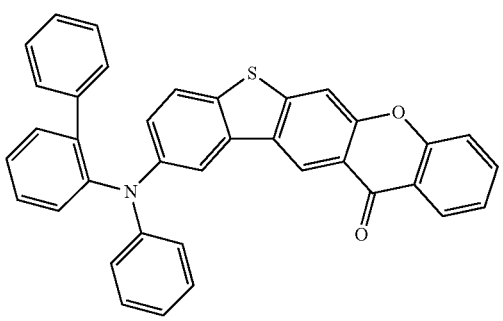
B-12
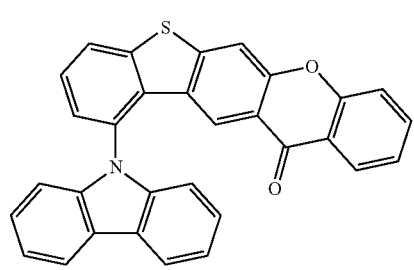
B-13
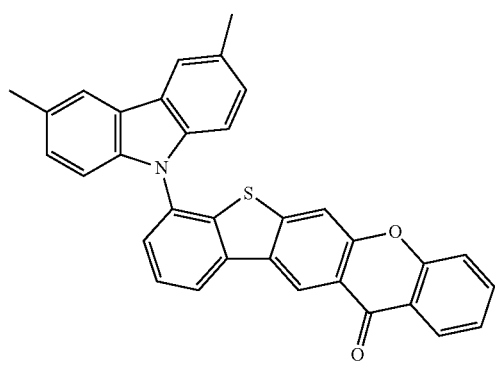
B-14
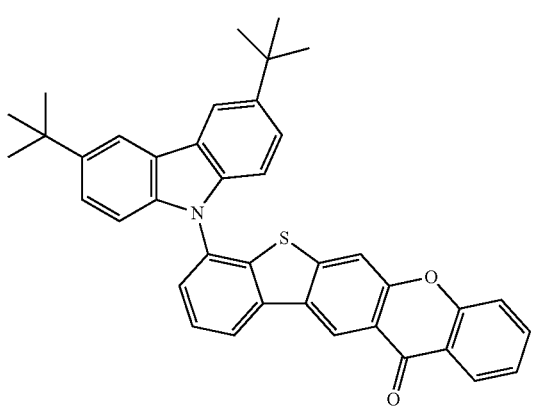
B-15
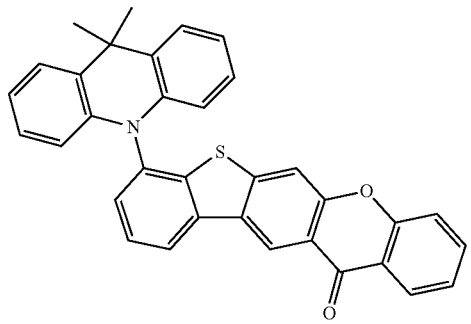
B-16
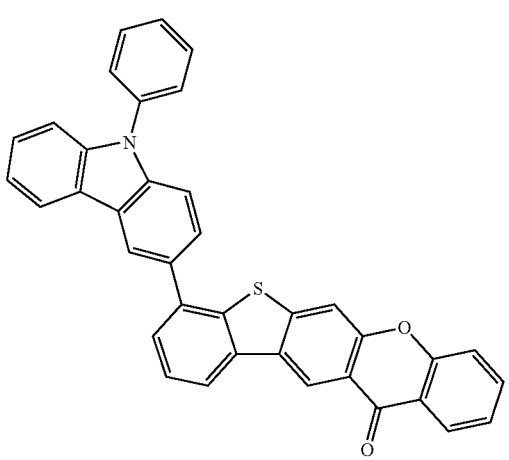
B-17
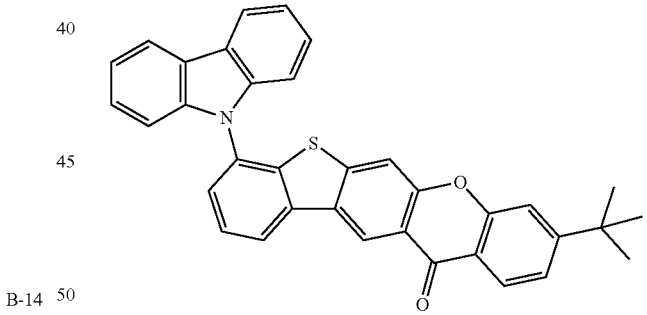
B-18
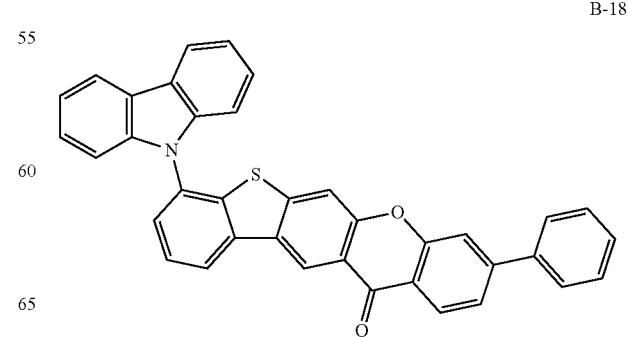

B-19
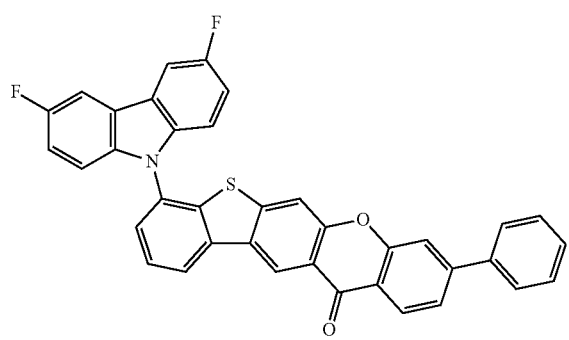
B-20
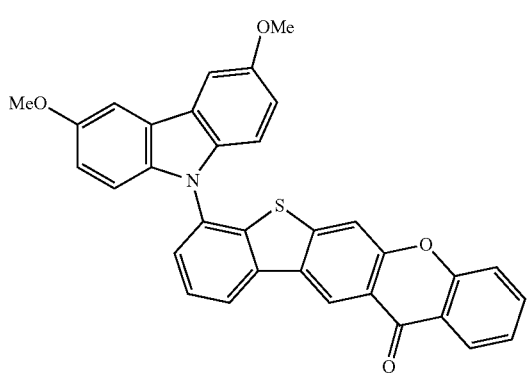
B-21
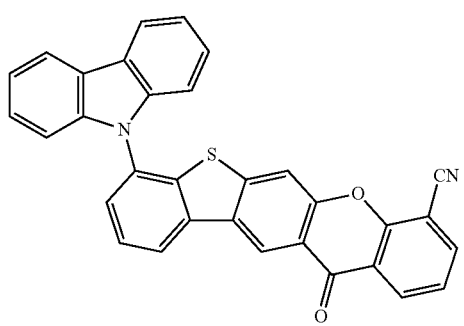
B-22
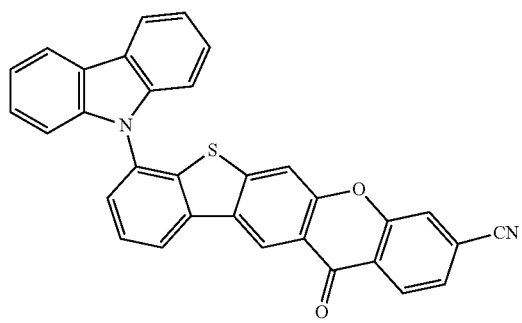
B-23
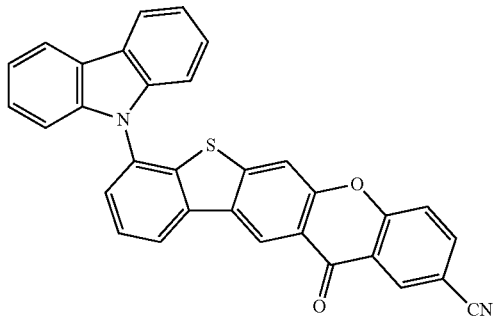
B-24
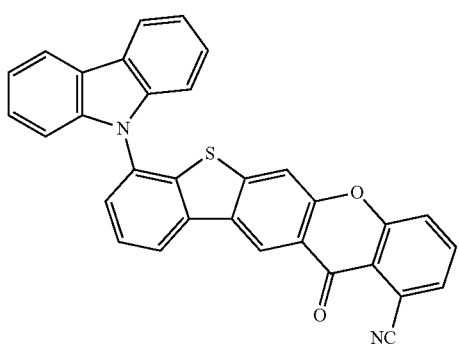
B-25
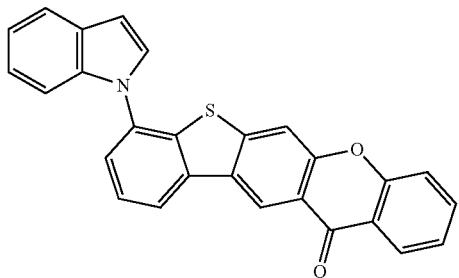
B-26
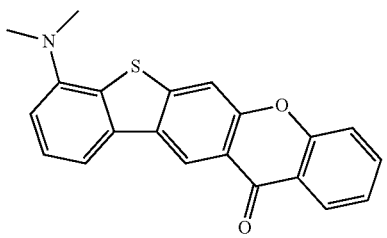
B-27
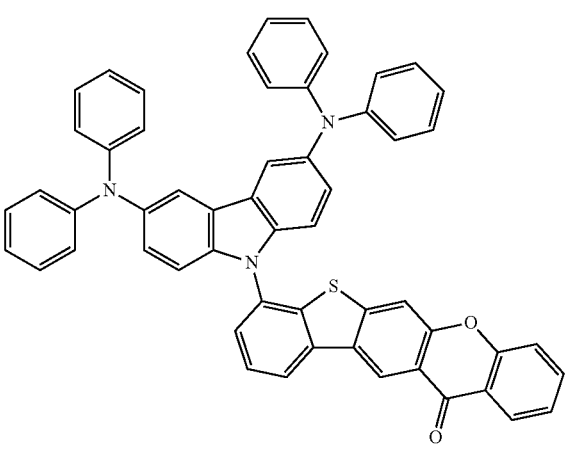

B-28

C-1

C-2

C-3

C-4

C-5

C-6

C-7

C-8

C-9
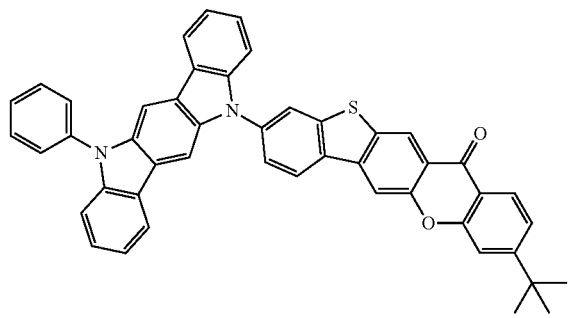
C-14
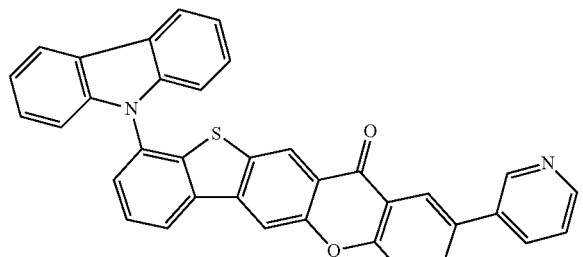
C-10
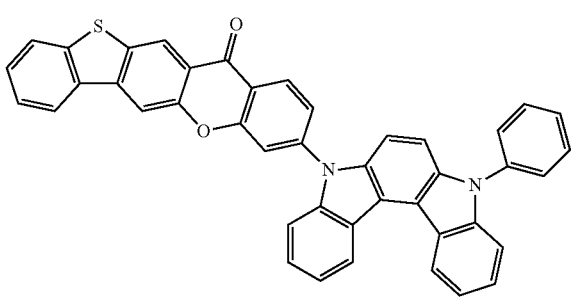
C-15
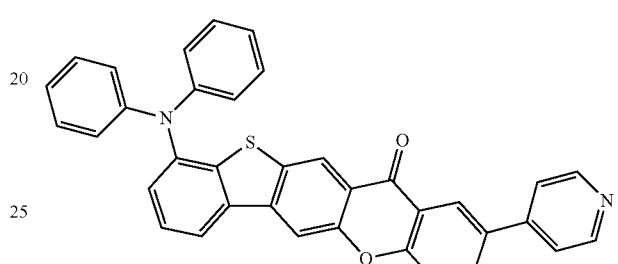
C-11
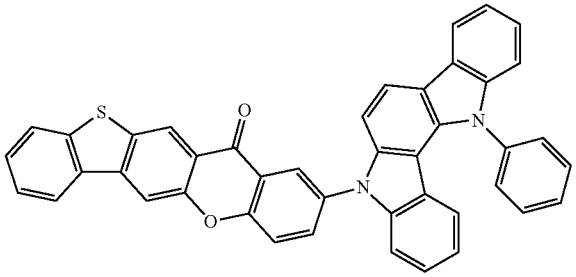
C-16
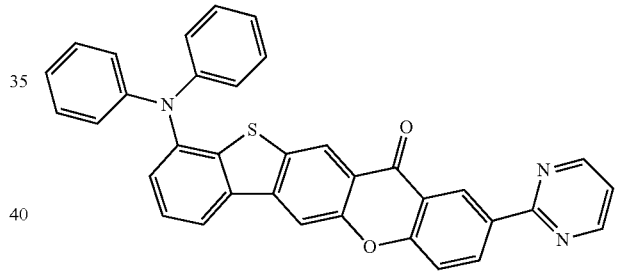
C-12
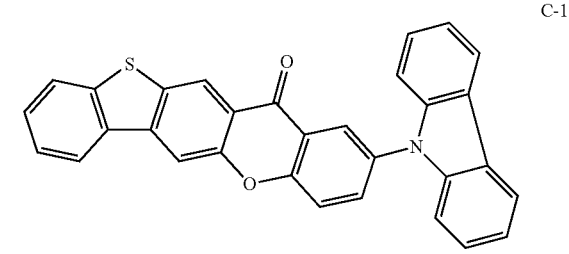
C-17
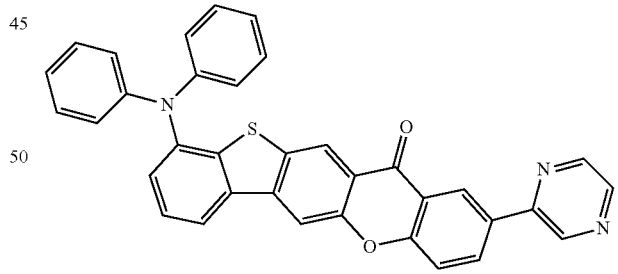
C-13
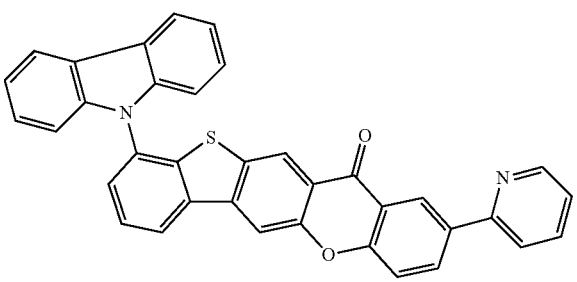
C-18
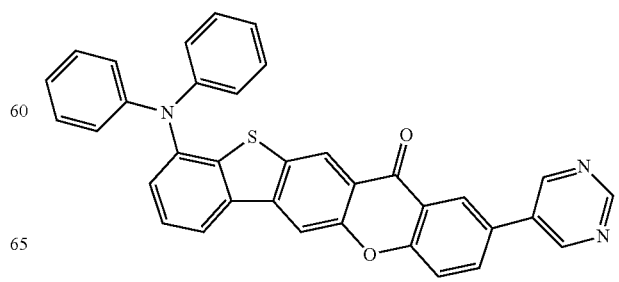

C-19
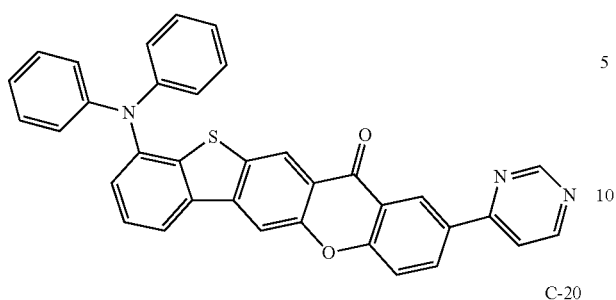
C-20
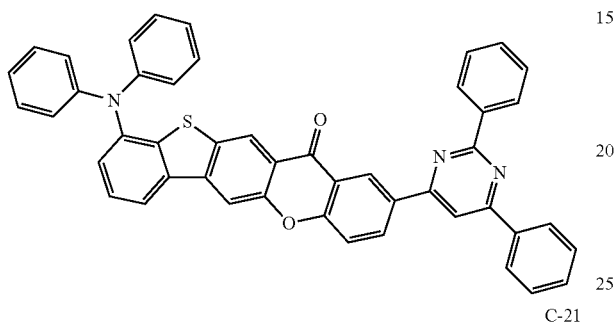
C-21
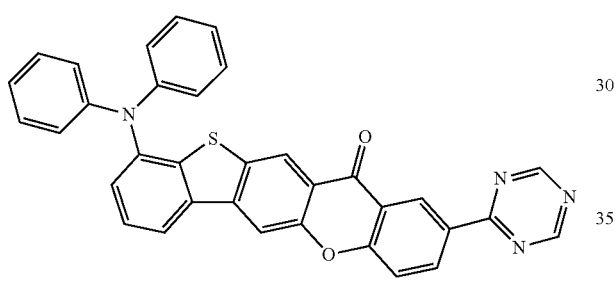
C-22
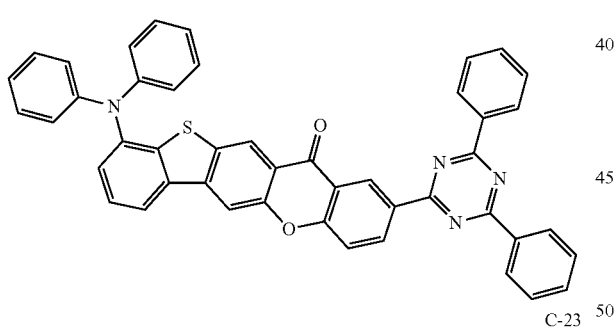
C-23
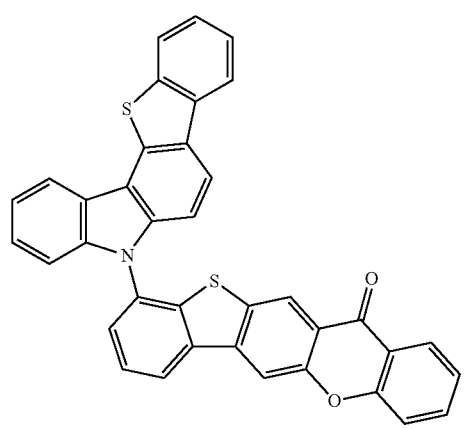
C-24
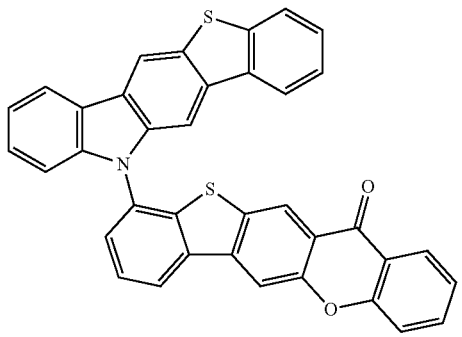
C-25
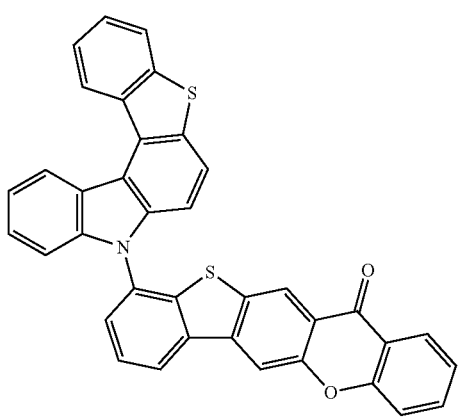
C-26
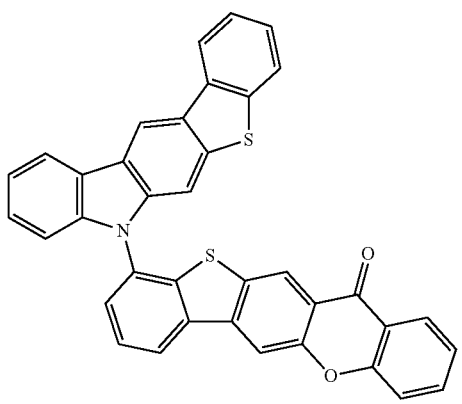
C-27
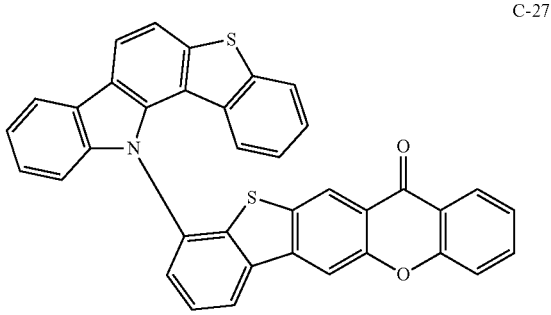

C-28
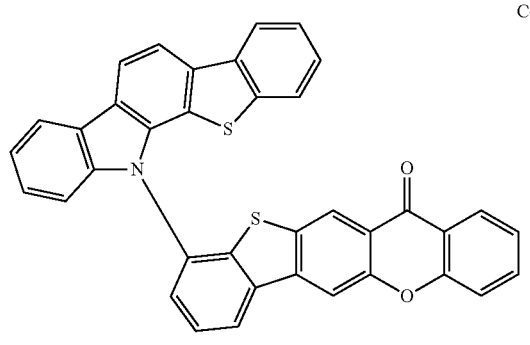
D-1
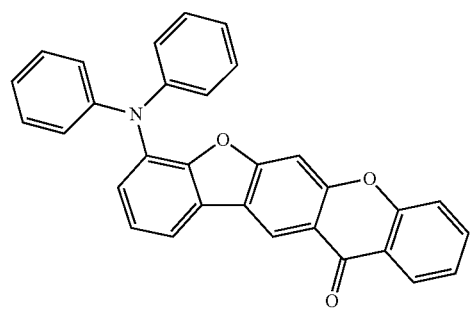
D-2
D-3
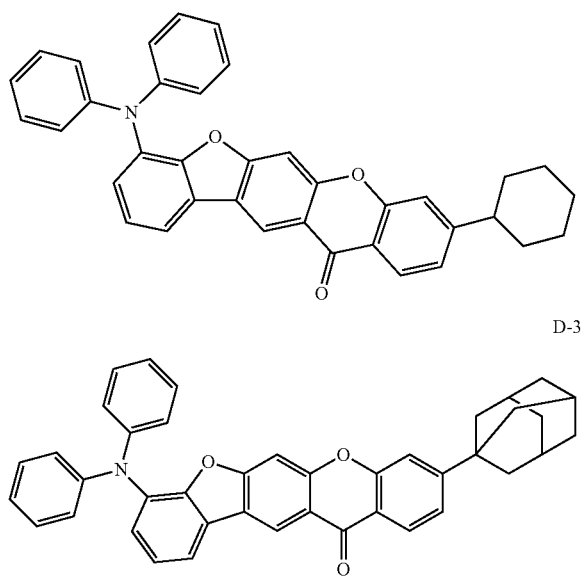
D-4
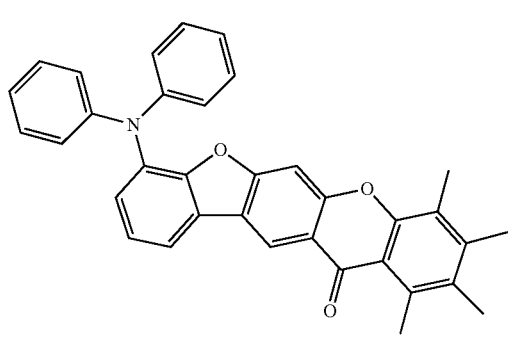
D-5
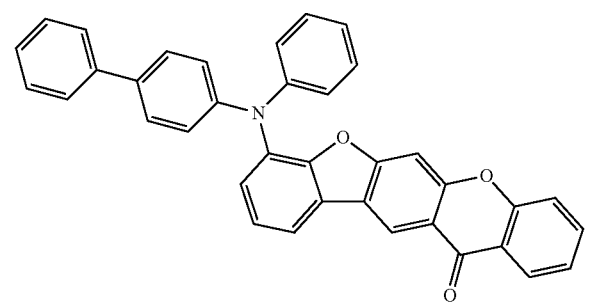
D-6
D-7
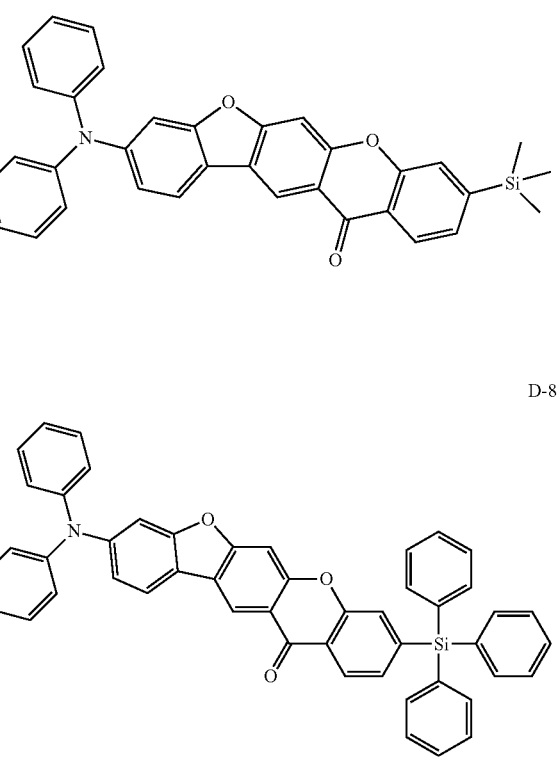
D-8

D-9
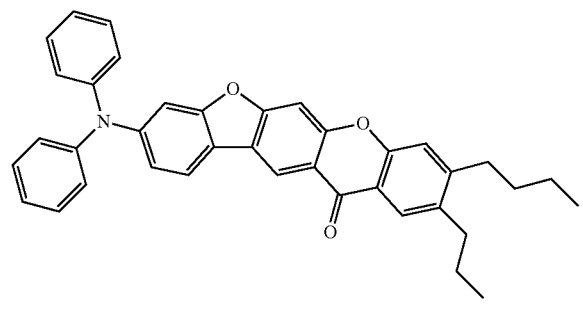
D-13
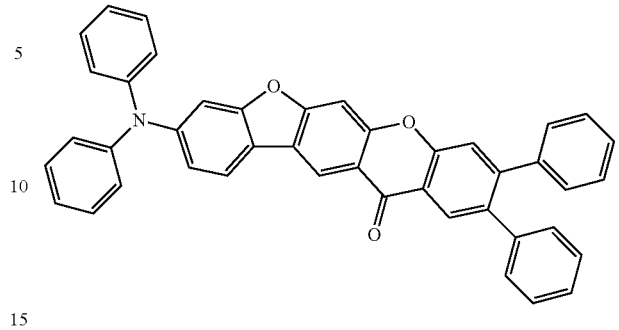
D-10
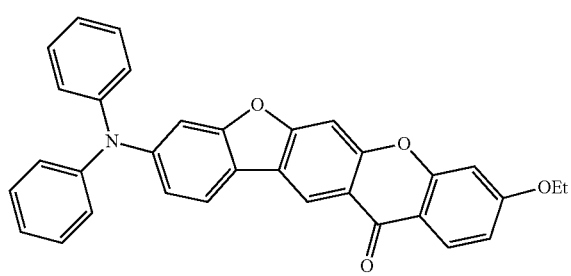
D-14
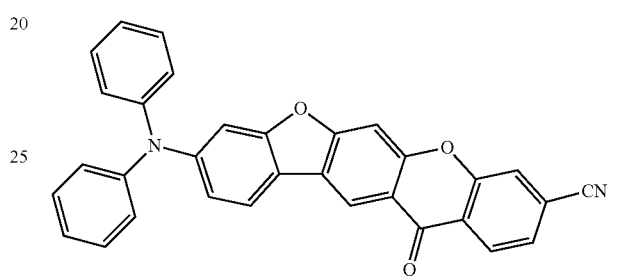
D-11
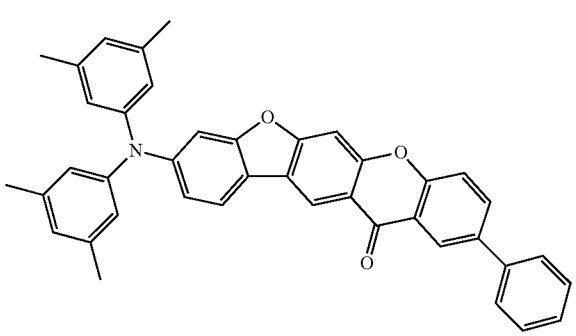
D-15
D-12
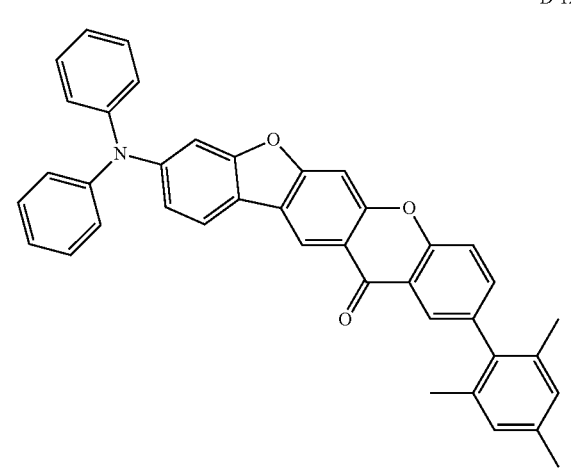
D-16
D-17
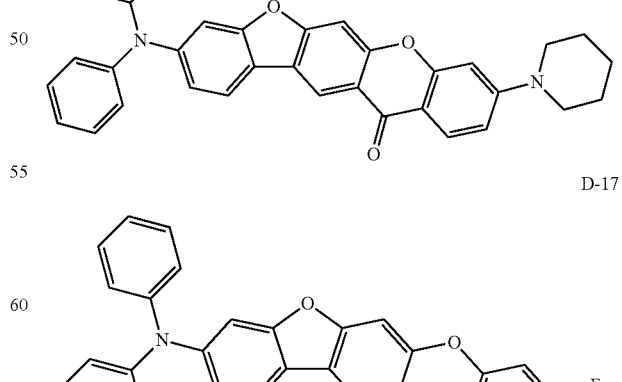

D-18
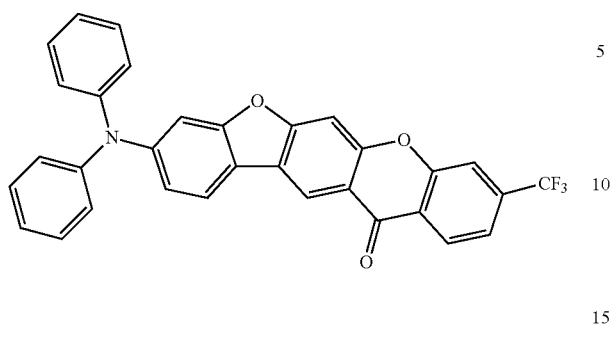
D-19
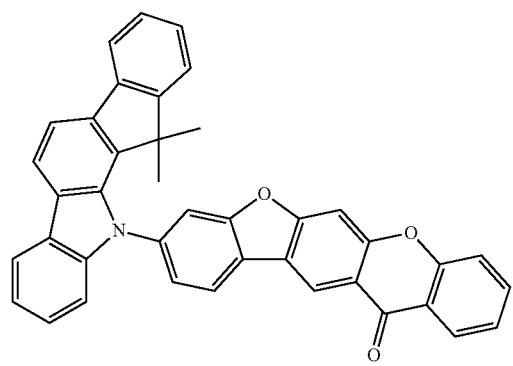
D-20
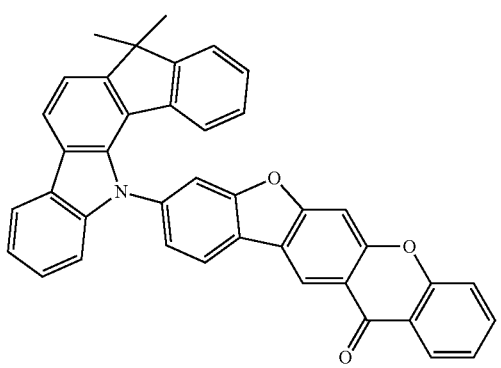
D-21
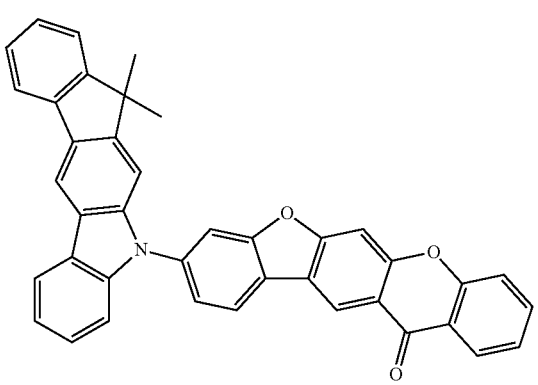
D-22
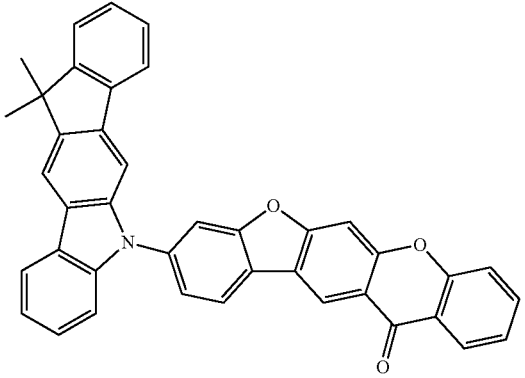
D-23
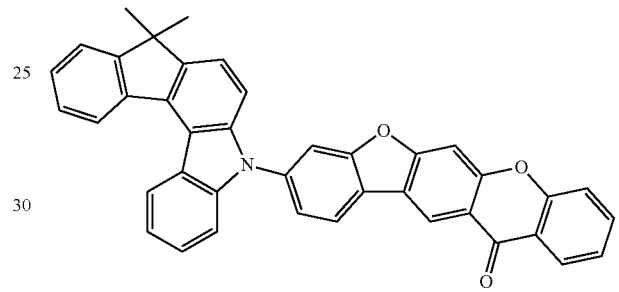
D-24
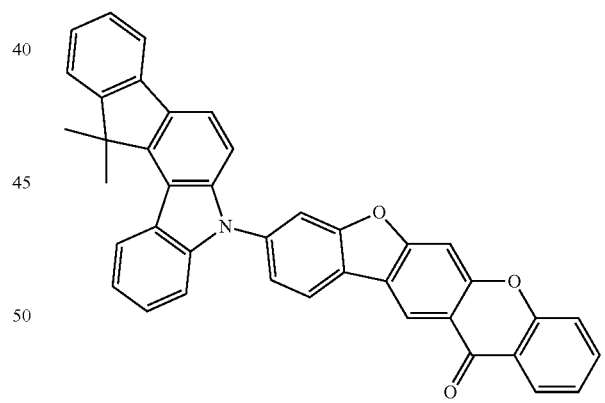
D-25
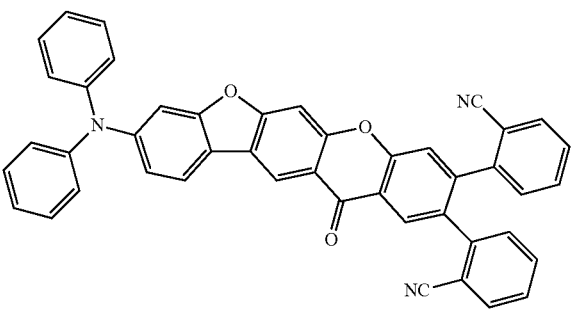

-continued
D-26
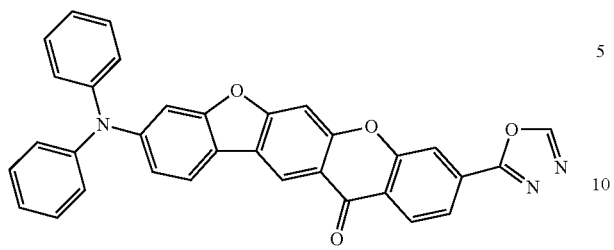
D-27
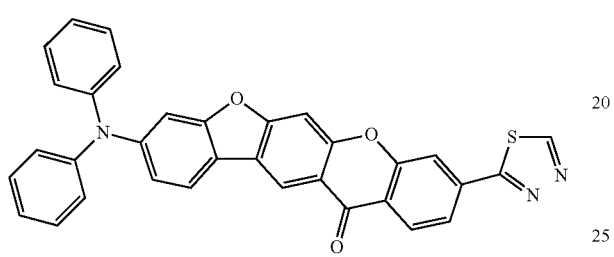
D-28
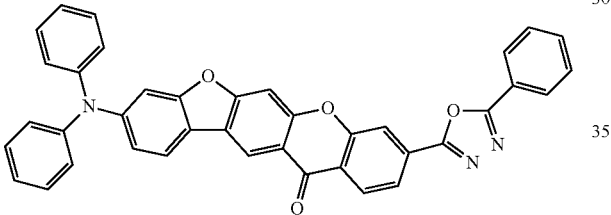
E-1
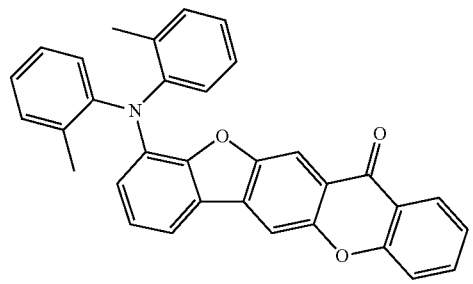
-continued
E-3
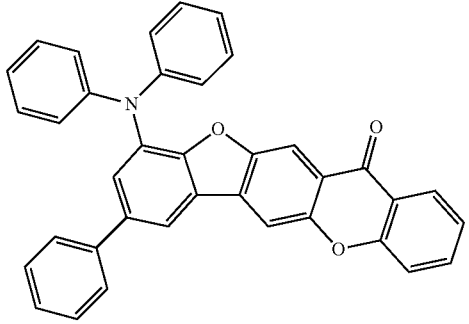
E-4
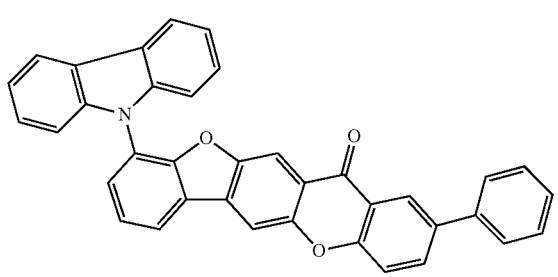
E-5
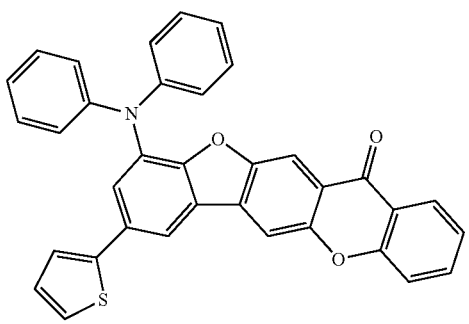
E-6
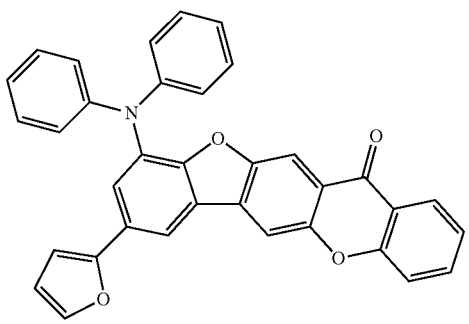
E-7
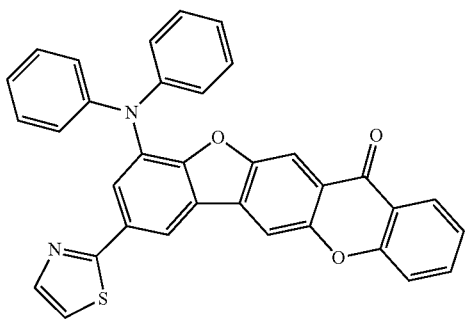
E-2

E-8
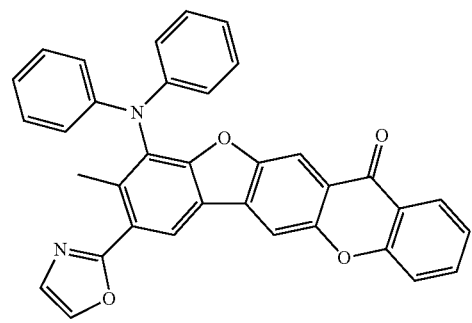
E-12
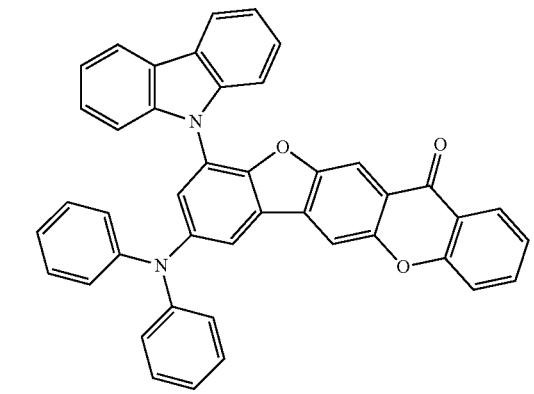
E-9
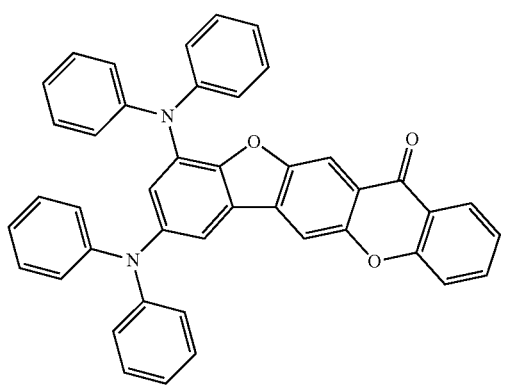
E-13
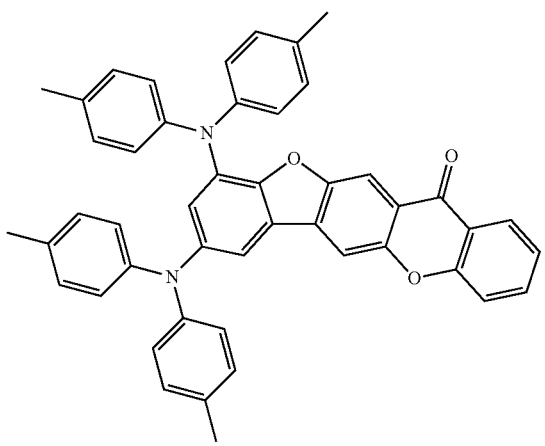
E-10
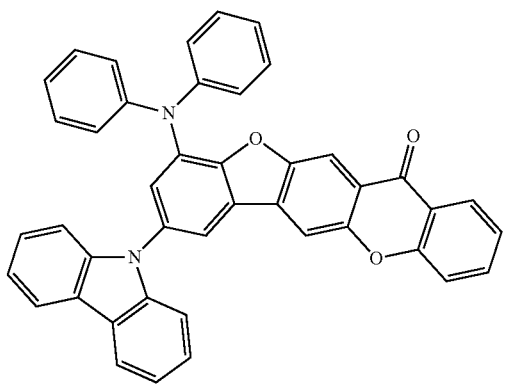
E-11
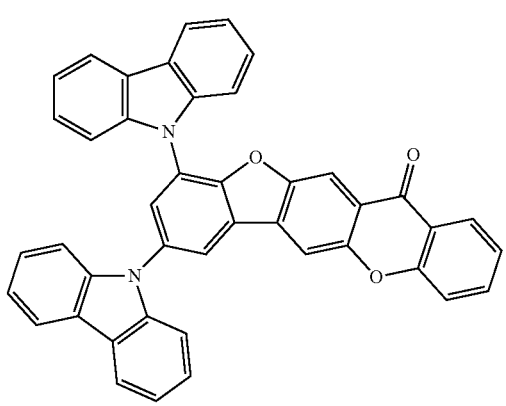
E-14
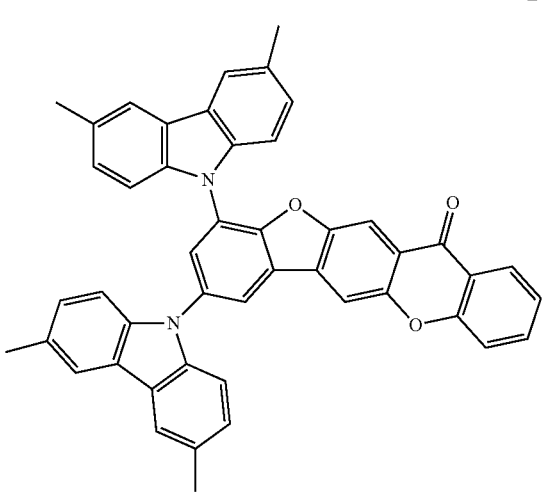

E-15
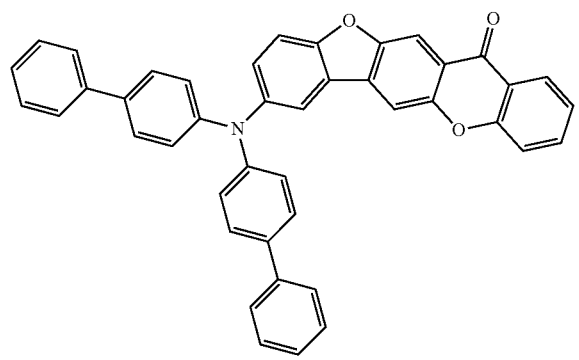
E-16
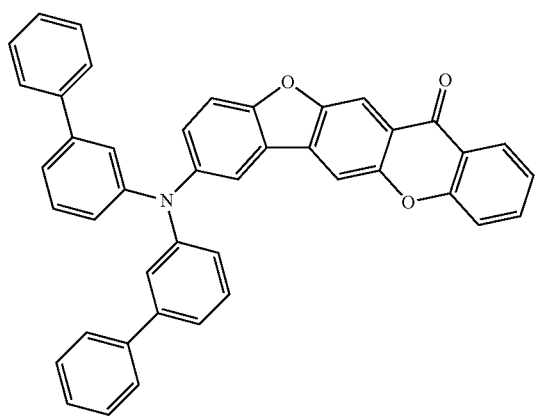
E-17
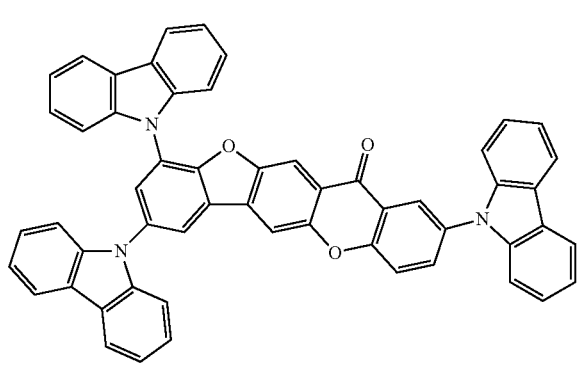
E-19
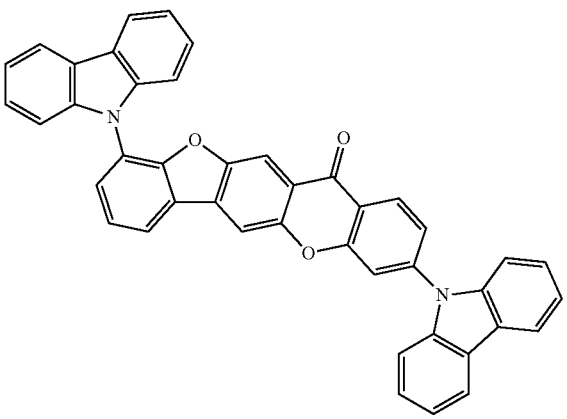
E-20
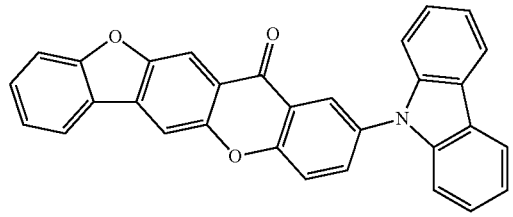
E-21
E-22
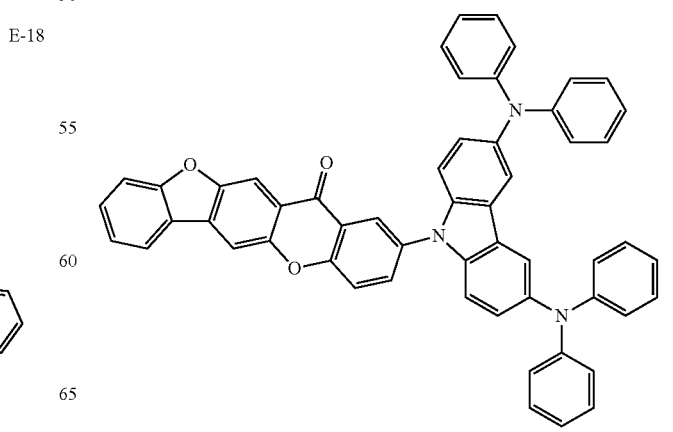

E-23
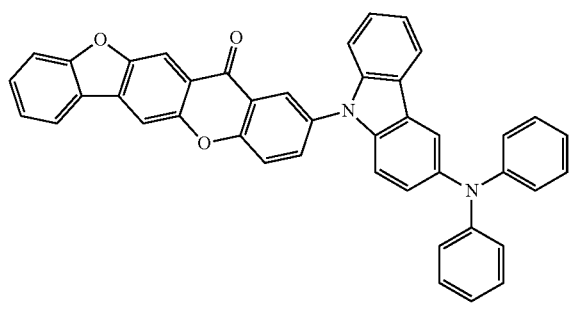
E-24
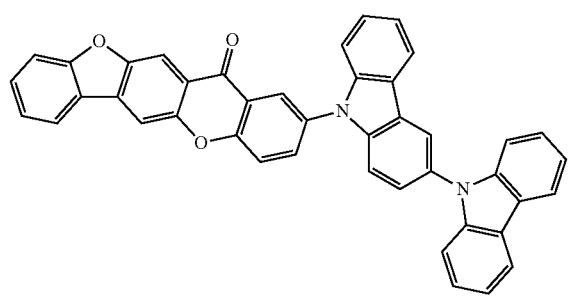
E-25
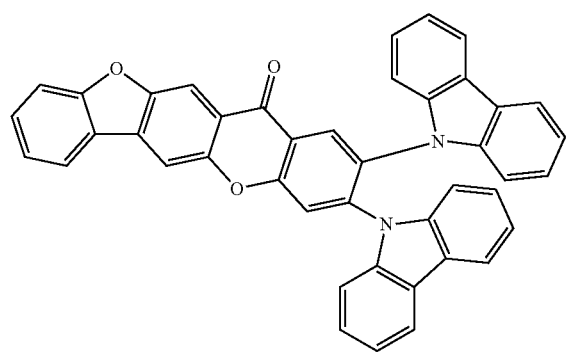
E-26
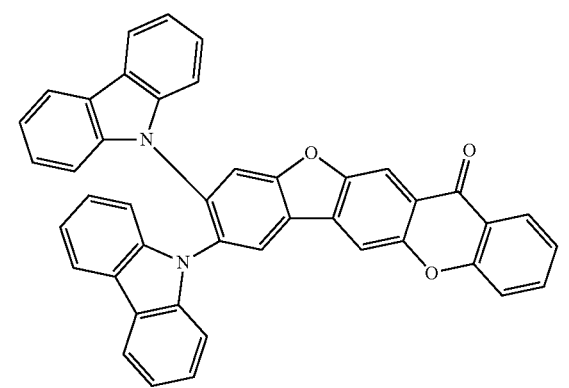
E-27
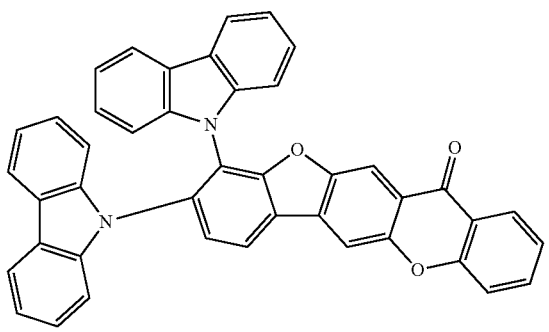
E-28
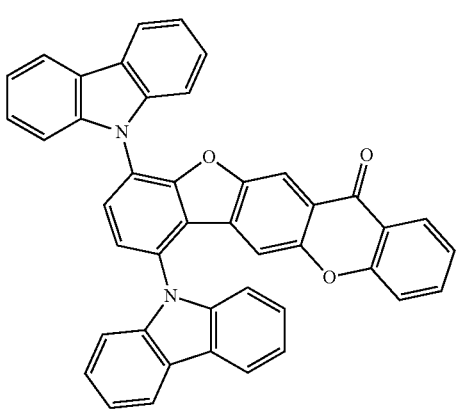
F-1
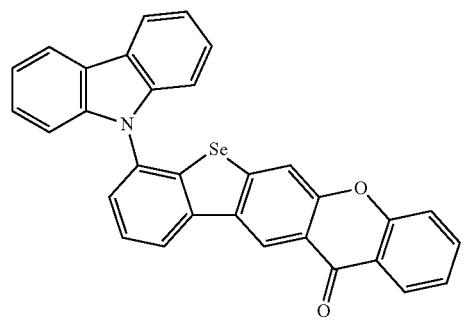
F-2
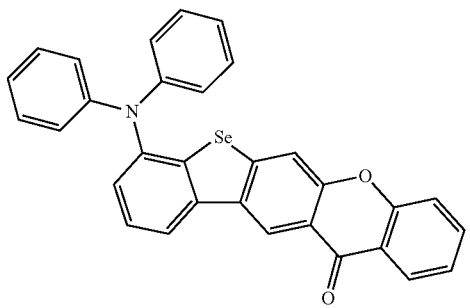

-continued
F-3
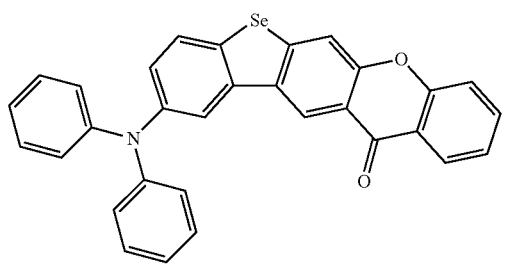
F-4
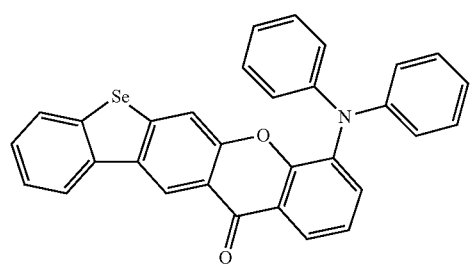
F-5
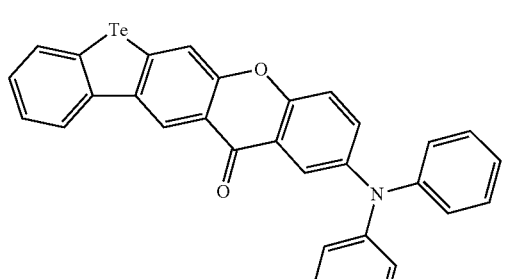
F-6
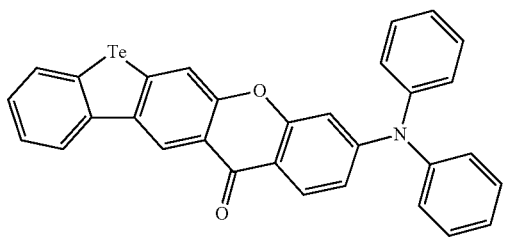
F-7
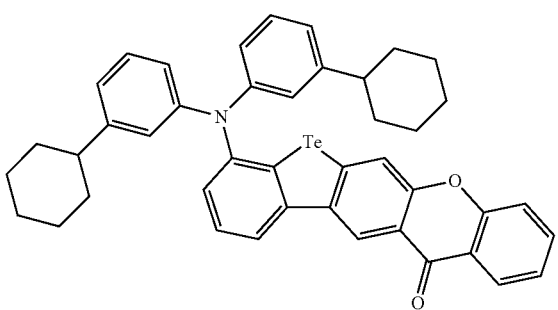
F-8
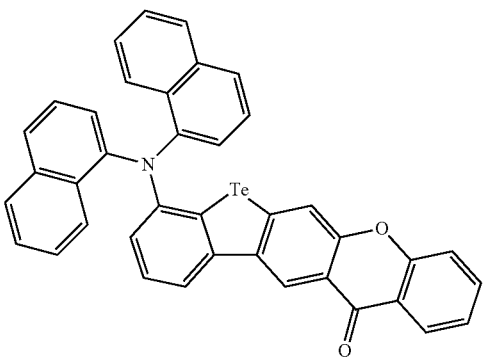
F-9
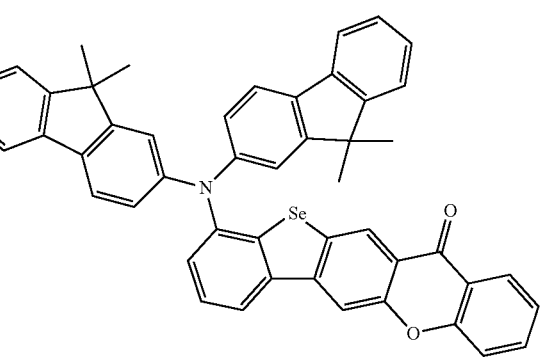
F-10
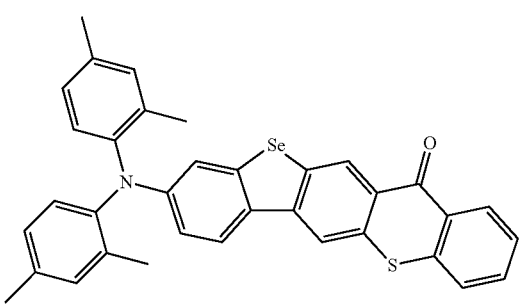
F-11
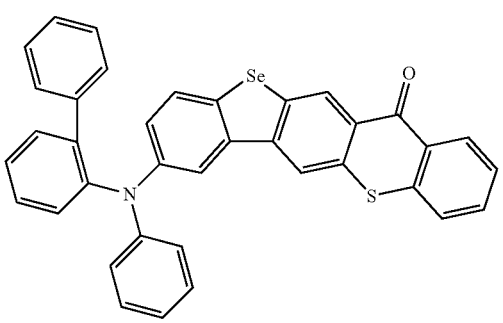

F-12
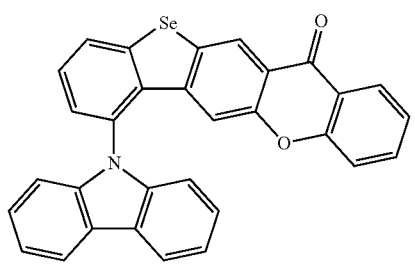
F-13
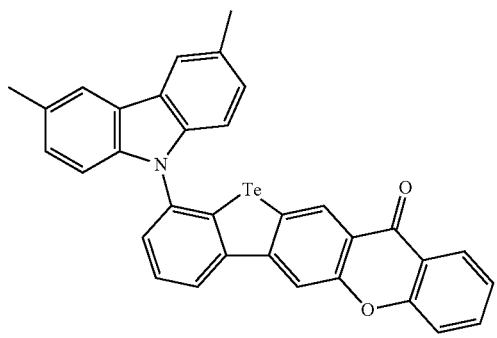
F-14
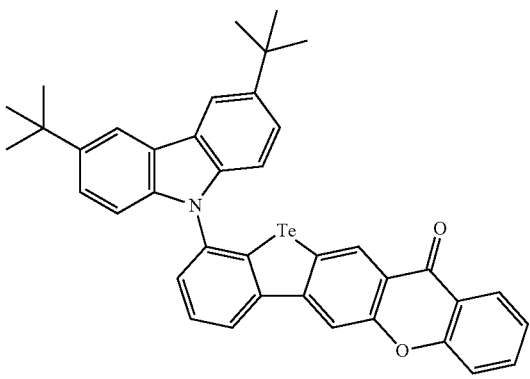
F-15
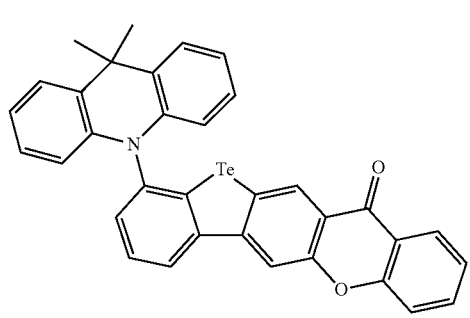
F-16
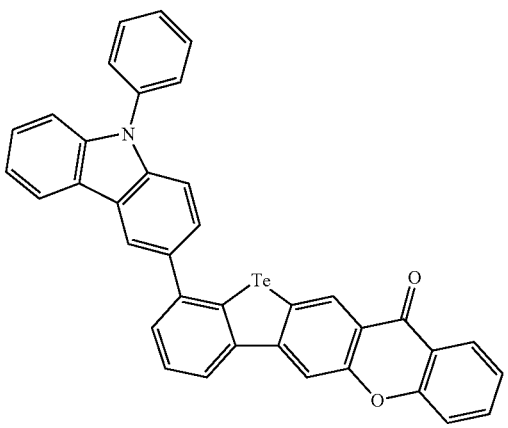
F-17
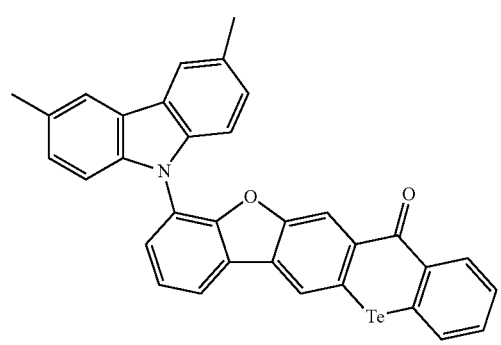
F-18
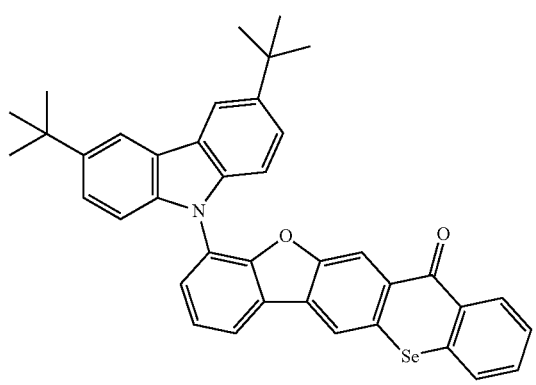
F-19
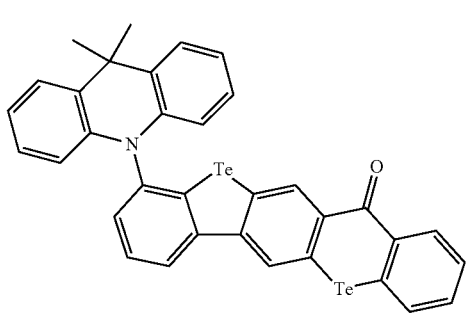

F-20
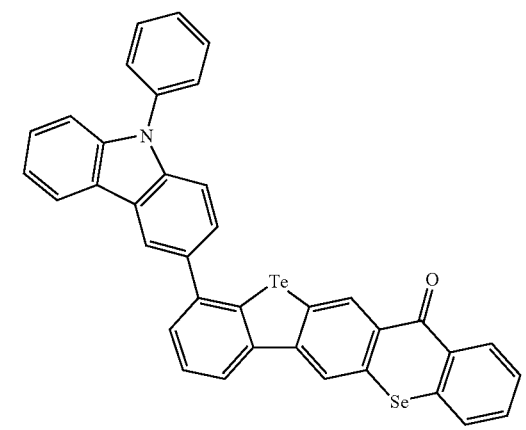
G-4
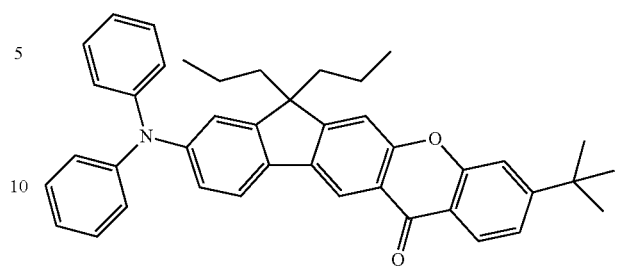
G-1
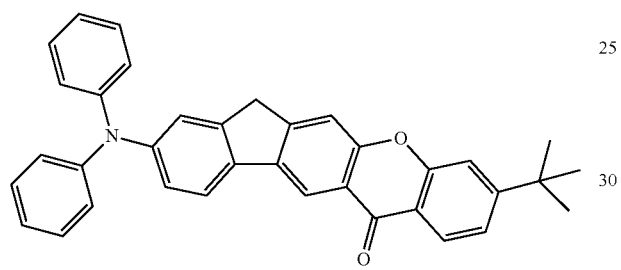
G-5
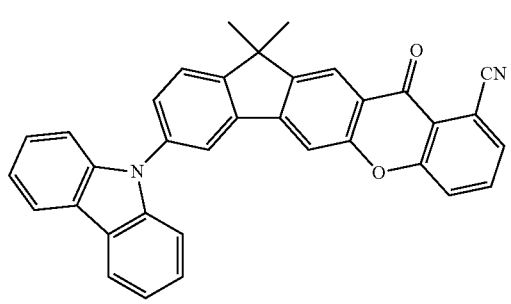
G-2
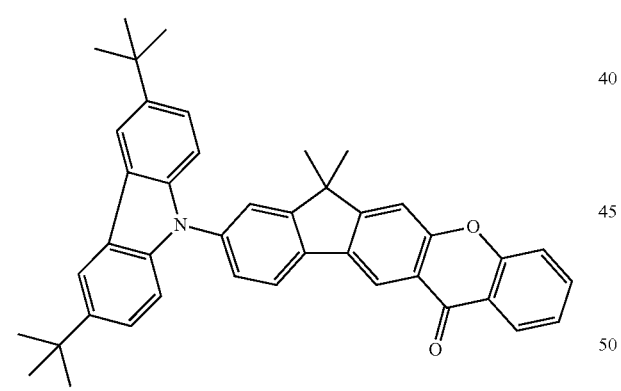
G-6
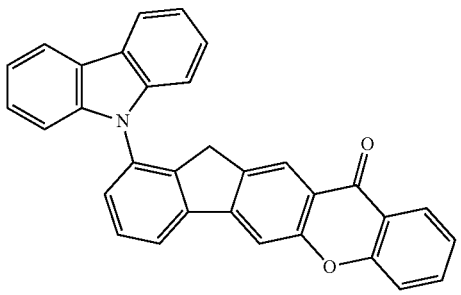
G-7
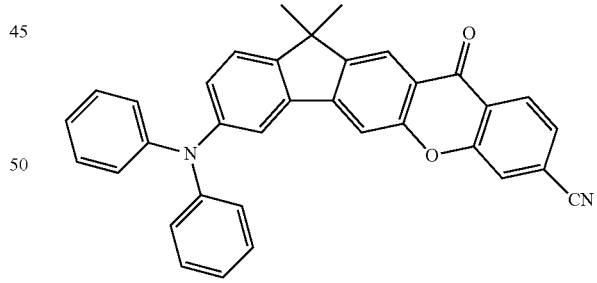
G-3
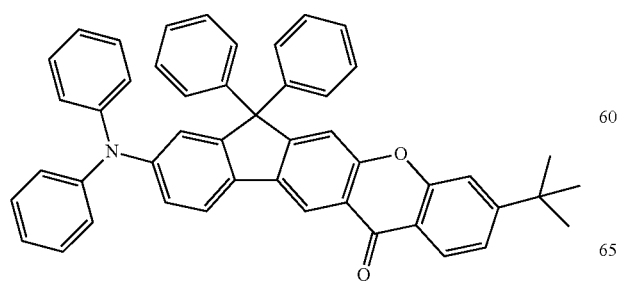
G-8
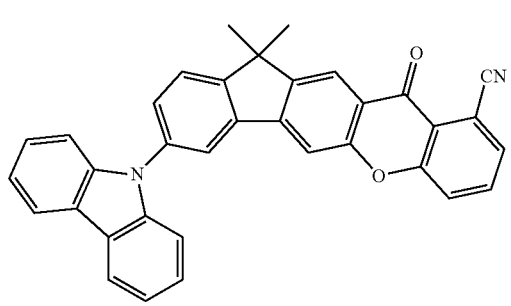

G-9
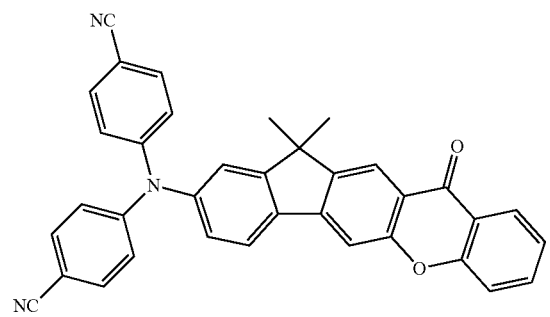
G-13
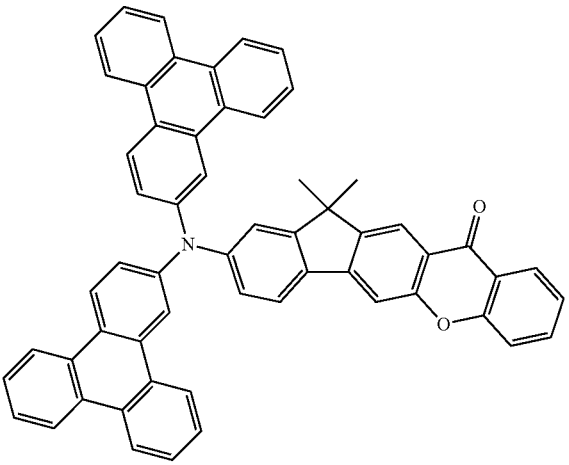
G-10
G-14
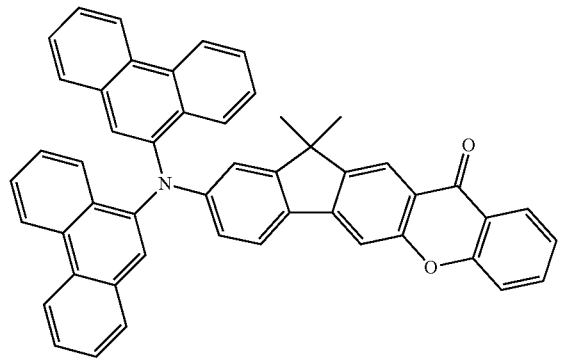
G-11
G-15
G-12
G-16
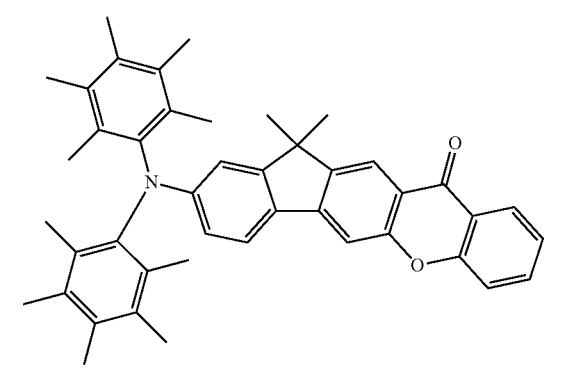
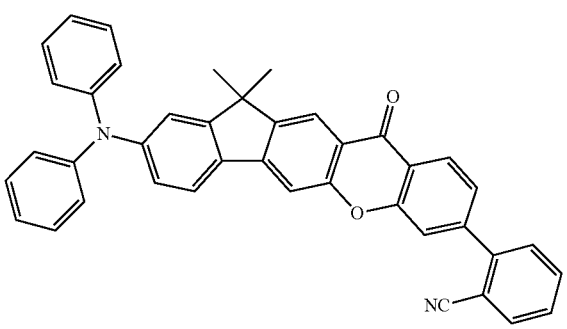

G-17
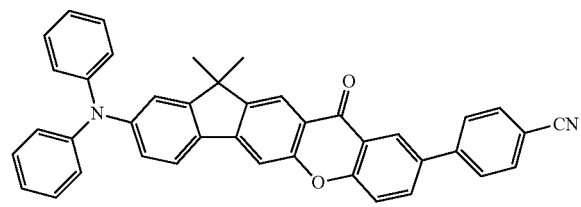
G-18
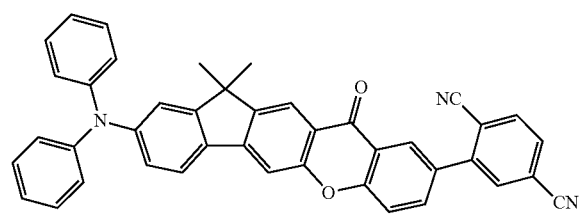
G-19
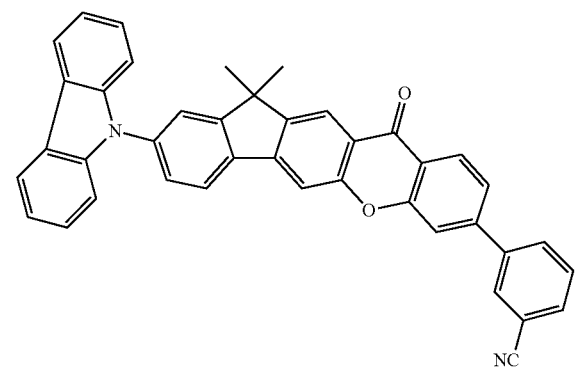
G-20
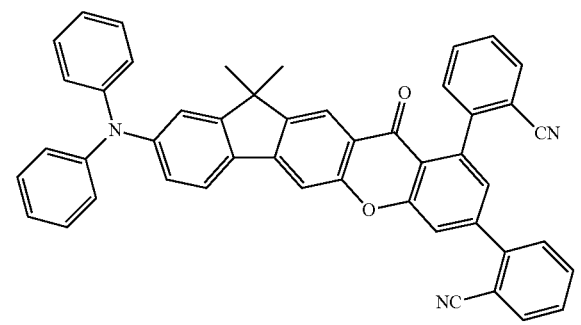
H-1
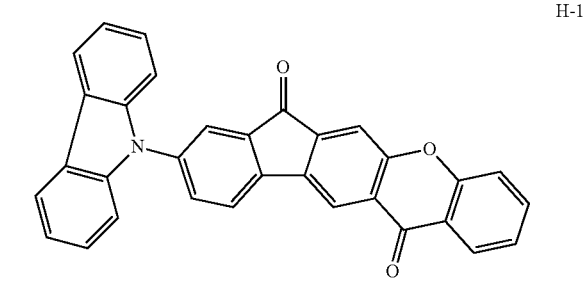
H-2
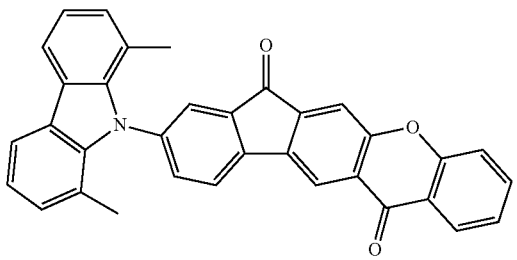
H-3
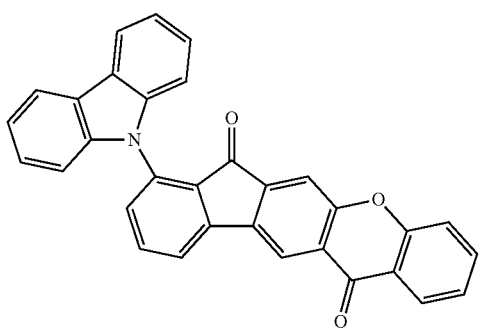
H-4
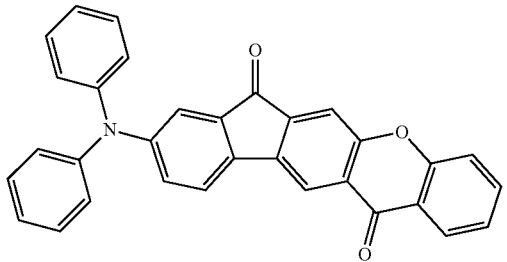
H-5
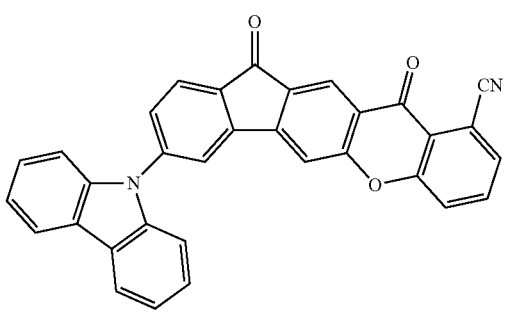
H-6
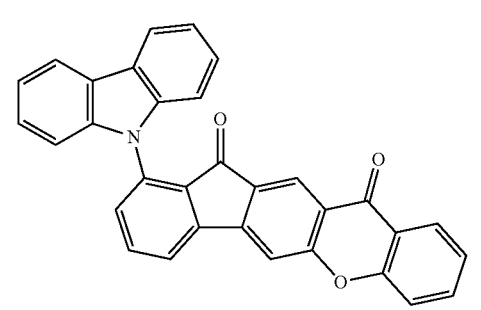

-continued
H-7
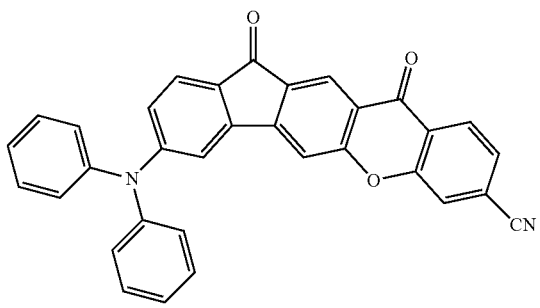
H-8
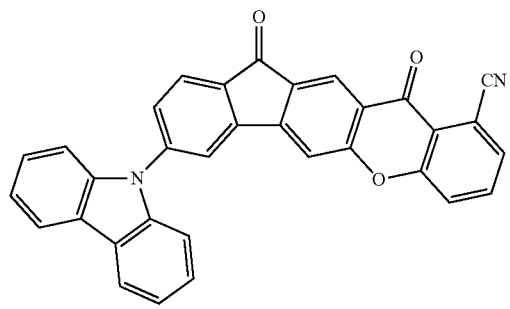
I-1
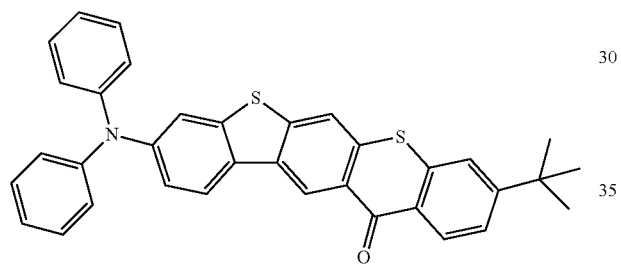
I-2
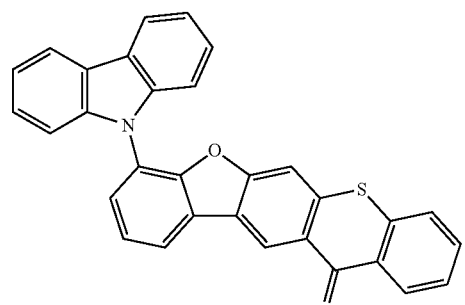
I-3
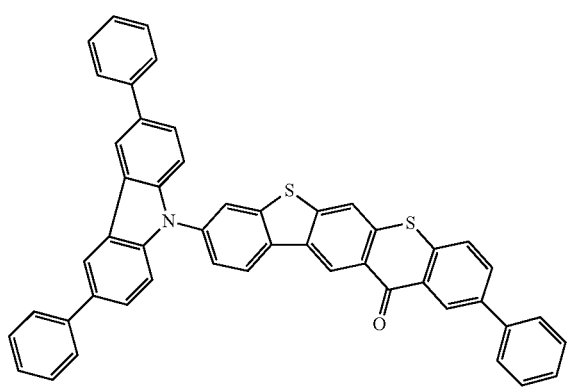
-continued
I-4
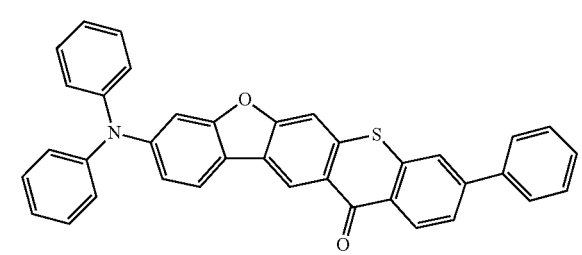
I-5
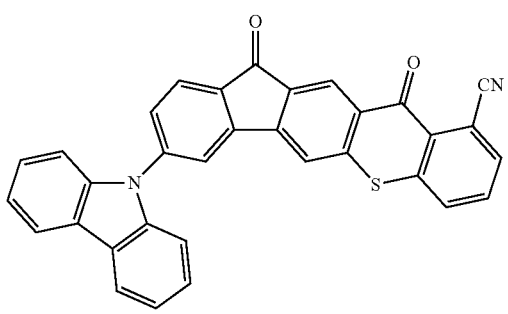
I-6
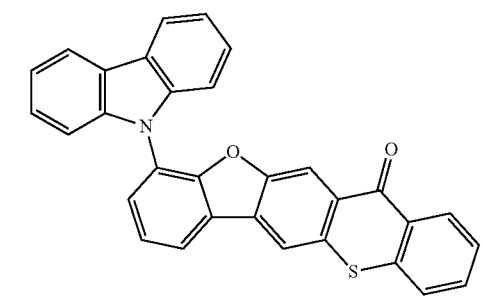
I-7
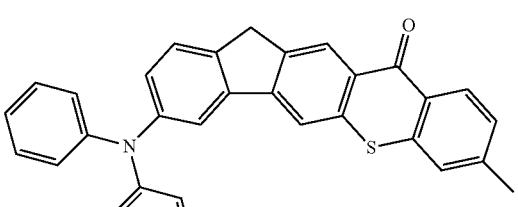
I-8
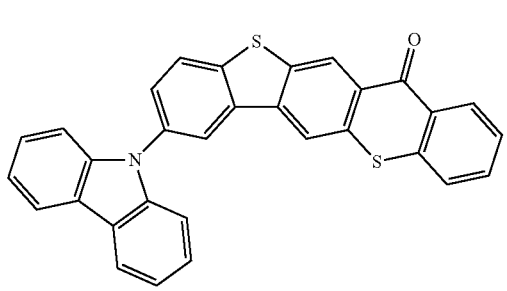

I-9
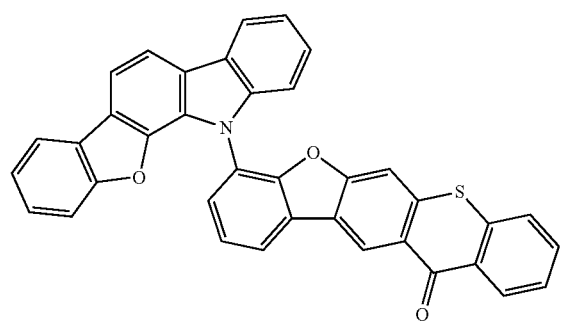
I-10
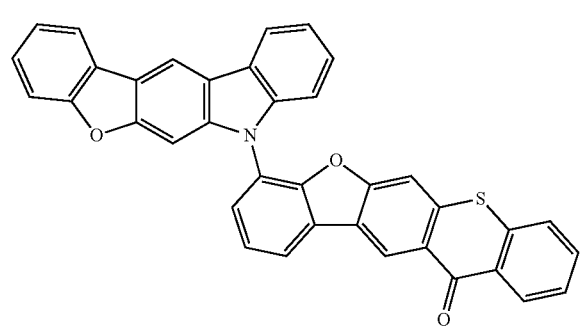
I-11
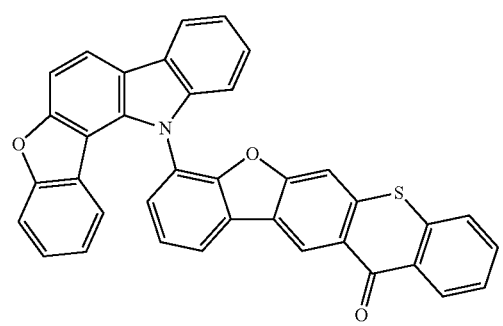
I-12
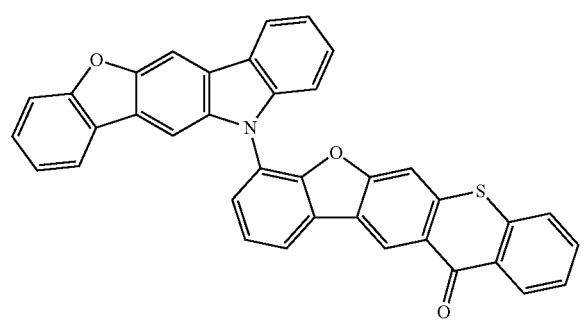
I-13
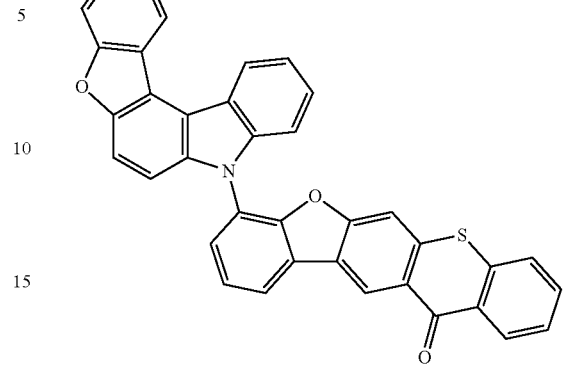
I-14
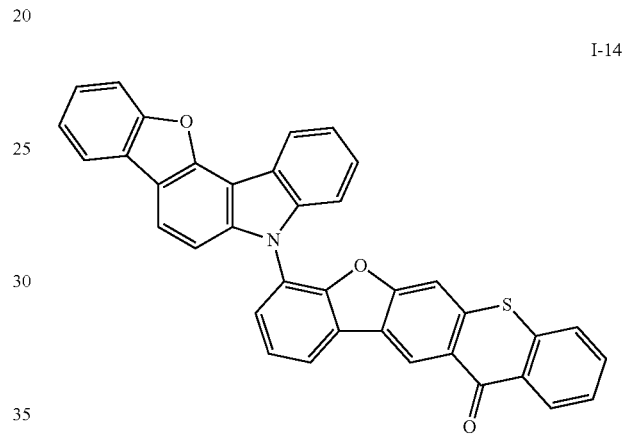
I-15
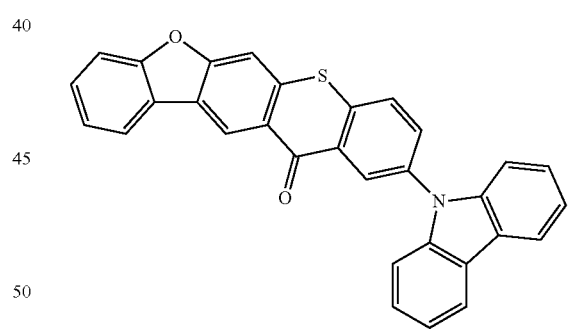
I-16
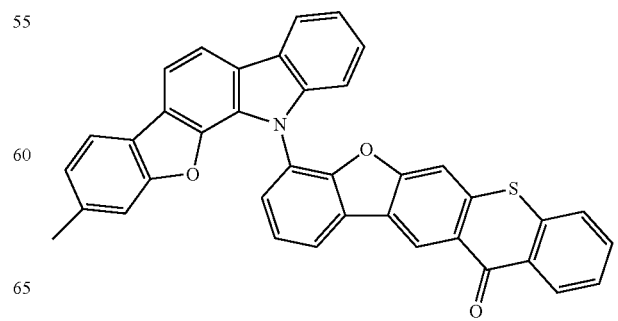

I-17

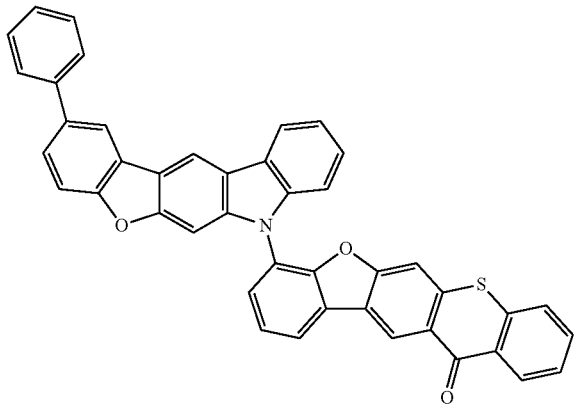

I-21

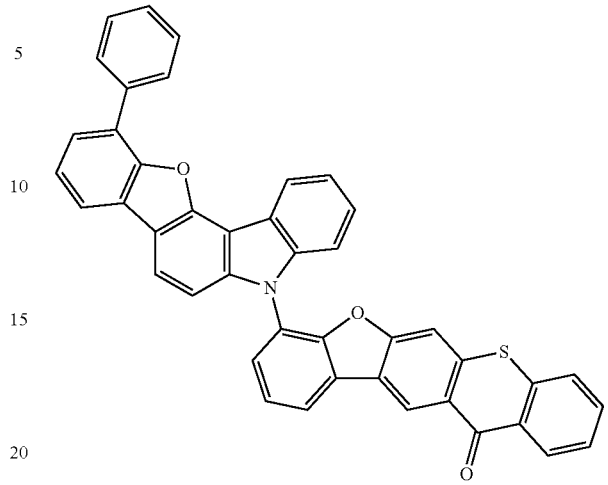

I-18

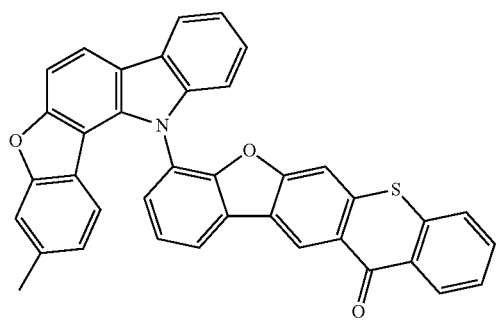

I-19

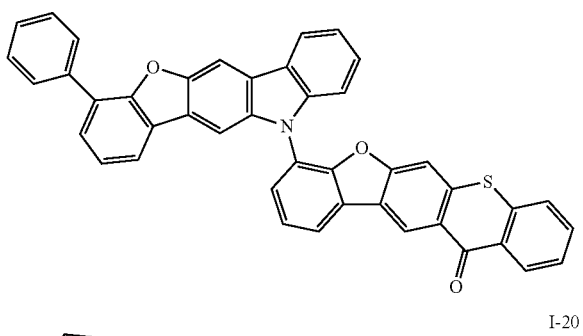

I-20

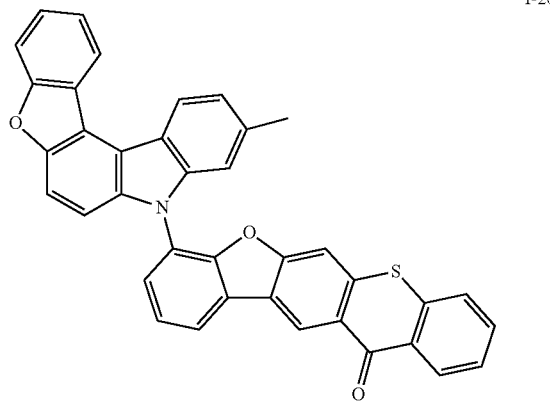

Compounds belonging to group B are each a compound in which $Y_1$ is sulfur and $Y_2$ is oxygen in the compound represented by formula [1]. Compounds belonging to group C are each a compound in which $Y_3$ is sulfur and $Y_4$ is oxygen in the compound represented by formula [2]. Since $Y_1$ and $Y_3$ are sulfur, the five-membered ring formed has a distorted structure, lowering the degree of flatness of the molecule. Thus, the concentration quenching is even less likely to occur.

Compounds belonging to group D are each a compound in which $Y_1$ and $Y_2$ are each oxygen in the compound represented by formula [1]. Compounds belonging to group E are each a compound in which $Y_3$ and $Y_4$ are each oxygen in the compound represented by formula [2]. Since $Y_1$ to $Y_4$ are each oxygen, a chemical reaction, such as oxidation, does not easily occur; thus, these chemically stable compounds are provided.

Compounds belonging to group F are each a compound in which at least one of $Y_1$ and $Y_2$ and at least one of $Y_3$ and $Y_4$ are each selenium or tellurium in the compound represented by formula [1] or [2]. Selenium and tellurium are each an element having a d-orbital and metallic properties; thus, the compounds belonging to group F have high electron mobility.

Compounds belonging to group G are each a compound in which $Y_1$ is a $CR_1R_2$ group and $Y_2$ is oxygen in the compound represented by formula [1] or in which $Y_3$ is a $CR_1R_2$ group and $Y_4$ is oxygen in the compound represented by formula [2]. In the compounds belonging to group G, when $R_1$ and $R_2$ are introduced, especially when $R_1$ and $R_2$ are groups other than hydrogen, the compounds are effective in reducing molecular association. Thus, the concentration quenching is even less likely to occur.

Compounds belonging to group H are each a compound in which $Y_1$ is a carbonyl group and $Y_2$ is oxygen in the compound represented by formula [1] or in which $Y_3$ is a carbonyl group and $Y_4$ is oxygen in the compound represented by formula [2]. Each compound belonging to group H has two carbonyl groups and thus has a higher electron-withdrawing ability. When the compound is mixed with the host material in the light-emitting layer, the compound is more likely to trap electrons to facilitate exciton recombination.

Compounds belonging to group I are each a compound in which $Y_1$ is oxygen, sulfur, a $CR_1R_2$ group, or a carbonyl group and $Y_2$ is sulfur in the compound represented by formula [1] or in which $Y_3$ is oxygen, sulfur, a $CR_1R_2$ group, or a carbonyl group and $Y_4$ is sulfur in the compound represented by formula [2]. In each of the compounds belonging to group 1, because the elemental radius of sulfur is large, the six-membered ring formed has a distorted structure, leading to a low degree of flatness of the molecule. Thus, the concentration quenching is even less likely to occur.

Organic Light-Emitting Device

The organic light-emitting device according to the embodiment will be described below.

The organic light-emitting device according to the embodiment at least includes an anode and a cathode, which are a pair of electrodes, and an organic compound layer disposed between these electrodes. In the organic light-emitting device according to the embodiment, the organic compound layer may be formed of a single layer or a multilayer stack including multiple layers, as long as it includes a light-emitting layer. In the case where the organic compound layer is formed of a multilayer stack including multiple layers, the organic compound layer may include, in addition to the light-emitting layer, a hole injection layer, a hole transport layer, an electron-blocking layer, a hole/exciton-blocking layer, an electron transport layer, an electron injection layer, and so forth. The light-emitting layer may be formed of a single layer or a multilayer stack including multiple layers.

In the organic light-emitting device according to the embodiment, at least one organic compound layer contains the organic compound according to the embodiment. Specifically, the organic compound according to the embodiment is contained in any of the light-emitting layer, the hole injection layer, the hole transport layer, the electron-blocking layer, the hole/exciton-blocking layer, the electron transport layer, the electron injection layer, and so forth described above. The organic compound according to the embodiment can be contained in the light-emitting layer. The light-emitting layer can emit green light or red light. The emission color is not limited thereto.

In the organic light-emitting device according to the embodiment, in the case where the organic compound according to the embodiment is contained in the light-emitting layer, the light-emitting layer may consist of only the organic compound according to the embodiment or may be composed of the organic compound according to the embodiment and another compound. In the case where the light-emitting layer is composed of the organic compound according to the embodiment and another compound, the organic compound according to the embodiment may be used as a host or a guest in the light-emitting layer. The organic compound may be used as an assist material that can be contained in the light-emitting layer. The term "host" used here refers to a compound having the highest proportion by mass in compounds constituting the light-emitting layer. The term "guest" refers to a compound that has a lower proportion by mass than the host in the compounds constituting the light-emitting layer and that is responsible for main light emission. The term "assist material" refers to a compound that has a lower proportion by mass than the host in the compounds constituting the light-emitting layer and that assists the light emission of the guest.

In the case where the organic compound according to the embodiment is used as a guest in the light-emitting layer, the concentration of the guest is preferably 0.01% or more by mass and 20% or less by mass, more preferably 1% or more by mass and 15% or less by mass, based on the entire light-emitting layer. In the case where the organic compound according to the embodiment is used as an assist material in the light-emitting layer, the concentration of the assist material is preferably 0.1% or more by mass and 45% or less by mass, more preferably 1% or more by mass and 30% or less by mass, based on the entire light-emitting layer.

In the case where the organic compound according to the embodiment is used as a guest in the light-emitting layer, a material having a higher LUMO level than the organic compound according to the embodiment (a material having a LUMO level closer to the vacuum level) can be used as a host. The reason for this is as follows: The organic compound according to the embodiment tends to have a low LUMO level. Thus, when a material having a higher LUMO level than the organic compound according to the embodiment is used as a host, the organic compound according to the embodiment can receive more electrons supplied to the host of the light-emitting layer.

In the case where the organic compound according to the embodiment is used as an assist material in the light-emitting layer, a material having a higher LUMO level than the organic compound according to the embodiment (a material having a LUMO level closer to the vacuum level) can be used as a guest. The reason for this is as follows: The organic compound according to the embodiment tends to have a low LUMO level. Thus, when a material having a higher LUMO level than the organic compound according to the embodiment is used as a light-emitting material (guest), the organic compound according to the embodiment receives more electrons supplied to the host of the light-emitting layer, and the assist material is responsible for exciton recombination. This enables efficient energy transfer to the light-emitting material (guest).

The inventors have conducted various studies and have found that when the organic compound according to the embodiment is used as a host, guest, or assist material of a light-emitting layer, especially as a guest of a light-emitting layer, a device that emits light with high efficiency and high luminance and that is extremely durable can be provided. The inventors have further found that when the organic compound according to the embodiment is used as an assist material in the light-emitting layer, a device that emits light with high efficiency and high luminance and that is extremely durable can be provided. The light-emitting layer may be formed of a single layer or multiple layers, and can contain multiple light-emitting materials. The term "multiple layers" may include a state in which the light-emitting layer and another light-emitting layer are stacked, or a state in which an intermediate layer is stacked between multiple light-emitting layers. Tandem devices or stacked devices are also acceptable. In these cases, the emission color of the organic light-emitting device is not limited to a single color. More specifically, the emission color may be white or an intermediate color. A film-forming method is vapor deposition or coating. Details will be described in examples below.

The organic compound according to the embodiment can be used as a constituent material of an organic compound layer other than the light-emitting layer included in the organic light-emitting device according to the embodiment. Specifically, the organic compound may be used as a constituent material of the electron transport layer, the electron injection layer, the hole transport layer, the hole injection layer, the hole blocking layer, and so forth.

For example, a hole injection compound, a hole transport compound, a compound to be used as a host, a light-emitting compound, an electron injection compound, or an electron transport compound, which is known and has a low or high molecular weight, can be used together with the organic compound according to the embodiment, as needed. Examples of these compounds will be described below.

As a hole injection-transport material, a material having a high hole mobility can be used so as to facilitate the injection of holes from the anode and to transport the injected holes to the light-emitting layer. To reduce a deterioration in film quality, such as crystallization, in the organic light-emitting device, a material having a high glass transition temperature can be used. Examples of a low- or high-molecular-weight material having the ability to inject and transport holes include triarylamine derivatives, aryl carbazole derivatives, phenylenediamine derivatives, stilbene derivatives, phthalocyanine derivatives, porphyrin derivatives, poly(vinyl carbazole), polythiophene, and other conductive polymers. Moreover, the hole injection-transport material can be used for the electron-blocking layer. Non-limiting specific examples of a compound used as the hole injection-transport material will be illustrated below.

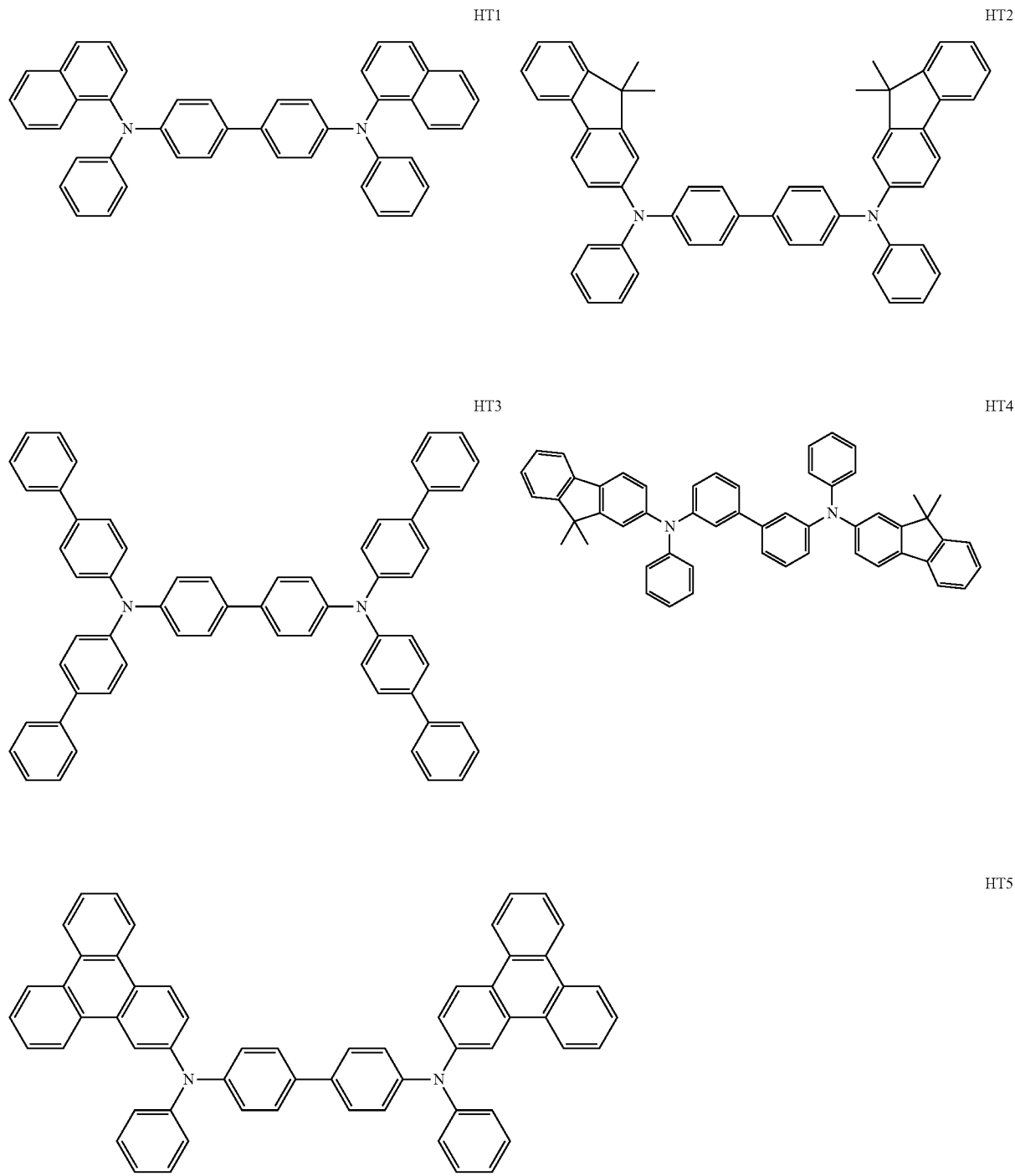

-continued
HT6
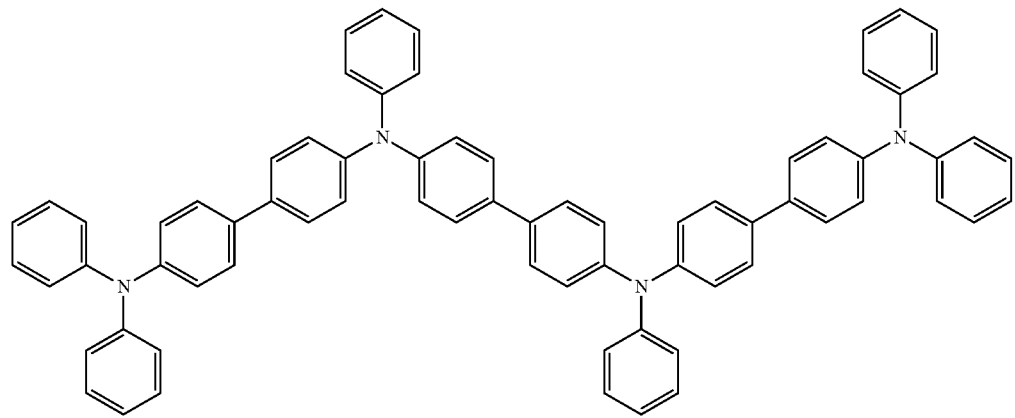
HT7
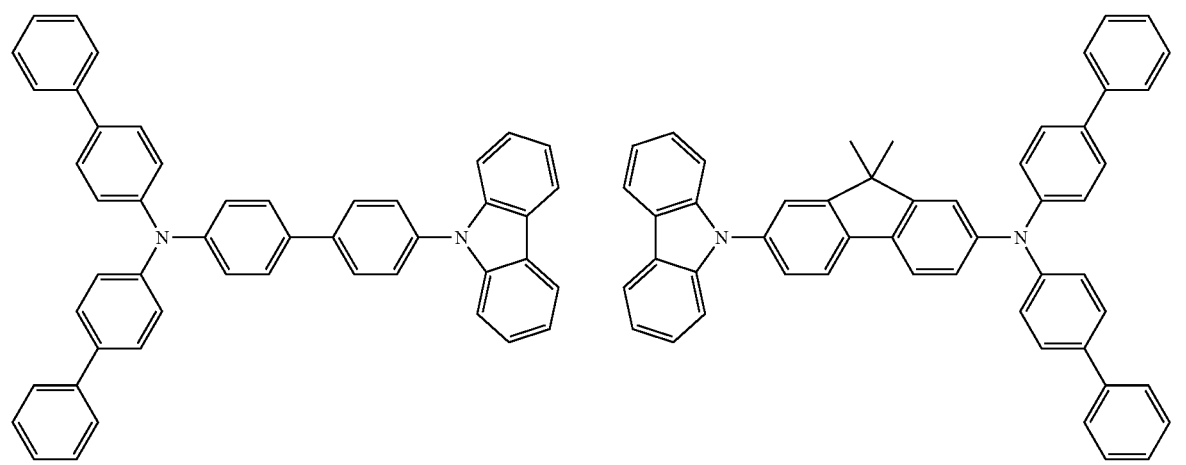
HT8
HT9
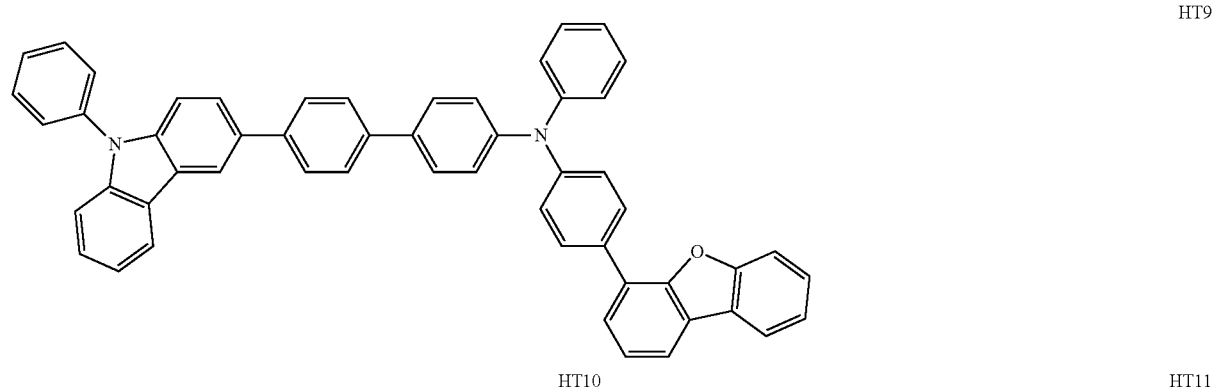
HT10
HT11
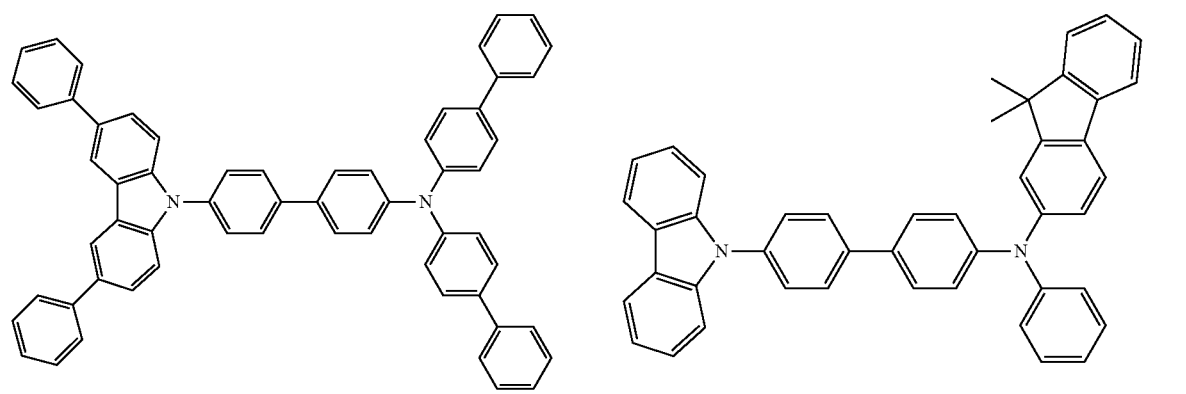

-continued
HT12
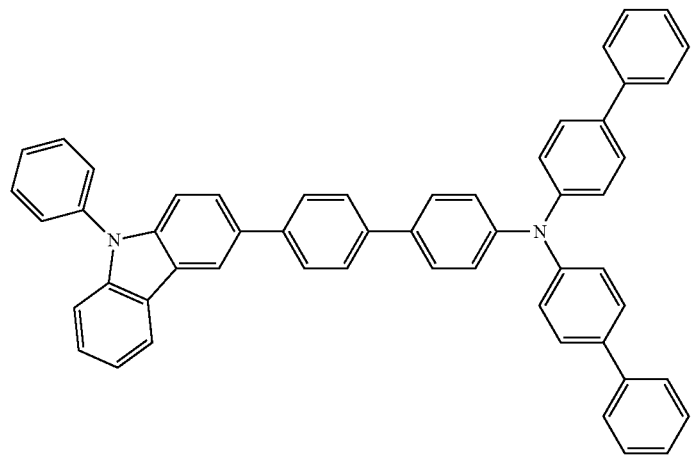
HT13
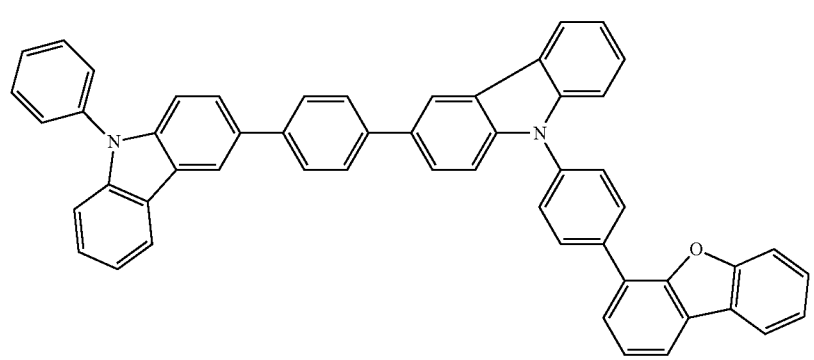
HT14
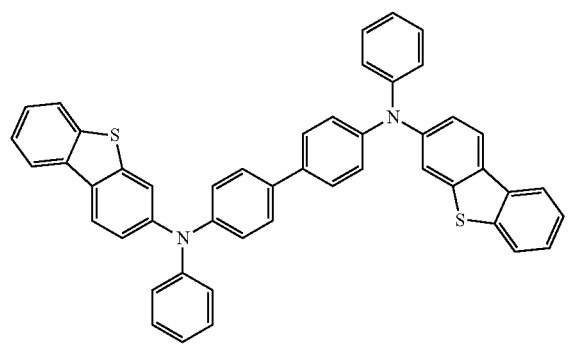
HT15
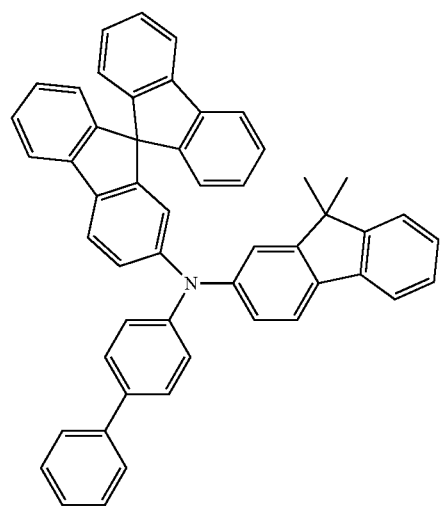
HT16
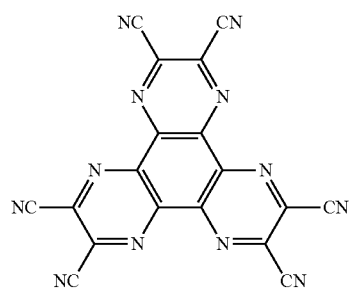
HT17
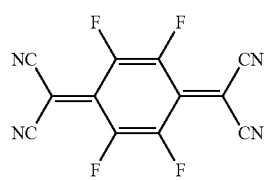

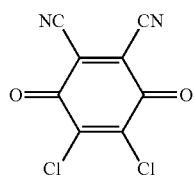

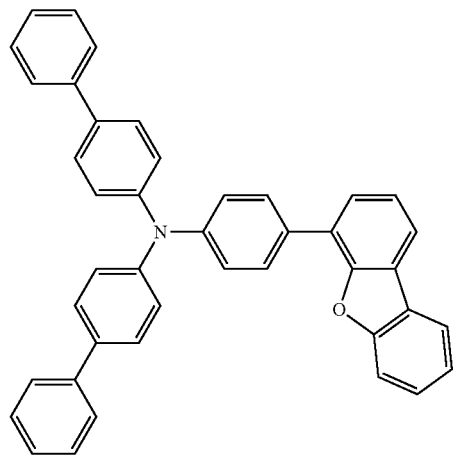

HT18

HT19

Among the hole transport materials illustrated above, HT16 to HT18 can be used in the layer in contact with the anode to reduce the driving voltage. HT16 is widely used in organic light-emitting devices. HT2, HT3, HT4, HT5, HT6, HT10, and HT12 may be used in an organic compound layer adjacent to HT16. Multiple materials may be used in a single organic compound layer.

Examples of a light-emitting material mainly associated with a light-emitting function include, in addition to the organic compounds represented by formulae [1] and [2], fused-ring compounds, such as fluorene derivatives, naphthalene derivatives, pyrene derivatives, perylene derivatives, tetracene derivatives, anthracene compounds, and rubrene, quinacridone derivatives, coumarin derivatives, stilbene derivatives, organoaluminum complexes, such as tris(8-quinolinolato)aluminum, iridium complexes, platinum complexes, rhenium complexes, copper complexes, europium complexes, ruthenium complexes, and polymer derivatives, such as poly(phenylene vinylene) derivatives, polyfluorene derivatives, and polyphenylene derivatives. Non-limiting specific examples of a compound used as a light-emitting material are illustrated below.

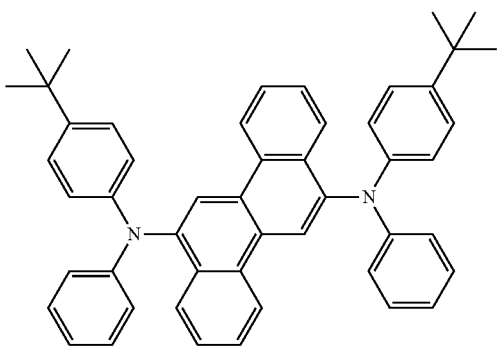

BD1

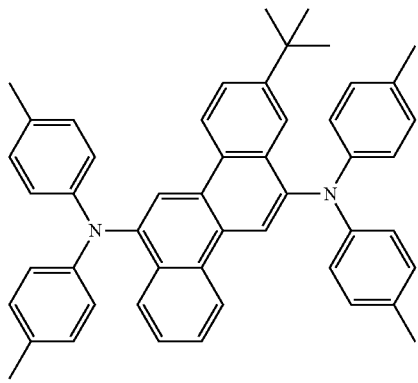

BD2

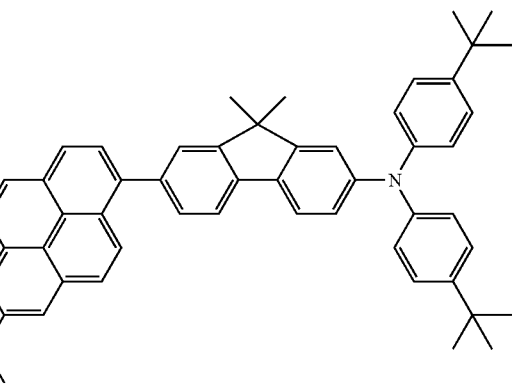

BD3

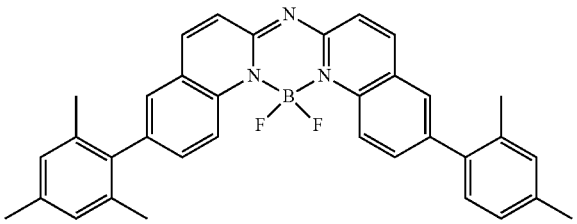

BD4

BD5
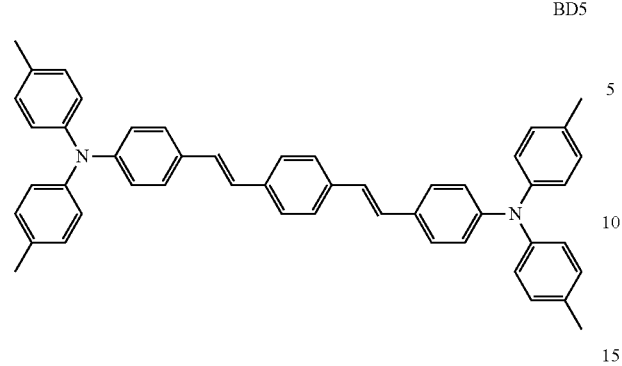
BD9
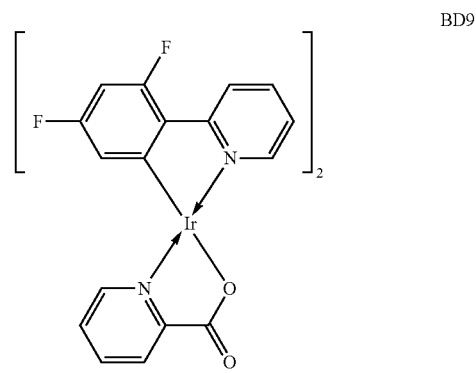
BD6
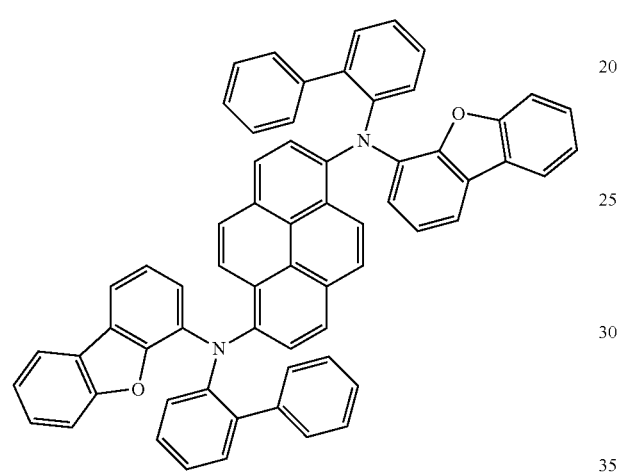
BD10
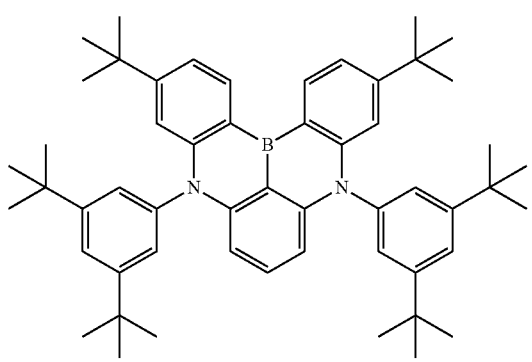
BD7
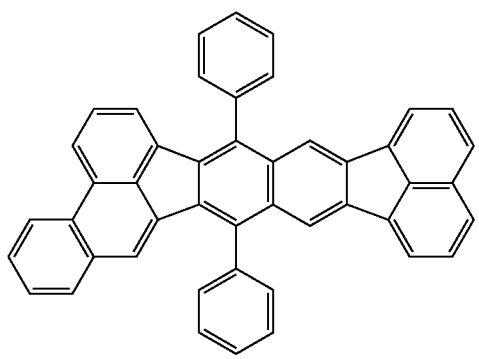
GD1
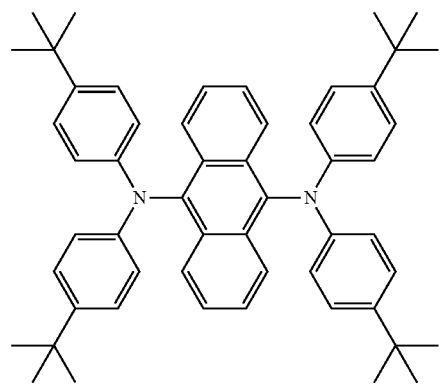
BD8
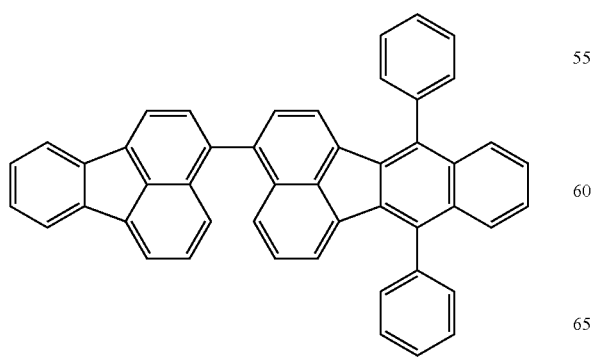
GD2
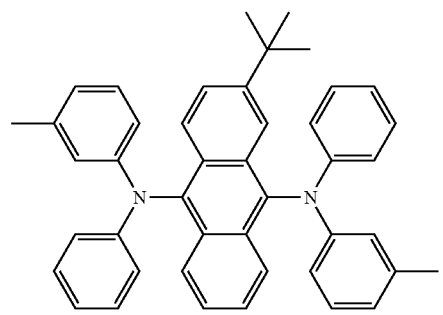

GD3
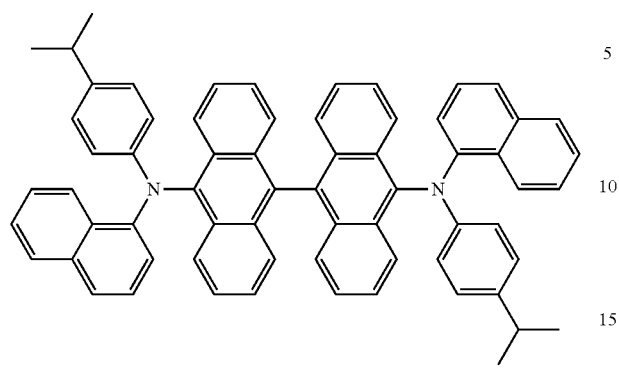
GD4
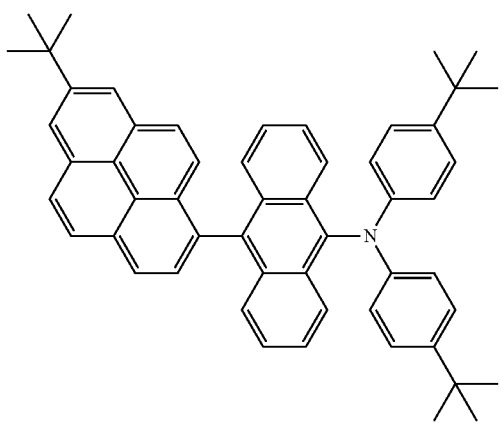
GD5
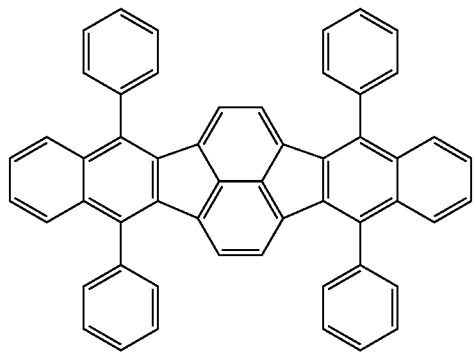
GD6
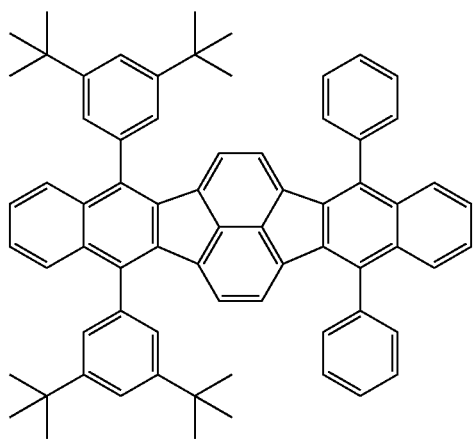
GD7
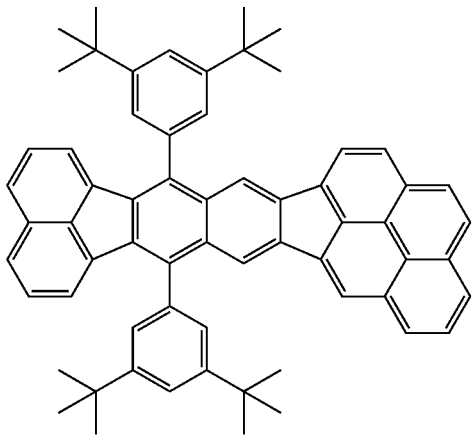
GD8
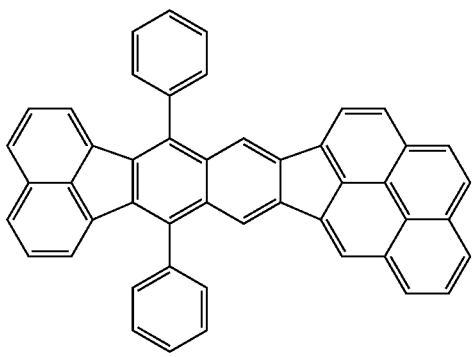
GD9
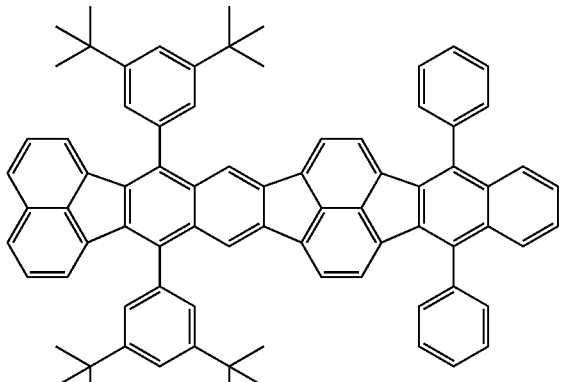
GD10
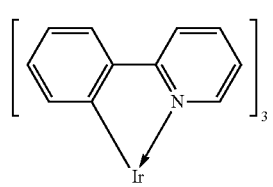

GD11
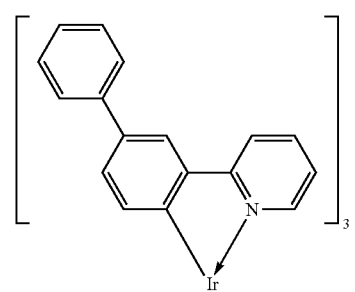
GD12
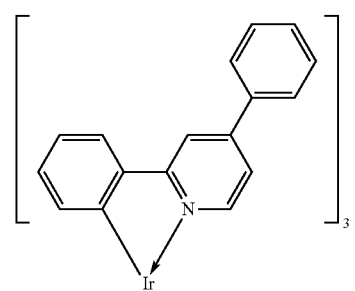
GD13
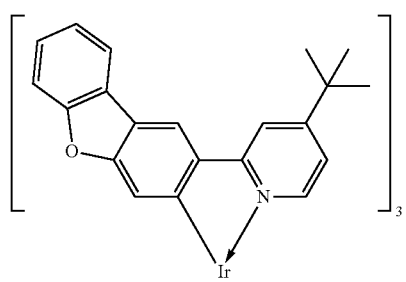
GD14
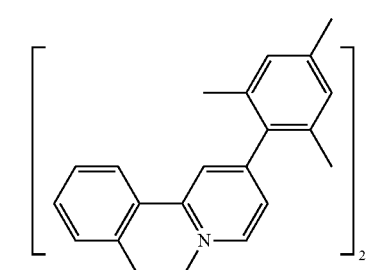
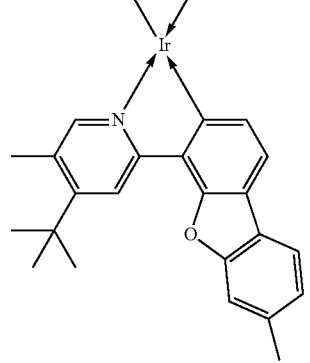
GD15
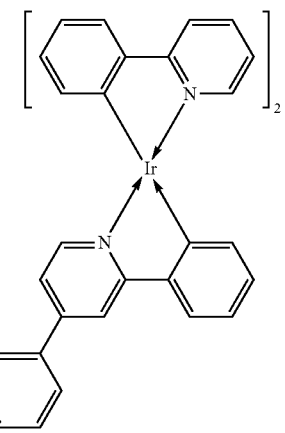
RD1
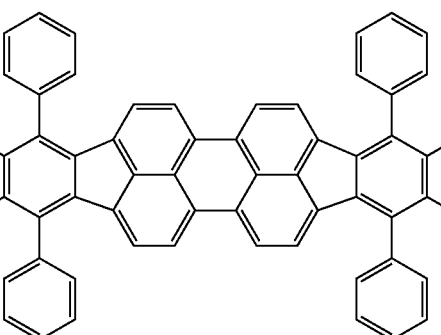
RD2
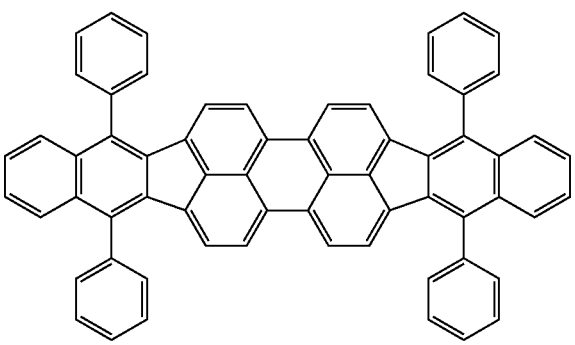
RD3
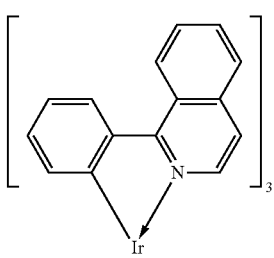

RD4

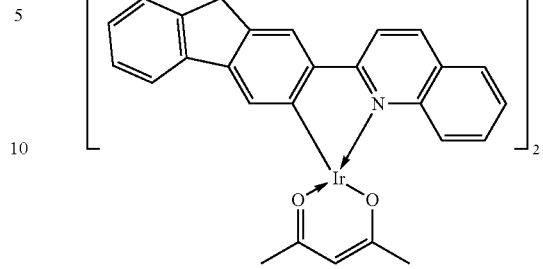

RD5

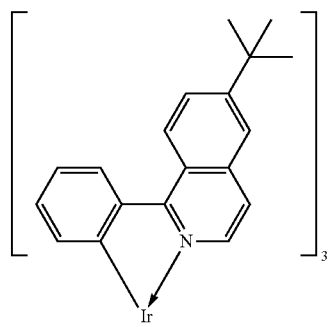

RD8

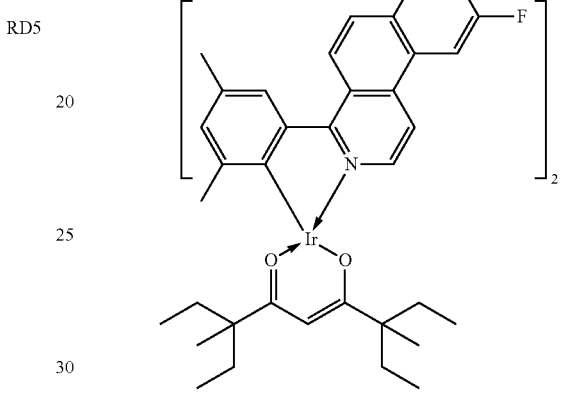

RD9

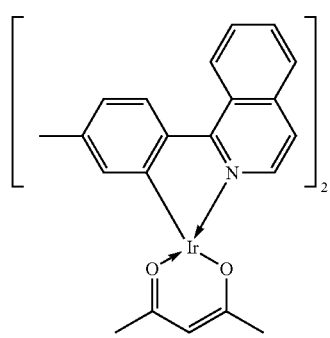

RD6

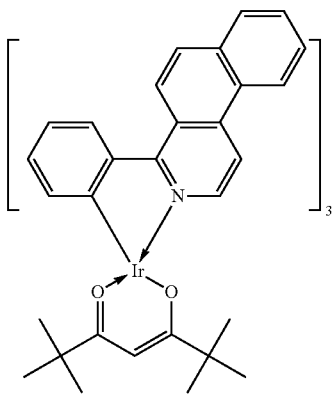

RD10

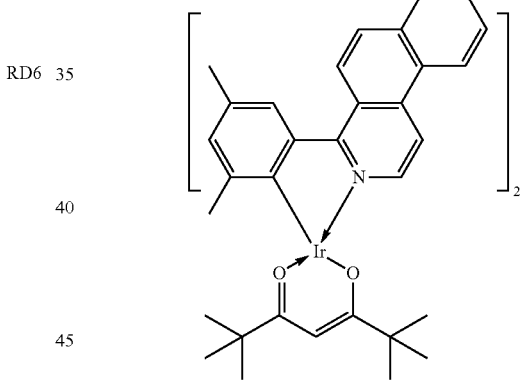

RD7

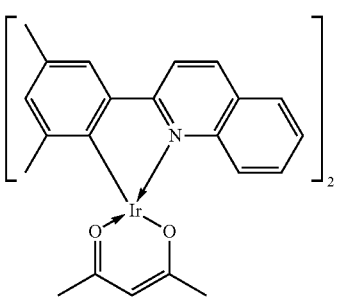

When the light-emitting material is a hydrocarbon compound, the material can prevent a decrease in luminous efficiency due to exciplex formation and a deterioration in color purity due to a change in the emission spectrum. The term "hydrocarbon compound" refers to a compound consisting of only carbon and hydrogen, and BD7, BD8, GD5 to GD9, and RD1 are hydrocarbon compounds. When the light-emitting material is a five-membered ring-containing fused polycyclic compound, the material has a high ionization potential and high resistance to oxidation. This can provide a highly durable device with a long lifetime. BD7, BD8, GD5 to GD9, and RD1 are five-membered ring-containing fused polycyclic compounds.

Examples of a host or an assist material in the light-emitting layer include aromatic hydrocarbon compounds and derivatives thereof, carbazole derivatives, dibenzofuran derivatives, dibenzothiophene derivatives, organoaluminum complexes, such as tris(8-quinolinolato)aluminum, and organoberyllium complexes. Non-limiting specific examples of a compound used as a host or an assist material in the light-emitting layer will be illustrated below.

EM1
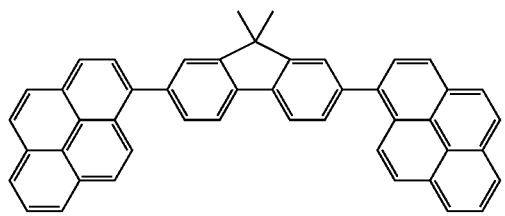
EM2
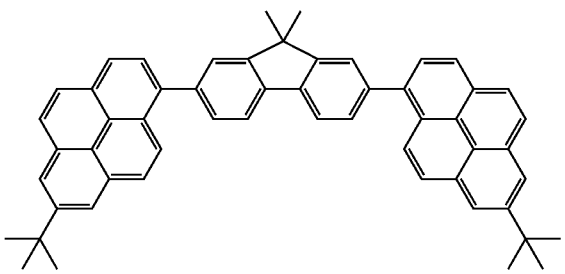
EM3
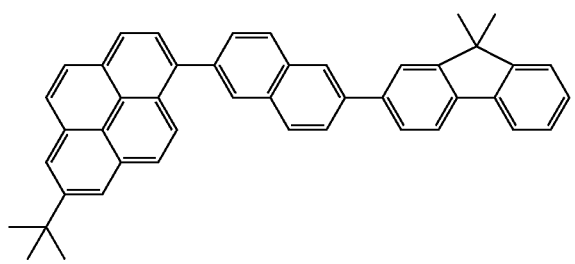
EM4
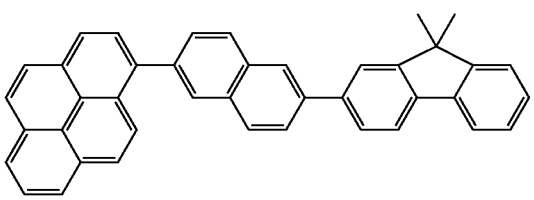
EM5
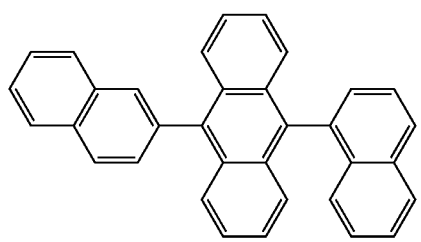
EM6
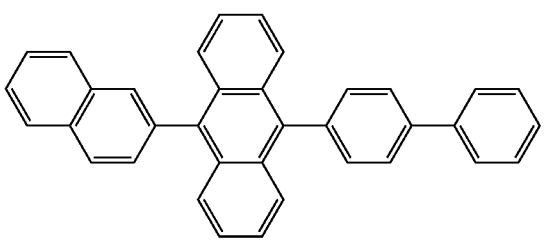
EM7
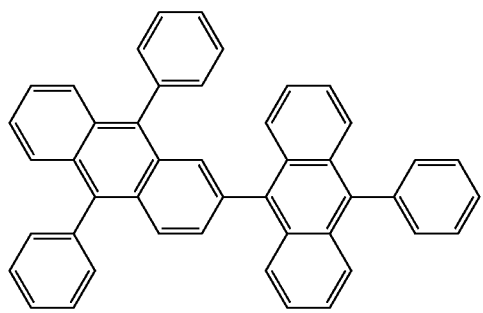
EM8
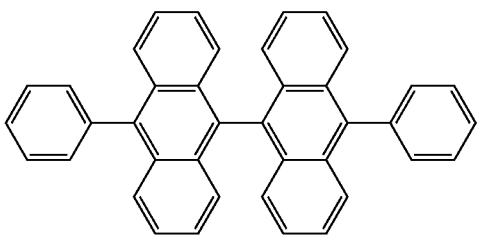
EM9
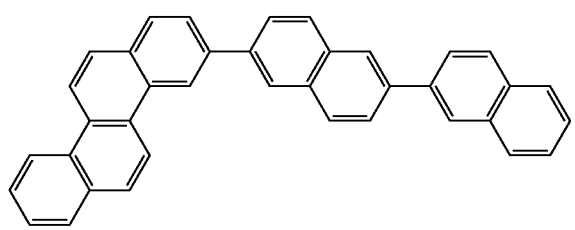
EM10
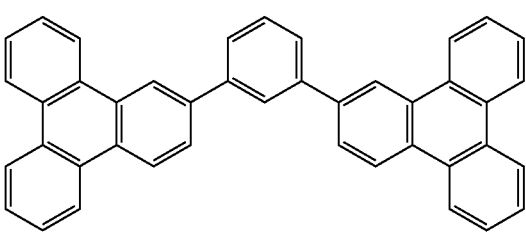
EM11
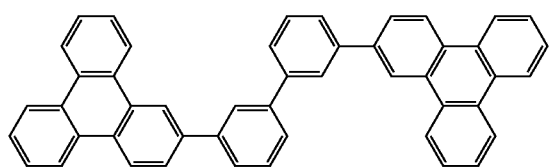
EM12
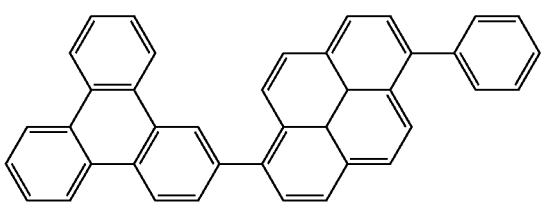

-continued
EM13
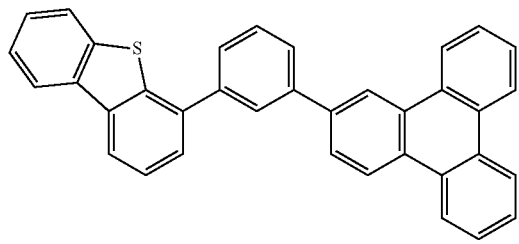
EM14
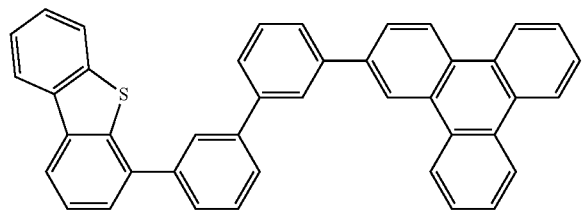
EM15
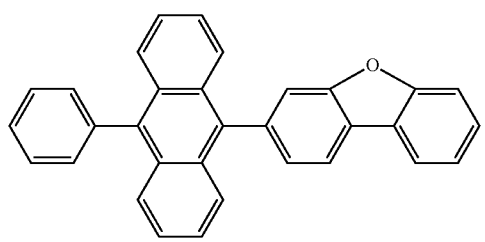
EM16
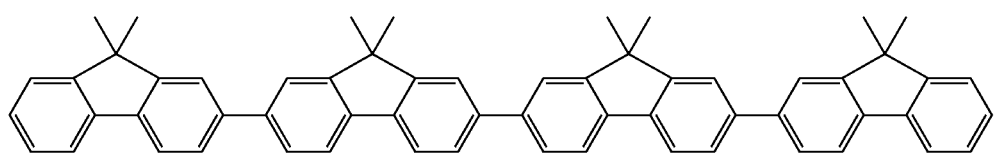
EM17
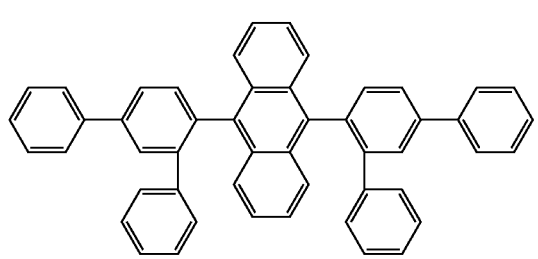
EM18
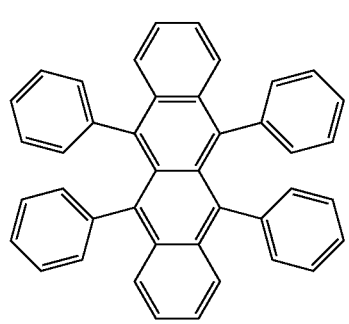
EM19
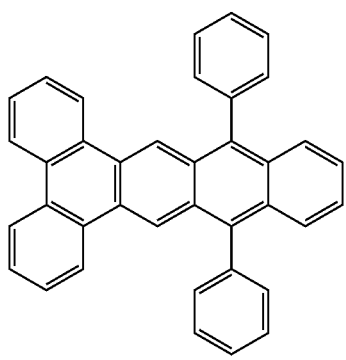
EM20
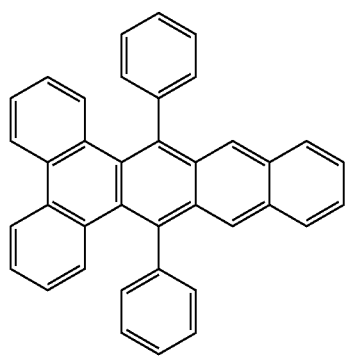

-continued
EM21
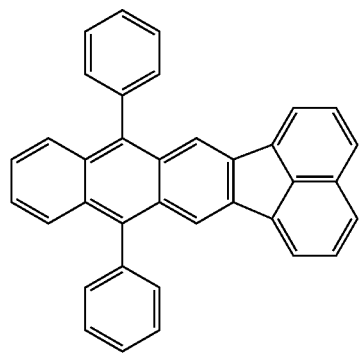
EM22
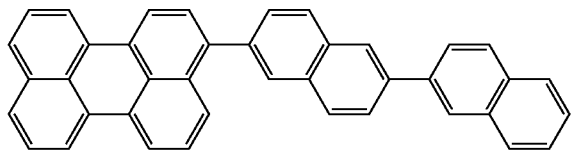
EM23
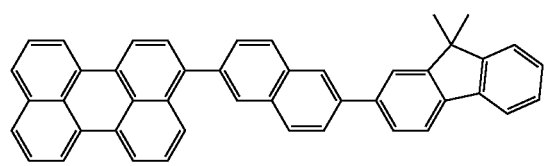
EM24
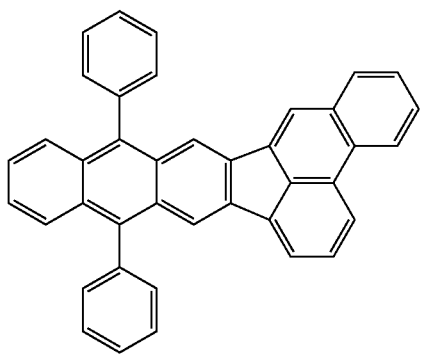
EM25
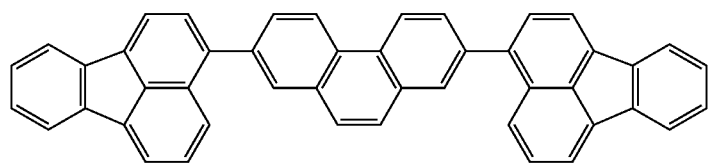
EM26
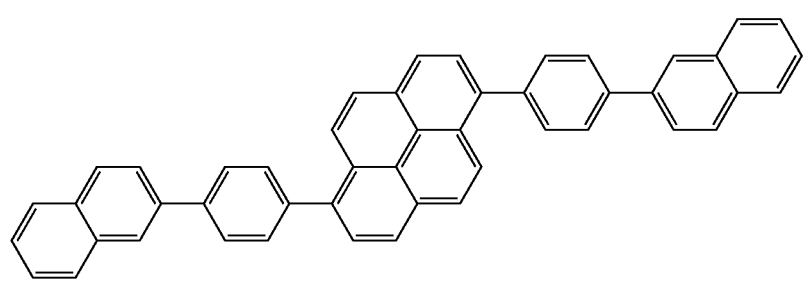
EM27
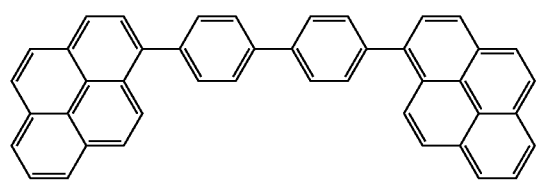
EM28
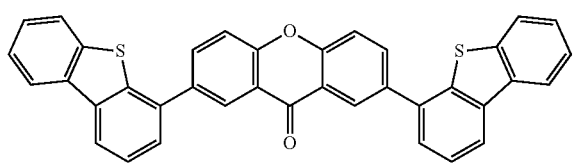

-continued
EM29
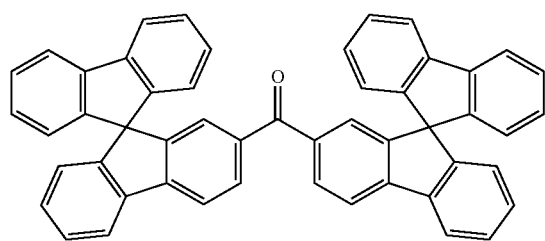
EM30
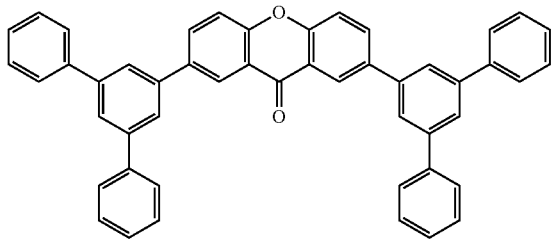
EM31
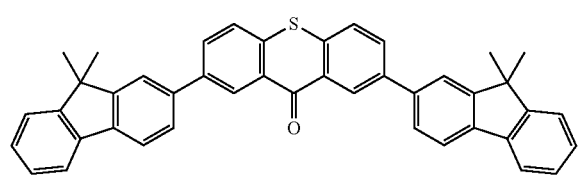
EM32
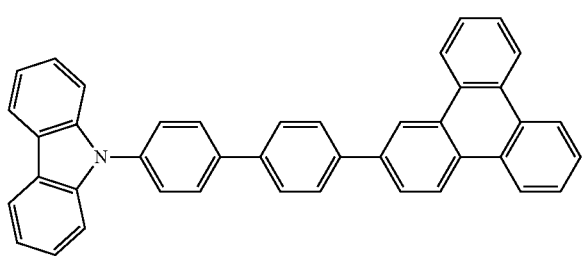
EM33
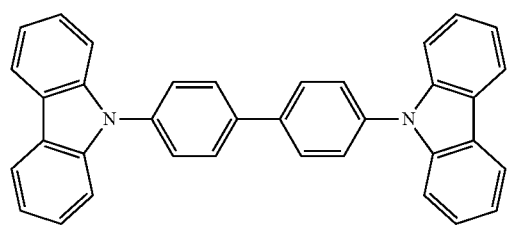
EM34
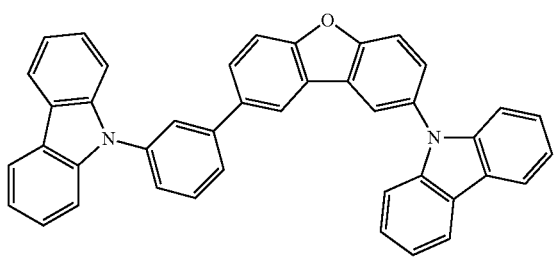
EM35
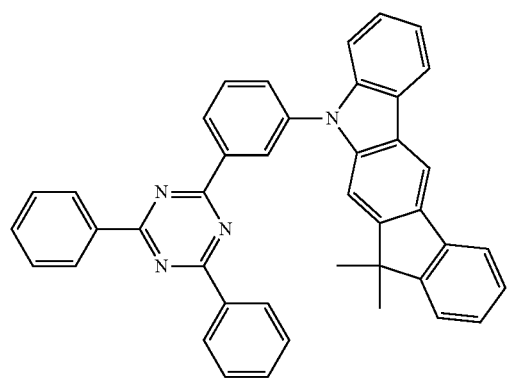
EM36
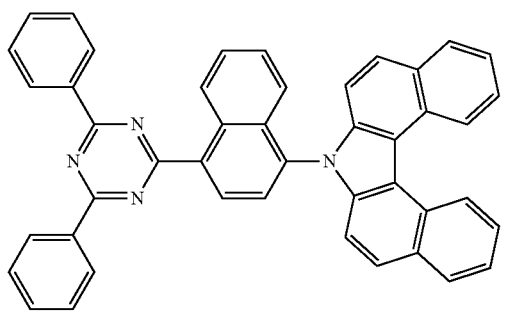
EM37
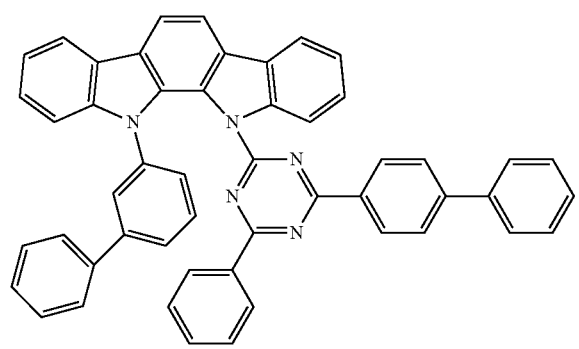
EM38
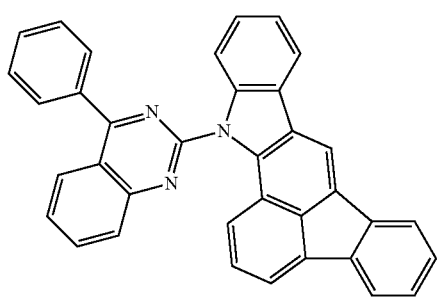

-continued

EM39
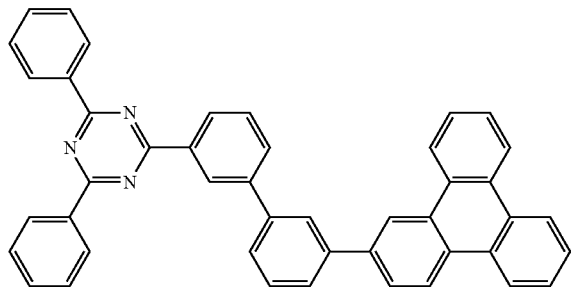

EM40
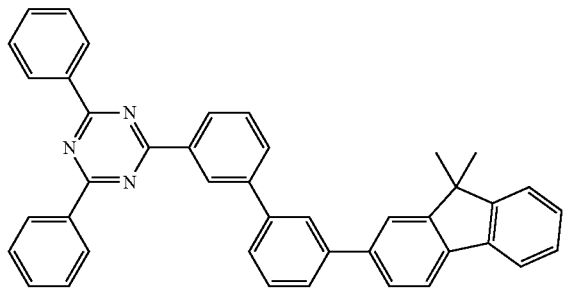

When the host material is a hydrocarbon compound, the compound according to the embodiment can easily trap electrons and holes to contribute to higher efficiency. The term "hydrocarbon compound" refers to a compound consisting of only carbon and hydrogen, and EM1 to EM12 and EM16 to EM27 are hydrocarbon compounds.

The electron transport material can be freely-selected from materials capable of transporting electrons injected from the cathode to the light-emitting layer and is selected in consideration of, for example, the balance with the hole mobility of the hole transport material. Examples of a material having the ability to transport electrons include oxadiazole derivatives, oxazole derivatives, pyrazine derivatives, triazole derivatives, triazine derivatives, quinoline derivatives, quinoxaline derivatives, phenanthroline derivatives, organoaluminum complexes, and condensed-ring compounds, such as fluorene derivatives, naphthalene derivatives, chrysene derivatives, and anthracene derivatives. The electron transport materials can be used for the hole-blocking layer. Non-limiting specific examples of a compound used as the electron transport material will be illustrated below.

ET1

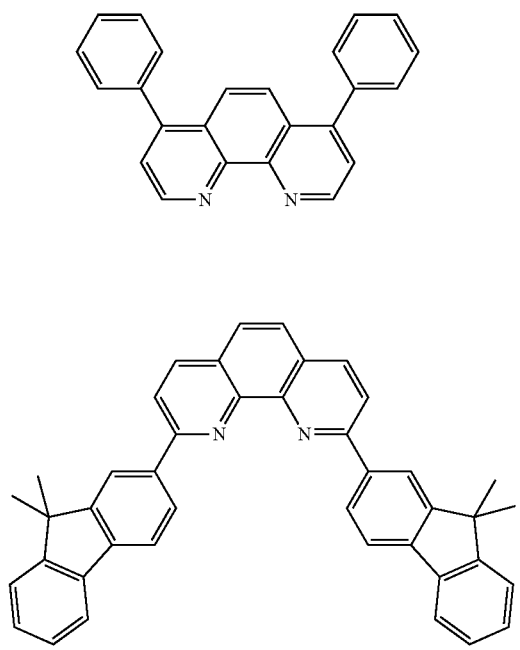

ET2

-continued

ET3
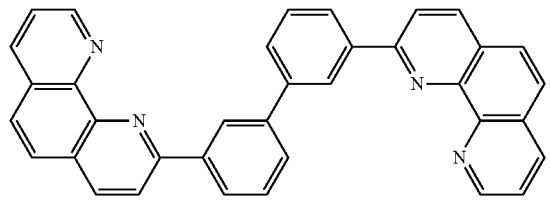

ET4
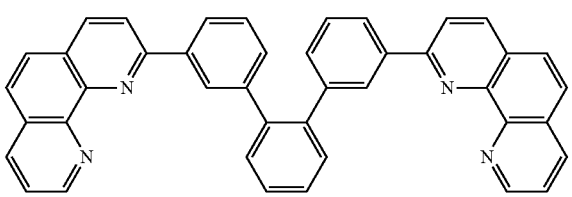

ET5
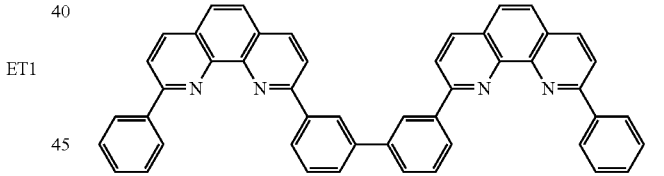

ET6
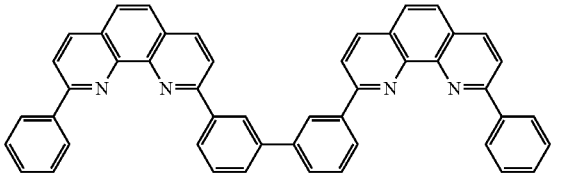

ET7
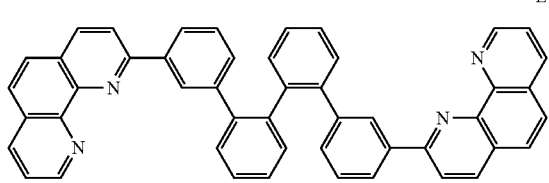

-continued

ET8
ET9
ET10
ET11
ET12
ET13
ET14
ET15
ET16
ET17

-continued
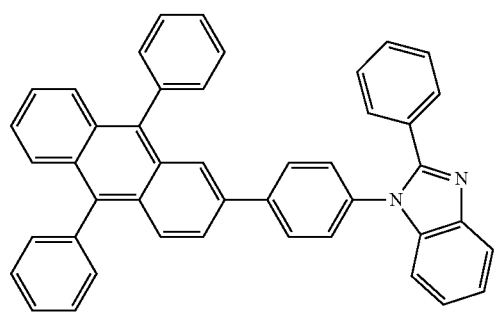
ET18
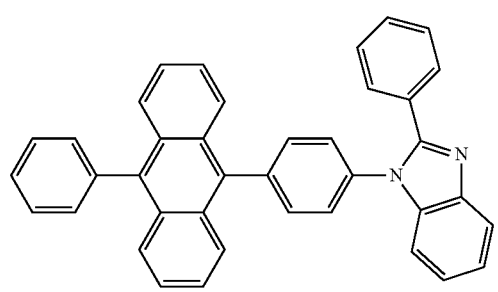
ET19
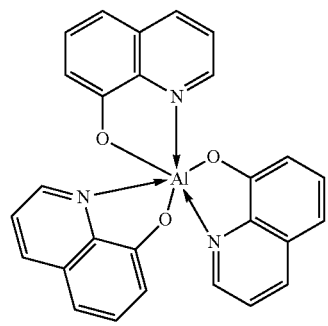
ET20
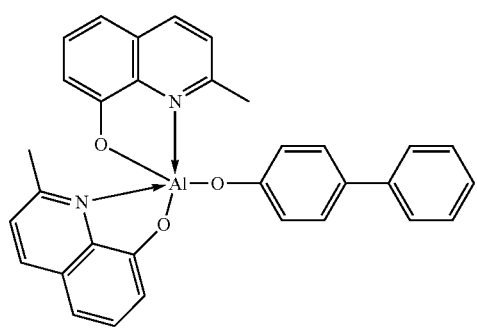
ET21
-continued
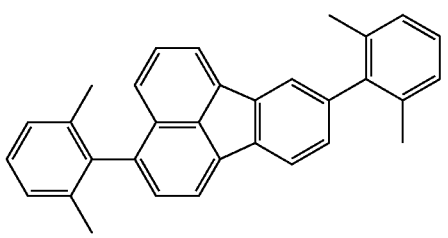
ET22
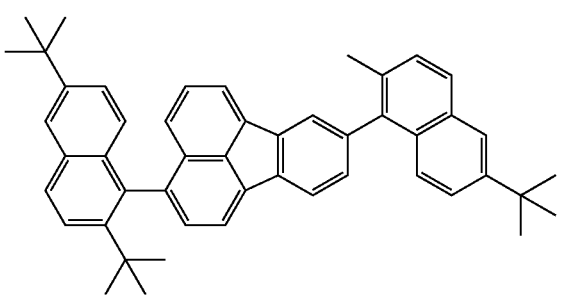
ET23
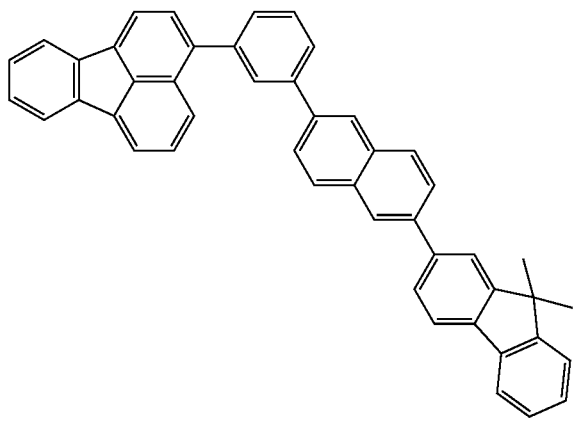
ET24
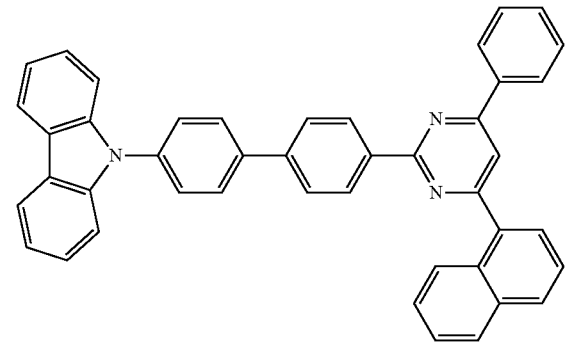
ET25

ET26

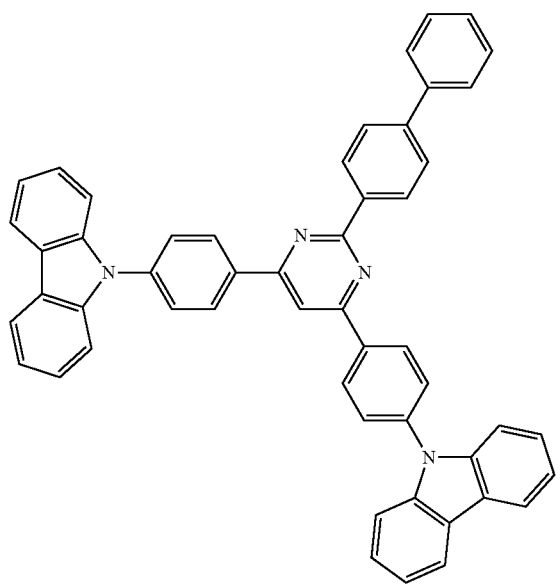

ET27

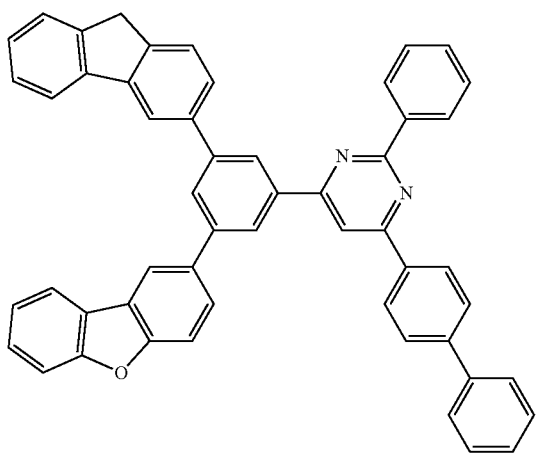

An electron injection material can be freely-selected from materials capable of easily injecting electrons from the cathode and is selected in consideration of, for example, the balance with the hole-injecting properties. As the organic compound, n-type dopants and reducing dopants are also included. Examples thereof include alkali metal-containing compounds, such as lithium fluoride, lithium complexes, such as lithium quinolinolate, benzimidazolidene derivatives, imidazolidene derivatives, fulvalene derivatives, and acridine derivatives.

Configuration of Organic Light-Emitting Device

The organic light-emitting device is provided by disposing an anode, the organic compound layer, and a cathode on a substrate. A protective layer, a color filter, and so forth may be disposed on the cathode. In the case of disposing the color filter, a planarization layer may be disposed between the protective layer and the color filter. The planarization layer can be composed of, for example, an acrylic resin.

Substrate

Examples of the substrate include silicon wafers, quartz substrates, glass substrates, resin substrates, and metal substrates. The substrate may include switching devices such as a transistor, a line, and an insulating layer thereon. As the insulating layer, any material can be used as long as a contact hole can be formed to establish the electrical connection between the anode and the line and as long as insulation with a non-connected line can be ensured. For example, a resin such as polyimide, silicon oxide, or silicon nitride can be used.

Electrode

A pair of electrodes can be used. The pair of electrodes may be an anode and a cathode. In the case where an electric field is applied in the direction in which the organic light-emitting device emits light, an electrode having a higher potential is the anode, and the other is the cathode. It can also be said that the electrode that supplies holes to the light-emitting layer is the anode and that the electrode that supplies electrons is the cathode.

As the constituent material of the anode, a material having a work function as high as possible can be used. Examples of the material that can be used include elemental metals, such as gold, platinum, silver, copper, nickel, palladium, cobalt, selenium, vanadium, and tungsten, mixtures thereof, alloys of combinations thereof, and metal oxides, such as tin oxide, zinc oxide, indium oxide, indium-tin oxide (ITO), and indium-zinc oxide. Additionally, conductive polymers, such as polyaniline, polypyrrole, and polythiophene, may be used.

These electrode materials may be used alone or in combination of two or more. The anode may be formed of a single layer or multiple layers.

In the case where the anode is used as a reflective electrode, for example, chromium, aluminum, silver, titanium, tungsten, molybdenum, an alloy thereof, or a stack thereof may be used. In the case where the anode is used as a transparent electrode, a transparent conductive oxide layer composed of, for example, indium-tin oxide (ITO) or indium-zinc oxide may be used; however, the anode is not limited thereto. The electrode may be formed by photolithography.

As the constituent material of the cathode, a material having a lower work function can be used. Examples thereof include elemental metals such as alkali metals. e.g., lithium, alkaline-earth metals. e.g., calcium, aluminum, titanium, manganese, silver, lead, and chromium, and mixtures thereof. Alloys of combinations of these elemental metals may also be used. For example, magnesium-silver, aluminum-lithium, aluminum-magnesium, silver-copper, and zinc-silver may be used. Metal oxides such as indium-tin oxide (ITO) may also be used. These electrode materials may be used alone or in combination of two or more. The cathode may have a single-layer structure or a multilayer structure. In particular, silver can be used. To reduce the aggregation of silver, a silver alloy can be used. Any alloy ratio may be used as long as the aggregation of silver can be reduced. For example, 1:1 may be used.

Atop emission device may be provided using the cathode formed of a conductive oxide layer composed of, for example, ITO. A bottom emission device may be provided using the cathode formed of a reflective electrode composed of, for example, aluminum (Al). The cathode is not particularly limited. Any method for forming the cathode may be used. For example, a direct-current or alternating-current sputtering technique can be employed because good film coverage is obtained and thus the resistance is easily reduced.

Protective Layer

A protective layer may be disposed on the cathode. For example, a glass member provided with a moisture absorbent can be bonded to the cathode to reduce the entry of, for example, water into the organic compound layer, thereby suppressing the occurrence of display defects. In another embodiment, a passivation film composed of, for example, silicon nitride may be disposed on the cathode to reduce the entry of, for example, water into the organic compound layer. For example, after the formation of the cathode, the substrate may be transported to another chamber without breaking the vacuum, and a silicon nitride film having a thickness of 2 μm may be formed by a chemical vapor deposition (CVD) method to provide a protective layer. After the film deposition by the CVD method, a protective layer may be formed by an atomic layer deposition (ALD) method.

Color Filter

A color filter may be disposed on the protective layer. For example, a color filter may be disposed on another substrate in consideration of the size of the organic light-emitting device and bonded to the substrate provided with the organic light-emitting device. A color filter may be formed by patterning on the protective layer using photolithography. The color filter may be composed of a polymer.

Planarization Layer

A planarization layer may be disposed between the color filter and the protective layer. The planarization layer may be composed of an organic compound. A low- or high-molecular-weight organic compound may be used. A high-molecular-weight organic compound can be used.

The planarization layers may be disposed above and below (or on) the color filter and may be composed of the same or different materials. Specific examples thereof include poly(vinyl carbazole) resins, polycarbonate resins, polyester resins, acrylonitrile butadiene styrene (ABS) resins, acrylic resins, polyimide resins, phenolic resins, epoxy resins, silicone resins, and urea resins.

Opposite Substrate

An opposite substrate may be disposed on the planarization layer. The opposite substrate is disposed at a position corresponding to the substrate described above and thus is called an opposite substrate. The opposite substrate may be composed of the same material as the substrate described above.

Organic Layer

The organic compound layer, such as the hole injection layer, the hole transport layer, the electron-blocking layer, the light-emitting layer, the hole-blocking layer, the electron transport layer, or the electron injection layer, included in the organic light-emitting device according to an embodiment of the present disclosure is formed by a method described below.

For the organic compound layer included in the organic light-emitting device according to an embodiment of the present disclosure, a dry process, such as a vacuum evaporation method, an ionized evaporation method, sputtering, or plasma, may be employed. Alternatively, instead of the dry process, it is also possible to employ a wet process in which a material is dissolved in an appropriate solvent and then a film is formed by a known coating method, such as spin coating, dipping, a casting method, a Langmuir-Blodgett (LB) technique, or an ink jet method.

In the case where the layer is formed by, for example, the vacuum evaporation method or the solution coating method, crystallization and so forth are less likely to occur, and good stability with time is obtained. In the case of forming a film by the coating method, the film may be formed in combination with an appropriate binder resin.

Non-limiting examples of the binder resin include poly (vinyl carbazole) resins, polycarbonate resins, polyester resins, acrylonitrile butadiene styrene (ABS) resins, acrylic resins, polyimide resins, phenolic resins, epoxy resins, silicone resins, and urea resins.

These binder resins may be used alone as a homopolymer or copolymer or in combination as a mixture of two or more. Furthermore, additives, such as a known plasticizer, antioxidant, and ultraviolet absorber, may be used, as needed.

Application of Organic Light-Emitting Device According to Embodiment of the Present Disclosure The organic light-emitting device according to an embodiment of the present disclosure can be used as component member of a display apparatus or a lighting device. Other applications include exposure light sources for electrophotographic image-forming apparatuses, backlights for liquid crystal displays, and light-emitting devices including white light sources and color filters.

The display apparatus may be an image information-processing unit having an image input unit that receives image information from an area or linear CCD sensor, a memory card, or any other source, an information-processing unit that processes the input information, and a display unit that displays the input image. The display apparatus includes multiple pixels, and at least one of the multiple pixels may include the organic light-emitting device according to the embodiment and a transistor coupled to the organic light-emitting device.

The display unit of an image pickup apparatus or an inkjet printer may have a touch panel function. The driving mode of the touch panel function may be, but is not limited to, an infrared mode, an electrostatic capacitance mode, a resistive film mode, or an electromagnetic inductive mode. The display apparatus may also be used for a display unit of a multifunction printer.

The following describes a display apparatus according to the embodiment with reference to the attached drawings. FIG. 4 is a schematic cross-sectional view of an example of a display apparatus including organic light-emitting devices and thin-film transistor (TFT) devices coupled to the respective organic light-emitting devices. Each of the TFT devices is an example of active devices.

A display apparatus 10 illustrated in FIG. 4 includes a substrate II composed of, for example, glass and a moisture-proof film 12 disposed thereon, the moisture-proof film 12 being configured to protect the TFT devices or the organic compound layers. Reference numeral 13 denotes a gate electrode composed of a metal. Reference numeral 14 denotes a gate insulating film. Reference numeral 15 denotes a semiconductor layer.

TFT devices 18 each include the semiconductor layer 15, a drain electrode 16, and a source electrode 17. An insulating film 19 is disposed on the TFT devices 18. An anode 21 included in an organic light-emitting device 26 is coupled to the source electrode 17 through a contact hole 20.

The way of electric coupling between the electrodes (the anode 21 and a cathode 23) included in each of the organic light-emitting devices 26 and the electrodes (the source electrode 17 and the drain electrode 16) included in a corresponding one of the TFT devices 18 is not limited to the configuration illustrated in FIG. 4. It is sufficient that one of the anode 21 and the cathode 23 is electrically coupled to one of the source electrode 17 and the drain electrode 16 of the TFT device 18.

In the display apparatus 10 illustrated in FIG. 4, each organic compound layer 22 is illustrated as a single layer; however, the organic compound layer 22 may be formed of multiple layers. A first protective layer 24 and a second protective layer 25 are disposed on the cathodes 23 in order to reduce the deterioration of the organic light-emitting devices 26.

In the display apparatus 10 illustrated in FIG. 4, the transistors are used as switching devices; however, metal-insulator-metal (MIM) devices may be used as switching devices.

The transistors used in the display apparatus 10 illustrated in FIG. 4 are not limited to transistors formed using a single-crystal silicon wafer and may be thin-film transistors each having an active layer on the insulating surface of a substrate. Examples of the material of the active layer include single-crystal silicon, non-single-crystal silicon materials, such as amorphous silicon and microcrystalline silicon, and non-single-crystal oxide semiconductors, such as indium-zinc oxide and indium-gallium-zinc oxide. Thin-film transistors are also referred to as TFT devices.

The transistors in the display apparatus 10 illustrated in FIG. 4 may be formed in the substrate such as a Si substrate. The expression "formed in the substrate" indicates that the transistors are produced by processing the substrate such as a Si substrate. In the case where the transistors are formed in the substrate, the substrate and the transistors can be deemed to be integrally formed.

In the organic light-emitting device according to the embodiment, the luminance is controlled by the TFT devices, which are an example of switching devices; thus, an image can be displayed at respective luminance levels by arranging multiple organic light-emitting devices in the plane. The switching devices according to the embodiment are not limited to the TFT devices and may be low-temperature polysilicon transistors or active-matrix drivers formed on a substrate such as a Si substrate. The expression "on a substrate" can also be said to be "in the substrate". Whether transistors are formed in the substrate or TFT devices are used is selected in accordance with the size of a display unit. For example, in the case where the display unit has a size of about 0.5 inches, organic light-emitting devices can be disposed on a Si substrate.

Figure 5:
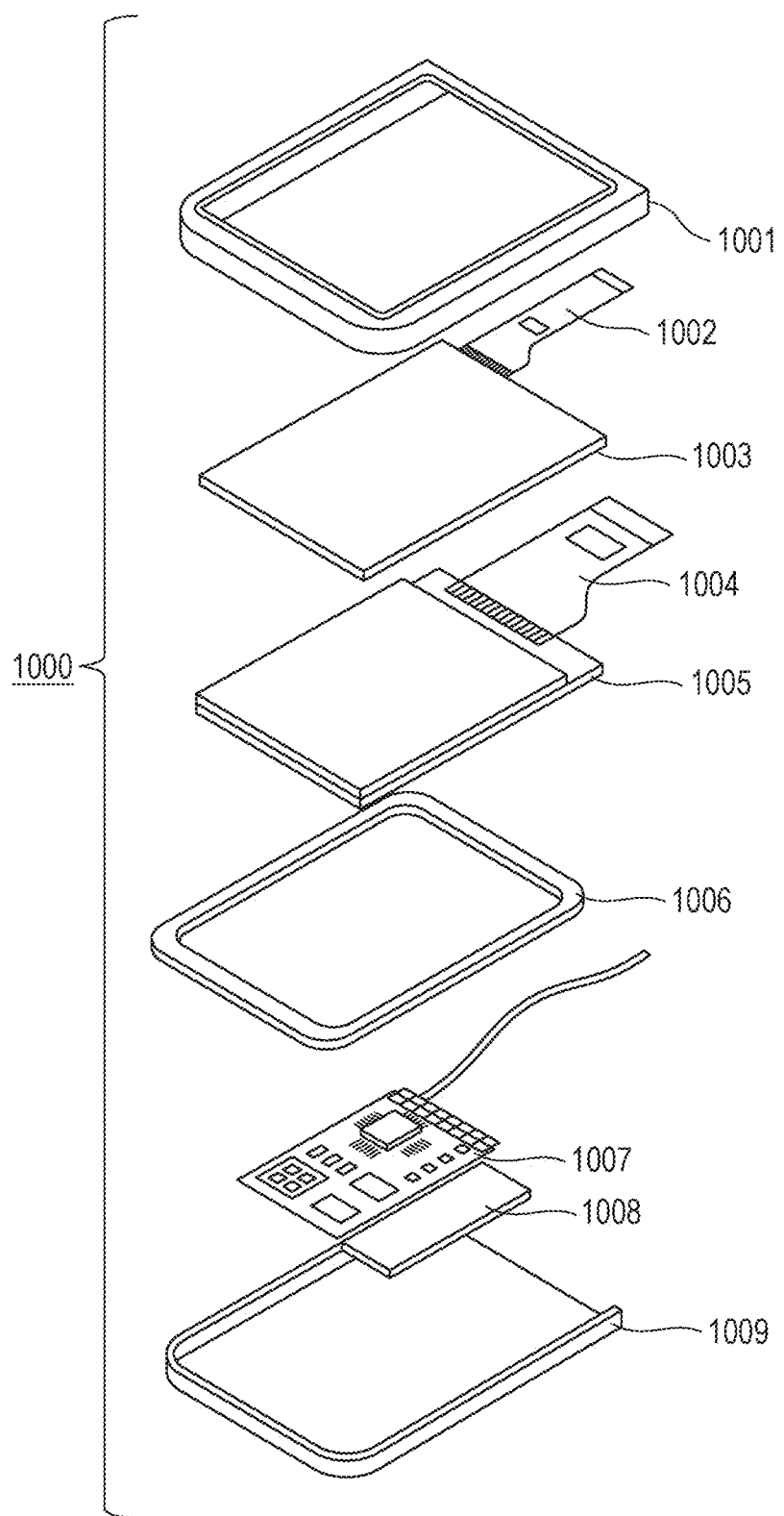
FIG. 5 is a schematic view of an example of a display apparatus according to an embodiment of the present disclosure.

FIG. 5 is a schematic view illustrating an example of a display apparatus according to the embodiment. A display apparatus 1000 may include a touch panel 1003, a display panel 1005, a frame 1006, a circuit substrate 1007, and a battery 1008 disposed between an upper cover 1001 and a lower cover 1009. The touch panel 1003 and the display panel 1005 are coupled to flexible printed circuits FPCs 1002 and 1004, respectively. The circuit substrate 1007 includes printed transistors. The battery 1008 need not be provided unless the display apparatus is a portable apparatus. The battery 1008 may be disposed at a different position even if the display apparatus is a portable apparatus.

The display apparatus according to the embodiment may be used for a display unit of a photoelectric conversion apparatus, such as an image pickup apparatus including an optical unit including multiple lenses and an image pickup device that receives light passing through the optical unit. The image pickup apparatus may include a display unit that displays information acquired by the image pickup device. The display unit may be a display unit exposed to the outside of the image pickup apparatus or a display unit disposed in a finder. The image pickup apparatus may be a digital camera or a digital camcorder.

Figure 6A:
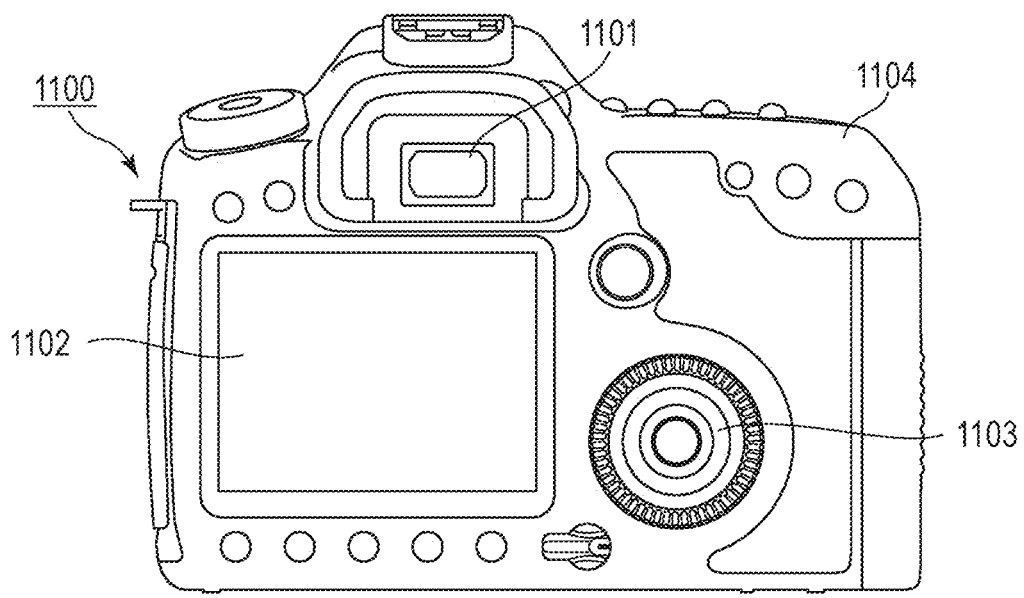
FIG. 6A is a schematic view of an example of an image pickup apparatus according to an embodiment of the present disclosure.

FIG. 6A is a schematic view illustrating an example of an image pickup apparatus according to the embodiment. An image pickup apparatus 1100 may include a viewfinder 1101, a rear display 1102, an operation unit 1103, and a housing 1104. The viewfinder 1101 may include the display apparatus according to the embodiment. In this case, the display apparatus may display environmental information, imaging instructions, and so forth in addition to an image to be captured. The environmental information may include, for example, the intensity of external light, the direction of the external light, the moving speed of a subject, and the possibility that a subject is shielded by a shielding material.

The timing suitable for imaging is only for a short time; thus, the information may be displayed as soon as possible. Accordingly, the display apparatus including the organic light-emitting device according to the embodiment can be used because of its short response time. The display apparatus including the organic light-emitting device can be used more suitably than liquid crystal displays for these units required to have a high display speed.

The image pickup apparatus 1100) includes an optical unit (not illustrated). The optical unit includes multiple lenses and is configured to form an image on an image pickup device in the housing 1104. The relative positions of the multiple lenses can be adjusted to adjust the focal point. This operation can also be performed automatically.

The display apparatus according to the embodiment may include a color filter having red, green, and blue portions. In the color filter, the red, green, and blue portions may be arranged in a delta arrangement.

A display apparatus according to the embodiment may be used for a display unit of an electronic apparatus, such as a portable terminal. In that case, the display apparatus may have both a display function and an operation function. Examples of the portable terminal include cellular phones, such as smartphones, tablets, and head-mounted displays.

Figure 6B:
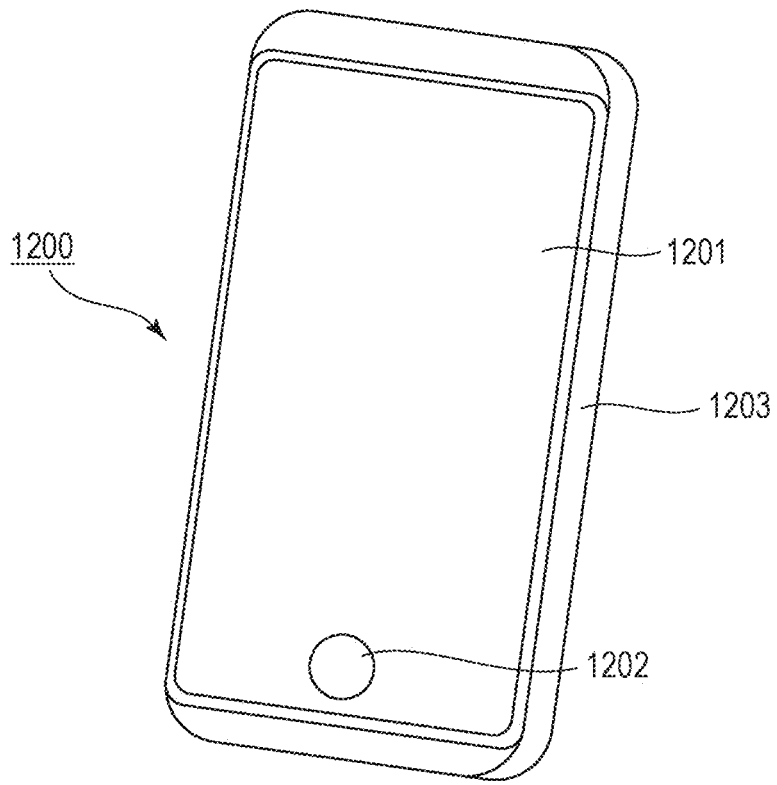
FIG. 6B is a schematic view of an example of an electronic apparatus according to an embodiment of the present disclosure.

FIG. 6B is a schematic view illustrating an example of an electronic apparatus according to the embodiment. An electronic apparatus 1200 includes a display unit 1201, an operation unit 1202, and a housing 1203. The housing 1203 may accommodate a circuit, a printed circuit board including the circuit, a battery, and a communication unit. The operation unit 1202 may be a button or a touch-panel-type reactive unit. The operation unit may be a biometric recognition unit that recognizes a fingerprint to release the lock or the like. An electronic apparatus having a communication unit can also be referred to as a communication apparatus.

Figure 7A:
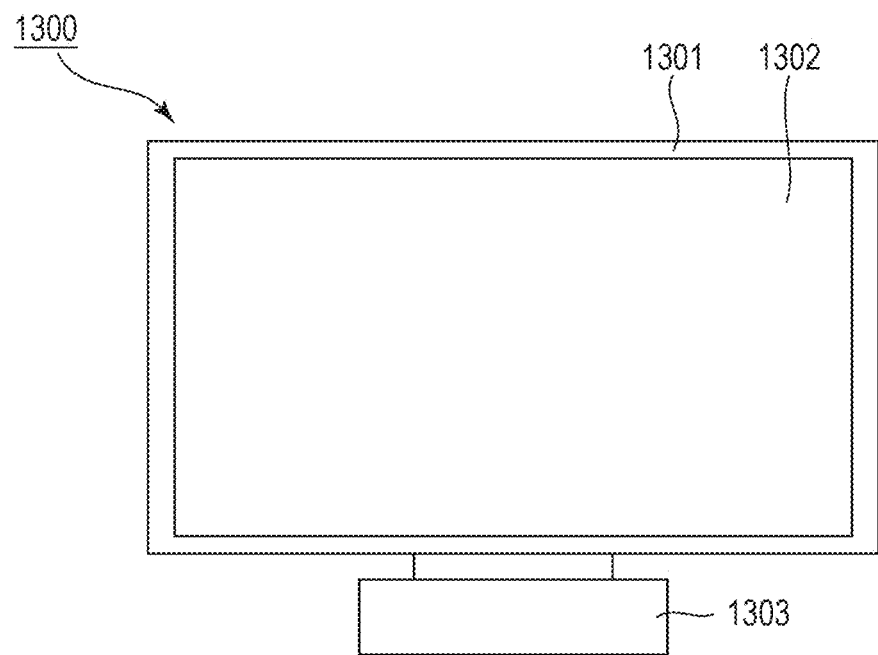
FIG. 7A is a schematic view of an example of a display apparatus according to an embodiment of the present disclosure.
Figure 7B:
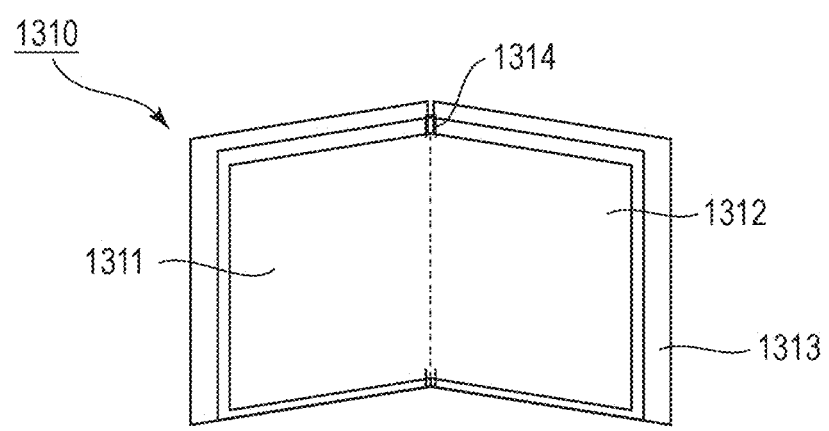
FIG. 7B is a schematic view of an example of a foldable display apparatus according to an embodiment of the present disclosure.

FIGS. 7A and 7B are schematic views illustrating examples of a display apparatus according to the embodiment. FIG. 7A illustrates a display apparatus, such as a television monitor or a personal computer monitor. A display apparatus 1300 includes a frame 1301 and a display unit 1302. The display unit 1302 may include an organic electroluminescent element according to the embodiment. The display device 1300 also includes a base 1303 that supports the frame 1301 and the display unit 1302. The base 1303 is not limited to a form illustrated in FIG. 7A. The lower side of the frame 1301 may also serve as a base. The frame 1301 and the display unit 1302 may be curved and may have a radius of curvature of 5,000 mm or more and 6,000 mm or less.

FIG. 7B is a schematic view illustrating another example of a display apparatus according to the embodiment. A display apparatus 1310 illustrated in FIG. 7B can be folded and is what is called a foldable display apparatus. The display apparatus 1310 includes a first display portion 1311, a second display portion 1312, a housing 1313, and an inflection point 1314. The first display portion 1311 and the second display portion 1312 may include a light-emitting device according to the embodiment. The first display portion 1311 and the second display portion 1312 may be a single, seamless display apparatus. The first display portion 1311 and the second display portion 1312 can be divided from each other at the inflection point. The first display portion 1311 and the second display portion 1312 may display different images from each other. Alternatively, a single image may be displayed in the first and second display portions.

Figure 8A:
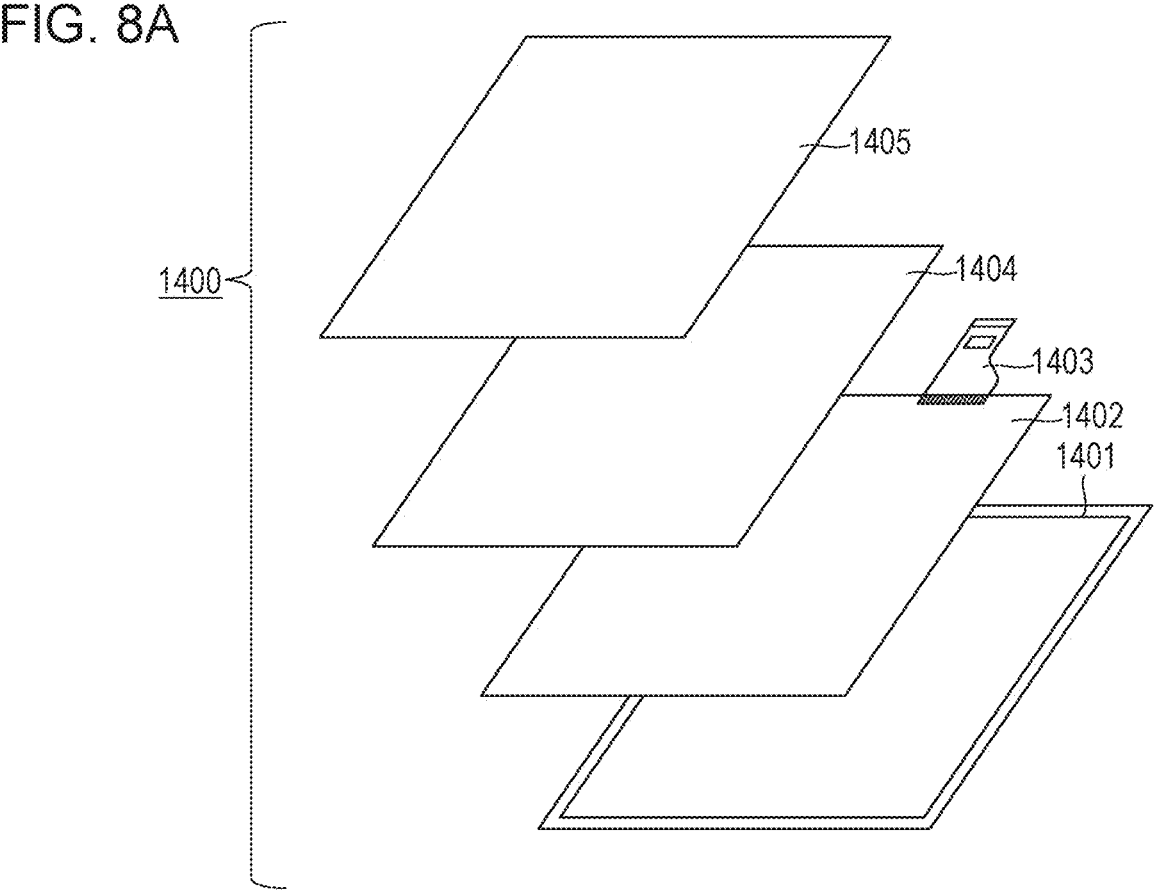
FIG. 8A is a schematic view of an example of a lighting device according to an embodiment of the present disclosure.

FIG. 8A is a schematic view illustrating an example of a lighting device according to the embodiment. A lighting device 1400 may include a housing 1401, a light source 1402, a circuit board 1403, an optical filter 1404 that transmits light emitted from the light source 1402, and a light diffusion unit 1405. The light source 1402 may include an organic light-emitting device according to the embodiment. The optical filter 1404 may be a filter that improves the color rendering properties of the light source. The light diffusion unit 1405 can effectively diffuse light from the light source to deliver the light to a wide range when used for illumination and so forth. The optical filter 1404 and the light diffusion unit 1405 may be disposed at the light emission side of the lighting device. A cover may be disposed at the outermost portion, as needed.

The lighting device is, for example, a device that lights a room. The lighting device may emit light of white, neutral white, or any color from blue to red. A light control circuit that controls the light may be provided. The lighting device may include the organic light-emitting device according to the embodiment and a power supply circuit coupled thereto. The power supply circuit is a circuit that converts an AC voltage into a DC voltage. The color temperature of white is 4,200 K. and the color temperature of neutral white is 5,000 K. The lighting device may include a color filter.

The lighting device according to the embodiment may include a heat dissipation unit. The heat dissipation unit is configured to release heat in the device to the outside of the device and is composed of, for example, a metal having a high specific heat and liquid silicone.

Figure 8B:
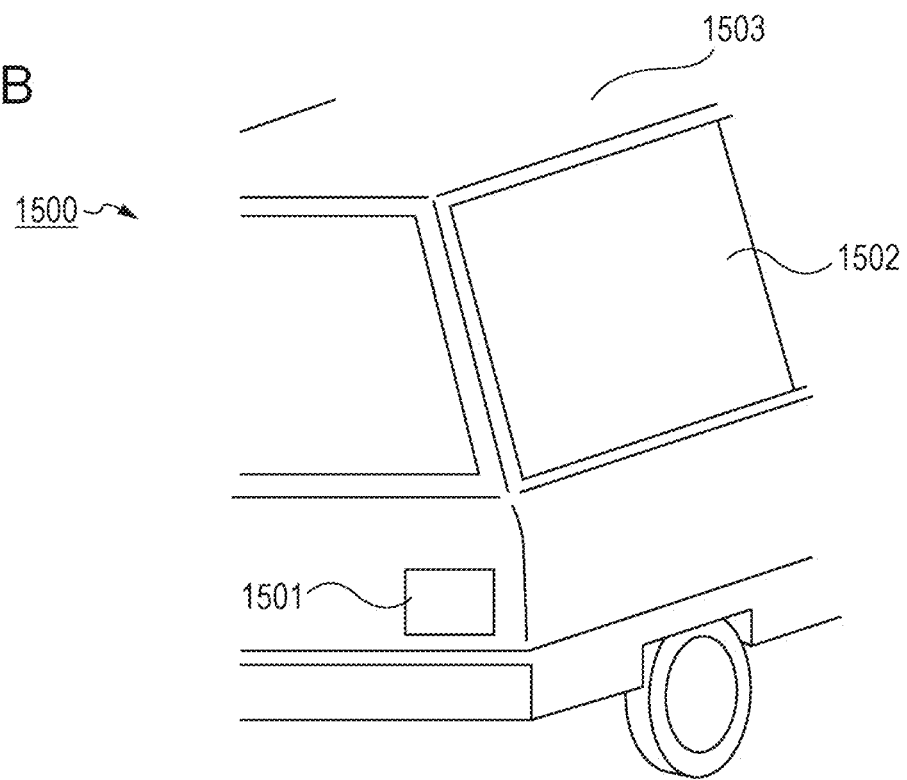
FIG. 8B is a schematic view of an example of an automobile including an automotive lighting unit according to an embodiment of the present disclosure.

FIG. 8B is a schematic view illustrating an automobile as an example of a moving object. The automobile includes a tail lamp, which is an example of lighting units. An automobile 1500 includes a tail lamp 1501 and may be configured to light the tail lamp when a brake operation or the like is performed.

The tail lamp 1501 may include an organic light-emitting device according to the embodiment. The tail lamp 1501 may include a protective member that protects the organic light-emitting device. The protective member may be composed of any transparent material having high strength to some extent and can be composed of, for example, polycarbonate. The polycarbonate may be mixed with, for example, a furandicarboxylic acid derivative or an acrylonitrile derivative.

The automobile 1500 may include an automobile body 1503 and windows 1502 attached thereto. The windows 1502 may be transparent displays if the windows are not used to check the front and back of the automobile. The transparent displays may include an organic light-emitting device according to the embodiment. In this case, the components, such as the electrodes, of the organic light-emitting device are formed of transparent members.

The moving object according to the embodiment may be, for example, a ship, an aircraft, or a drone. The moving object may include a body and a lighting unit attached to the body. The lighting unit may emit light to indicate the position of the body. The lighting unit includes the organic light-emitting device according to the embodiment.

Figure 9:
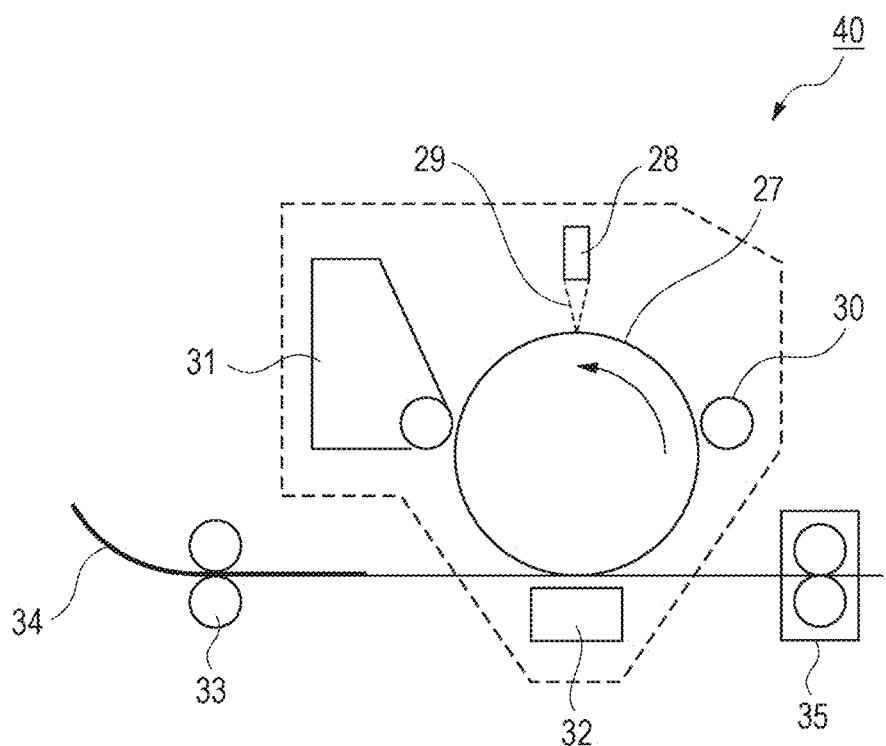
FIG. 9 is a schematic view of an example of an image-forming apparatus according to an embodiment of the present disclosure.

FIG. 9 is a schematic view of an example of an image-forming apparatus. An image-forming apparatus 40 is an electrophotographic image-forming apparatus and includes a photoconductor 27, an exposure light source 28, a charging unit 30, a developing unit 31, a transfer unit 32, a transport roller 33, and a fusing unit 35. Light 29 is emitted from the exposure light source 28 and forms an electrostatic latent image on the surface of the photoconductor 27. The exposure light source 28 includes the organic light-emitting device according to the embodiment. The developing unit 31 contains, for example, a toner. The charging unit 30 charges the photoconductor 27. The transfer unit 32 transfers the developed image to a recording medium 34. The transport roller 33 transports the recording medium 34. The recording medium 34 is paper, for example. The fusing unit 35 fixes the image formed on the recording medium 34.

Figure 10A:
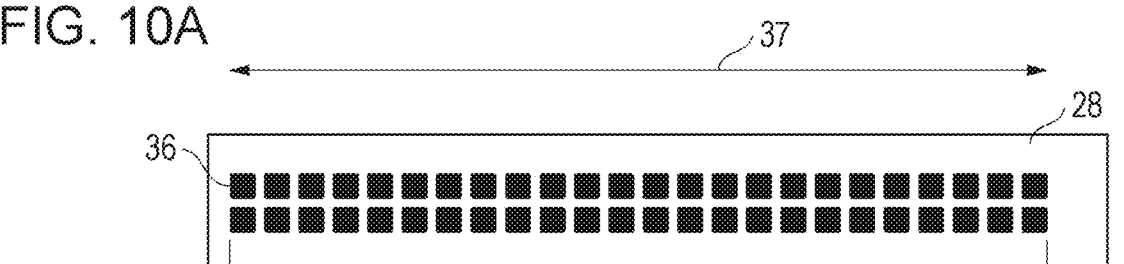
FIGS. 10A and 10B are schematic views of examples of an exposure light source for an image-forming apparatus according to an embodiment of the present disclosure.
Figure 10B:
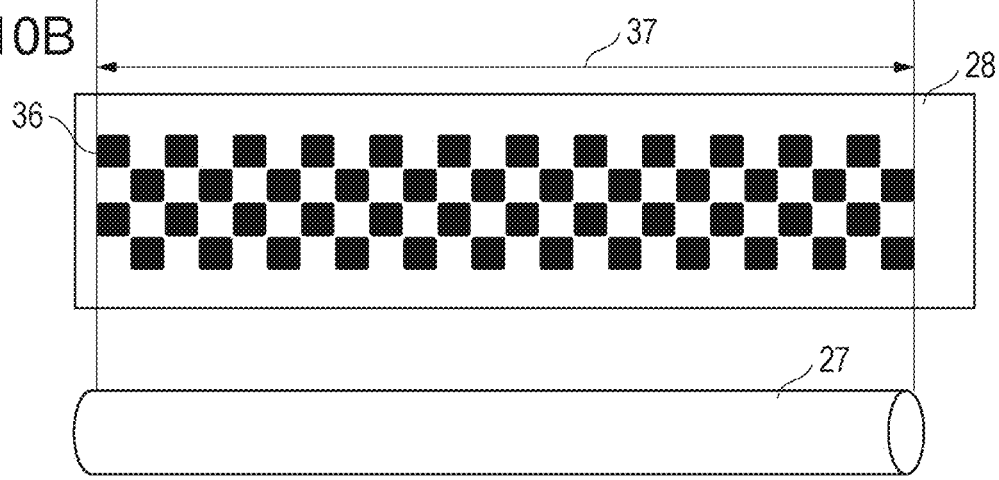

FIGS. 10A and 10B each illustrate the exposure light source 28 and are each a schematic view illustrating multiple light-emitting portions 36 arranged on a long substrate. Arrows 37 each represent the row direction in which the organic light-emitting devices are arranged. The row direction is the same as the direction of the axis on which the photoconductor 27 rotates. This direction can also be referred to as the long-axis direction of the photoconductor 27. FIG. 10A illustrates a configuration in which the light-emitting portions 36 are arranged in the long-axis direction of the photoconductor 27. FIG. 10B is different from FIG. 10A in that the light-emitting portions 36 are arranged alternately in the row direction in a first row and a second row. The first row and the second row are located at different positions in the column direction. In the first row, the multiple light-emitting portions 36 are spaced apart. The second row has the light-emitting portions 36 at positions corresponding to the positions between the light-emitting portions 36 in the first row. In other words, the multiple light-emitting portions 36 are also spaced apart in the column direction. The arrangement in FIG. 10B can be rephrased as, for example, a lattice arrangement, a staggered arrangement, or a checkered pattern.

As described above, the use of an apparatus including the organic light-emitting device according to the embodiment enables a stable display with good image quality even for a long time.

EXAMPLES

While the present disclosure will be described below by examples, the present disclosure is not limited these examples.

Example 1: Synthesis of Exemplified Compound B-1

Exemplified compound B-1 was synthesized according to the following scheme.

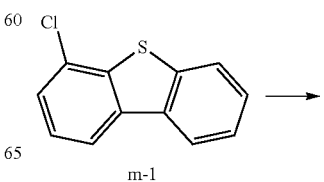

m-1

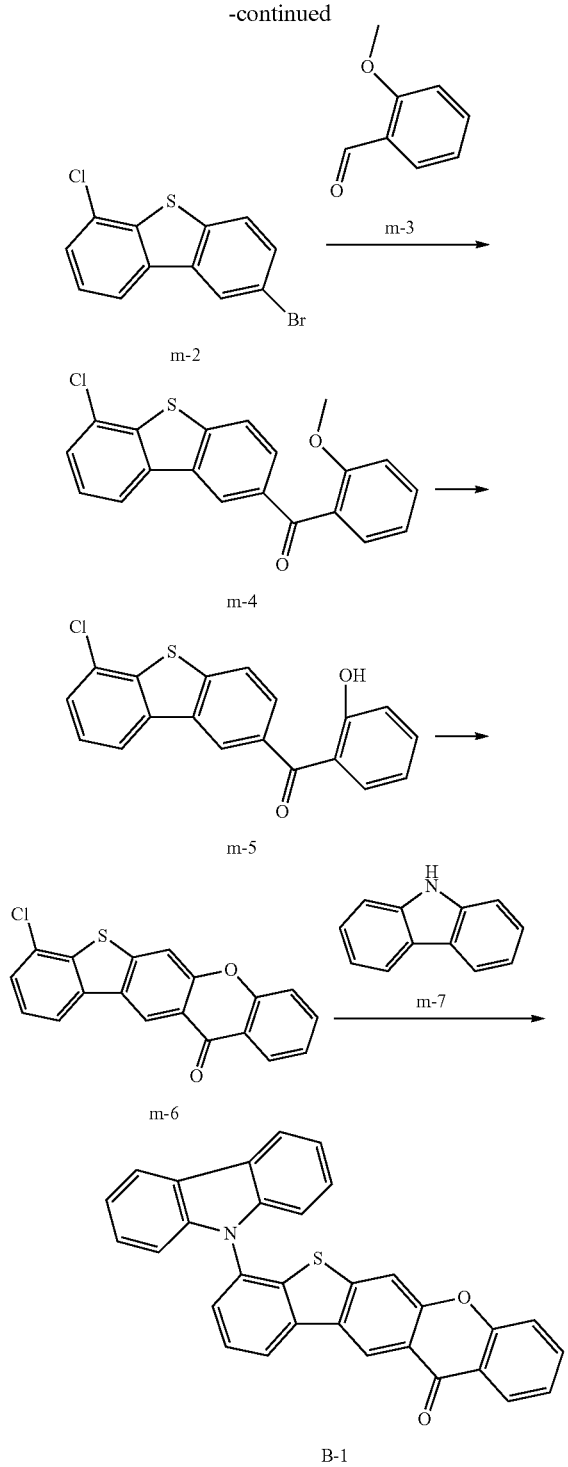

(1) Synthesis of Compound m-2

The following reagent and solvent were placed in a 500-mL recovery flask.

Compound m-1: 5.0 g (22.9 mmol)
Chloroform: 200 mL

The reaction solution was cooled to 0° C. under a stream of nitrogen, and then 11.0 g of bromine was added dropwise thereto. After the dropwise addition, the reaction solution was stirred at room temperature for 8 hours. The reaction solution was poured into ice water and extracted with toluene. The organic layer was concentrated to dryness to give a solid. The resulting solid was purified by silica gel column chromatography (toluene-heptane) to give 3.7 g (yield: 55%) of m-2.

(2) Synthesis of Compound m-4

The following reagent and solvent were placed in a 300-mL recovery flask.

Compound m-2: 3.5 g (11.8 mmol)
THF: 70 mL

The reaction solution was stirred at −78° C. for 1 hour under a stream of nitrogen, and then 5.2 mL of n-BuLi (2.5 M solution in hexane) was slowly added dropwise. After the dropwise addition, the reaction solution was stirred at −78° C. for 1 hour. A solution of 3.2 g (23.5 mmol) of compound m-3 in 35 mL of THF was slowly added dropwise to the reaction solution. After the dropwise addition, the reaction solution was stirred at room temperature for 2 hours. The reaction solution was quenched with a saturated aqueous ammonium chloride solution and subjected to extraction operation with ethyl acetate and a sodium chloride solution. The organic layer was concentrated to dryness to give a solid.

The resulting solid was dissolved in 35 mL of dichloromethane, and then 9.9 g of sodium bicarbonate and 5.5 g of Dess-Martin periodinane were added thereto. The mixture was stirred at room temperature for 7 hours under a stream of nitrogen. After the completion of the reaction, the reaction mixture was quenched with an aqueous sodium sulfite solution. A saturated aqueous sodium bicarbonate solution was added thereto. Extraction operation was performed with ethyl acetate. The organic layer was concentrated to dryness to give a solid. The resulting solid was purified by silica gel column chromatography (toluene) to give 2.7 g (yield: 65%) of m-4.

(3) Synthesis of Compound m-5

The following reagent and solvent were placed in a 500-mL recovery flask.

Compound m-4: 4.0 g (11.3 mmol)
Methylene chloride: 200 mL

Under a stream of nitrogen, 15 mL of boron tribromide (1 M, solution in dichloromethane) was added dropwise to the reaction solution at 0° C. After the dropwise addition, the reaction solution was stirred at room temperature for 8 hours. The reaction solution was poured into ice water and extracted with ethyl acetate. The organic layer was concentrated to dryness to give a solid. The resulting solid was purified by silica gel column chromatography (toluene-ethyl acetate mixture) to give 3.1 g (yield: 80%) of m-5.

(4) Synthesis of Compound m-6

The following reagents and solvents were placed in a 200-mL Schlenk flask.

Compound m-5: 2.5 g (7.4 mmol)
Pd(OAc)$_2$: 0.2 g (0.7 mmol)
3-Nitropyridine: 90 mg
Hexafluorobenzene: 7 mL
DMI: 7 mL
tert-Butyl perbenzoate: 2.9 g The reaction solution was heated to reflux at 90° C. for 7 hours with stirring under a stream of nitrogen. After the completion of the reaction, filtration was performed through Celite, and then the filtrate was concentrated to dryness. The resulting solid was purified by silica gel column chromatography (toluene) to give 1.6 g (yield: 65%) of m-6.

(6) Synthesis of Compound B-1

The following reagents and solvent were placed in a 500-mL recovery flask.

Compound m-6: 1.0 g (3.0 mmol)
Compound m-7: 0.6 g (3.6 mmol)
Sodium tert-butoxide: 0.9 g (4.90 mmol)
Pd(dba)$_2$: 170 mg
Xphos: 420 mg
o-Xylene: 50 mL The reaction solution was heated and stirred at 140° C. for 5 hours under a stream of nitrogen. After the completion of the reaction, filtration was performed through Celite, and then the filtrate was concentrated to dryness. The resulting solid was purified by silica gel column chromatography (toluene) to give 0.87 g (yield: 63%) of B-1 as a pale yellow solid.

Exemplified compound B-1 was subjected to mass spectrometry with MALDI-TOF-MS (Bruker Autoflex LRF).
MALDI-TOF-MS
Measured value: m/z=467
Calculated value: C$_{31}$H$_{17}$NO$_2$S=467

Examples 2 to 12: Syntheses of Exemplified Compounds

As presented in Table 1, exemplified compounds of Examples 2 to 12 were synthesized as in Example 1, except that raw material m-2 in Example 1 was changed to raw material 1, raw material m-3 was changed to raw material 2, and raw material m-7 was changed to raw material 3. The resulting exemplified compounds were subjected to mass spectrometry as in Example 1. Table 1 presents the measured values (m/z).

TABLE 1

| Example | Exemplified compound | Raw material 1 | Raw material 2 | Raw material 3 | m/z |
|---|---|---|---|---|---|
| 2 | B-2 | 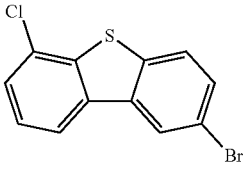 [SMILES: Clc1cccc2c1sc1ccc(Br)cc12] | 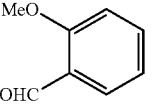 | 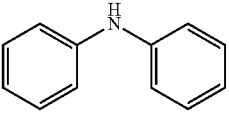 [SMILES: c1ccc(Nc2ccccc2)cc1] | 469 |
| 3 | B-3 | 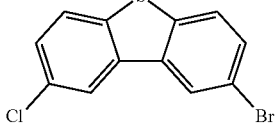 | 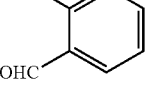 | 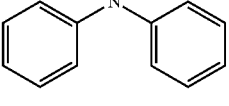 | 469 |
| 4 | B-14 | 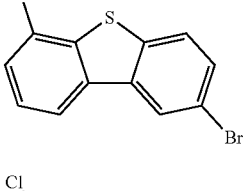 | 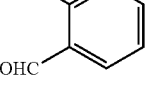 | 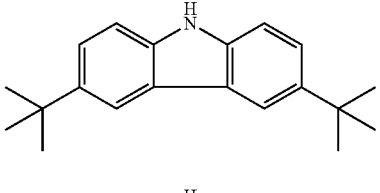 | 579 |
| 5 | B-18 | 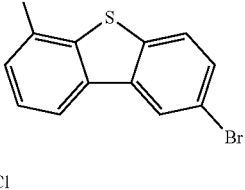 | 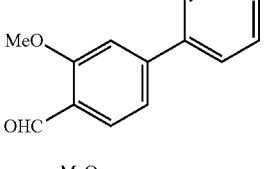 | 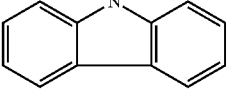 | 543 |
| 6 | C-1 | 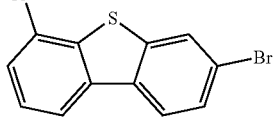 | 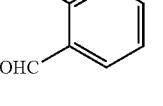 | 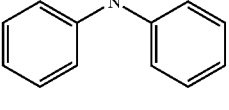 | 469 |
| 7 | C-9 | 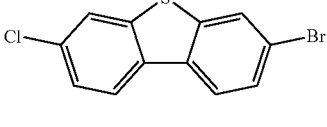 | 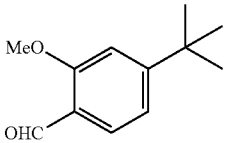 | 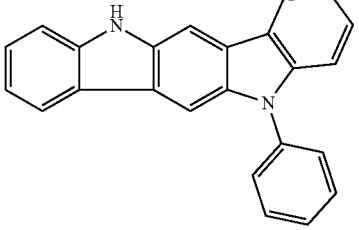 | 688 |

TABLE 1-continued

| Example | Exemplified compound | Raw material 1 | Raw material 2 | Raw material 3 | m/z |
|---|---|---|---|---|---|
| 8 | D-1 | 4-chloro-6-bromodibenzofuran | 2-methoxybenzaldehyde | diphenylamine | 453 |
| 9 | D-17 | chloro-bromodibenzofuran | 2-methoxy-4-fluorobenzaldehyde | diphenylamine | 471 |
| 10 | E-1 | 4-chloro-bromodibenzofuran | 2-methoxy-4-tert-butylbenzaldehyde | bis(2-methylphenyl)amine | 481 |
| 11 | E-21 | 3-bromodibenzofuran | 2-methoxy-5-chlorobenzaldehyde | carbazole | 451 |
| 12 | G-2 | 2-chloro-7-bromo-9,9-dimethylfluorene | 2-methoxybenzaldehyde | 3,6-di-tert-butylcarbazole | 589 |

Example 13: Synthesis of Exemplified Compound I-2

Exemplified compound I-2 was synthesized according to the following scheme.

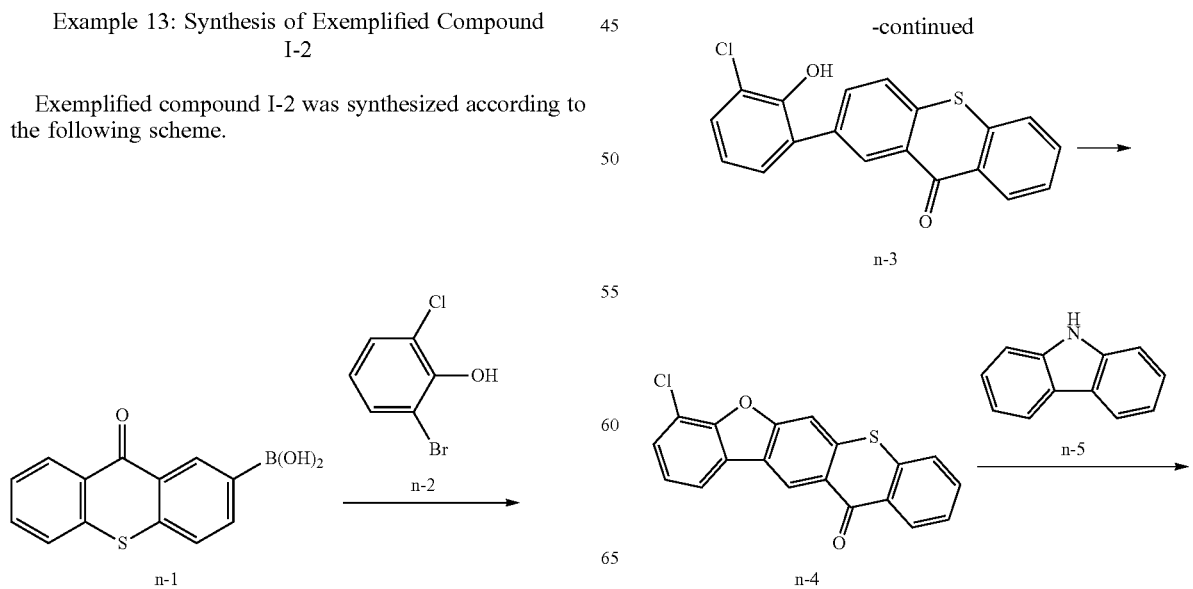

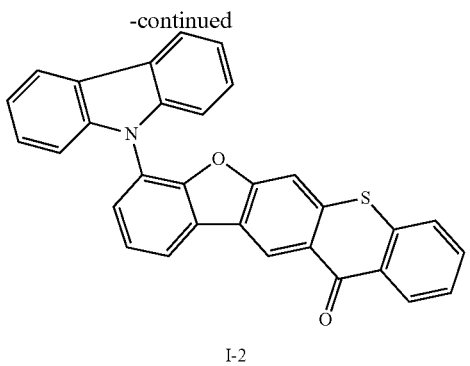

I-2

(1) Synthesis of Compound n-3

The following reagents and solvents were placed in a 200-mL recovery flask.
Compound n-1: 3.4 g (10.0 mmol)
Compound n-2: 2.2 g (11.0 mmol)
Sodium carbonate: 5.3 g (50.0 mmol)
Pd(PPh$_3$)$_2$Cl$_2$: 35 mg
Toluene: 35 mL
Water: 35 mL
Ethanol: 10 mL The reaction solution was heated and stirred at 60° C. for 5 hours under a stream of nitrogen. After the completion of the reaction, filtration was performed through Celite, and then the filtrate was concentrated to dryness. The resulting solid was purified by silica gel column chromatography (toluene-ethyl acetate mixture) to give 1.6 g (yield: 43%) of a yellow solid.

(2) Synthesis of Compound n-4

The following reagents and solvents were placed in a 200-mL Schlenk flask.
Compound n-3: 1.5 g (4.4 mmol)
Pd(OAc)$_2$: 0.1 g (0.4 mmol)
3-Nitropyridine: 50 mg
Hexafluorobenzene: 4 mL
DMI: 4 mL
tert-Butyl perbenzoate: 1.7 g The reaction solution was heated to reflux at 90° C. for 7 hours with stirring under a stream of nitrogen. After the completion of the reaction, filtration was performed through Celite, and then the filtrate was concentrated to dryness. The resulting solid was purified by silica gel column chromatography (toluene) to give 0.9 g (yield: 65%) of n-4.

(3) Synthesis of Compound I-2

The following reagents and solvent were placed in a 200-mL recovery flask.
Compound n-4: 0.9 g (2.7 mmol)
Compound n-5: 0.5 g (3.2 mmol)
Sodium tert-butoxide: 0.7 g (8.0 mmol)
Pd(dba)$_2$: 150 mg
Xphos: 380 mg
o-Xylene: 45 mL The reaction solution was heated and stirred at 140° C. for 5 hours under a stream of nitrogen. After the completion of the reaction, filtration was performed through Celite, and then the filtrate was concentrated to dryness. The resulting solid was purified by silica gel column chromatography (toluene-ethyl acetate mixture) to give 0.8 g (yield: 64%) of I-2 as a pale yellow solid.

Exemplified compound I-2 was subjected to mass spectrometry as in Example 1.
MALDI-TOF-MS
Measured value: m/z=467
Calculated value: C$_{44}$H$_{27}$NSO=467

Examples 14 and 15: Synthesis of Exemplified Compounds, and Comparative Example 1

As presented in Table 2, exemplified compounds of Examples 14 and 15 and comparative compound 1 were synthesized as in Example 13, except that raw material n-1 in Example 13 was changed to raw material 1, raw material n-2 was changed to raw material 2, and raw material n-5 was changed to raw material 3. For comparative compound 1, the same procedure was performed up to the second step of Example 13 to produce comparative compound 1. The exemplified compounds and the comparative compound were subjected to mass spectrometry as in Example 13. Table 2 presents the measured values (m/z).

TABLE 2

| Exemplified compound | | Raw material 1 | Raw material 2 | raw material 3 | m/z |
|---|---|---|---|---|---|
| Example 14 | I-4 | ![thioxanthone with phenyl and B(OH)₂] | ![chlorobromo phenol] | ![carbazole] | 545 |
| Example 15 | I-6 | ![thioxanthone with B(OH)₂] | ![chlorobromo phenol] | ![carbazole] | 467 |

TABLE 2-continued

| Exemplified compound | | Raw material 1 | Raw material 2 | raw material 3 | m/z |
|---|---|---|---|---|---|
| Comparative example 1 | Comparative compound 1 | 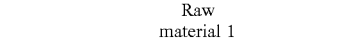 | 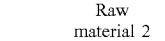 | not used | 300 |

Example 16: Synthesis of Exemplified Compound H-1

Exemplified compound H-1 was synthesized according to the following scheme.

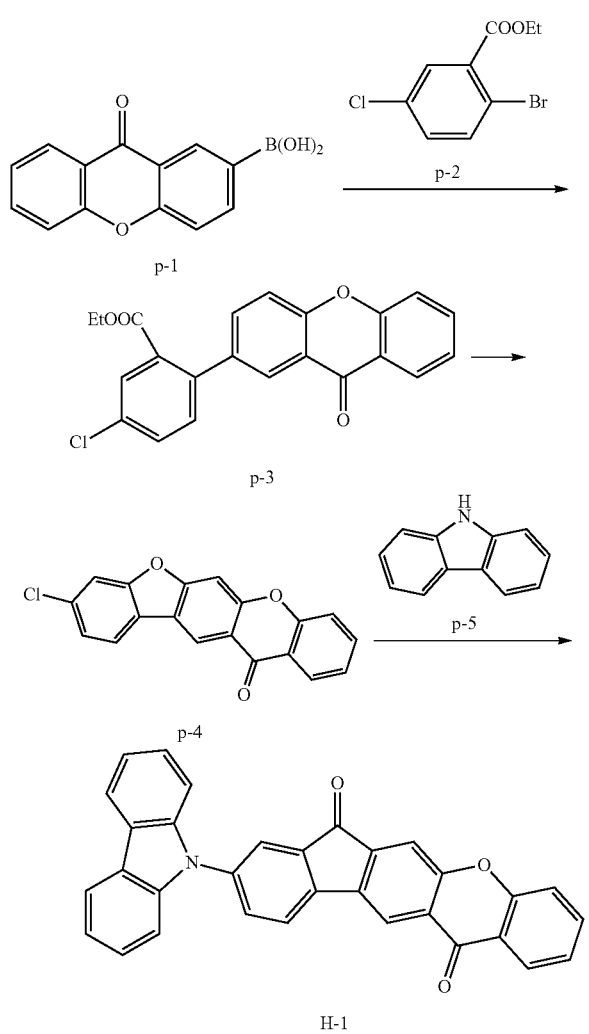

(1) Synthesis of Compound p-3
The following reagents and solvents were placed in a 200-mL recovery flask.
Compound p-1: 3.4 g (10.0 mmol)
Compound p-2: 2.2 g (11.0 mmol)
Sodium carbonate: 5.3 g (50.0 mmol)
Pd(PPh$_3$)$_2$Cl$_2$: 35 mg
Toluene: 35 mL
Water: 35 mL
Ethanol: 10 mL The reaction solution was heated and stirred at 60° C. for 5 hours under a stream of nitrogen. After the completion of the reaction, filtration was performed through Celite, and then the filtrate was concentrated to dryness. The resulting solid was purified by silica gel column chromatography (toluene-ethyl acetate mixture) to give 1.6 g (yield: 43%) of a yellow solid.

(2) Synthesis of Compound p-4
The following reagents and solvent were placed in a 200-mL recovery flask.
Compound p-3: 1.5 g (7.4 mmol)
Methanesulfonic acid: 1.1 g (11.1 mmol):
CH$_2$Cl$_2$: 50 mL The reaction solution was heated to reflux for 7 hours with stirring under a stream of nitrogen. After the completion of the reaction, 100 mL of water was added thereto, and then the mixture was extracted with ethyl acetate. The organic layer was concentrated to dryness. The resulting solid was dispersed and washed with toluene to give 1.2 g (yield: 65%) of p-4.

(3) Synthesis of Compound H-1
The following reagents and solvent were placed in a 200-mL recovery flask.
Compound p-4: 1.3 g (2.69 mmol)
Compound p-5: 0.499 g (2.95 mmol)
Sodium tert-butoxide: 0.47 g (4.90 mmol)
Pd(dba)$_2$: 75 mg
Xphos: 420 mg
o-Xylene: 30 mL The reaction solution was heated and stirred at 140° C. for 5 hours under a stream of nitrogen. After the completion of the reaction, filtration was performed through Celite, and then the filtrate was concentrated to dryness. The resulting solid was purified by silica gel column chromatography (toluene-ethyl acetate mixture) to give 1.1 g (yield: 68%) of H-1 as a yellow solid.

Exemplified compound H-1 was subjected to mass spectrometry as in Example 1.
MALDI-TOF-MS
Measured value: m/z=463
Calculated value: C$_{44}$H$_{27}$NSO=463

Example 17

In this Example, an organic light-emitting device having a bottom-emission structure was produced in which an anode, a hole injection layer, a hole transport layer, an electron-blocking layer, a light-emitting layer, a hole-blocking layer, an electron transport layer, an electron injection layer, and a cathode were sequentially formed on a substrate.

An ITO film was formed on a glass substrate and subjected to desired patterning to form an ITO electrode (anode). The ITO electrode had a thickness of 100 nm. The substrate on which the ITO electrode had been formed in this way was used as an ITO substrate in the following steps. Next, vacuum evaporation was performed by resistance heating in a vacuum chamber to continuously form organic compound layers and an electrode layer presented in Table 3 on the ITO substrate. Here, the opposite electrode (metal electrode layer, cathode) had an electrode area of 3 mm$^2$.

TABLE 3

|  | Material |  | Thickness (nm) |
|---|---|---|---|
| Cathode | Al |  | 100 |
| Electron injection layer (EIL) | LiF |  | 1 |
| Electron transport layer (ETL) | ET2 |  | 15 |
| Hole-blocking layer (HBL) | ET11 |  | 15 |
| Light-emitting layer (EML) | host | light-emitting material | 20 |
|  | EM11 | B-1 |  |
| Light-emitting layer % by mass [%] | 88 | 12 |  |
| Electron-blocking layer (EBL) | HT12 |  | 15 |
| Hole transport layer (HTL) | HT3 |  | 30 |
| Hole injection layer (HIL) | HT16 |  | 5 |

The characteristics of the resulting device were measured and evaluated. As the initial characteristics associated with the light emission, green light emission with a maximum external quantum efficiency (E.Q.E.) of 5.8% was obtained. With regard to measurement instruments, specifically, the current-voltage characteristics were measured with a Hewlett-Packard 4140B microammeter, and the luminance was measured with a Topcon BM7. The device was subjected to a continuous operation test at a current density of 50 mA/cm$^2$. The time when the percentage of luminance degradation reached 5% (LT95) was measured to be 108 hours.

Examples 18 to 22

Organic light-emitting devices were produced in the same way as in Example 17, except that the compounds listed in Table 4 were used as appropriate. The characteristics of the resulting devices were measured and evaluated in the same way as in Example 17. Table 4 presents the measurement results.

TABLE 4

|  |  |  | EML | | | | E.Q.E | LT95 | Emission |
|---|---|---|---|---|---|---|---|---|---|
|  | HTL | EBL | Host | Light-emitting material | HBL | ETL | [%] | [h] | color |
| Example 18 | HT3 | HT12 | EM10 | C-1 | ET12 | ET2 | 5.6 | 115 | green |
| Example 19 | HT3 | HT11 | EM11 | E-4 | ET12 | ET2 | 5.6 | 118 | green |
| Example 20 | HT3 | HT12 | EM4 | B-26 | ET12 | ET2 | 4.8 | 60 | green |
| Example 21 | HT2 | HT11 | EM9 | E-21 | ET12 | ET2 | 5.0 | 110 | green |
| Example 22 | HT2 | HT10 | EM32 | D-1 | ET12 | ET5 | 5.3 | 90 | green |

Example 23

An organic light-emitting device was produced in the same way as in Example 17, except that the organic compound layers and the electrode layer listed in Table 5 were continuously deposited.

TABLE 5

|  | Material |  |  | Thickness (nm) |
|---|---|---|---|---|
| Cathode | Al |  |  | 100 |
| Electron injection layer (EIL) | LiF |  |  | 1 |
| Electron transport layer (ETL) | ET2 |  |  | 15 |
| Hole-blocking layer (HBL) | ET11 |  |  | 15 |
| Light-emitting layer (EML) | host | assist material | light-emitting material | 20 |
|  | EM11 | B-3 | GD6 |  |
| Light-emitting layer % by mass [%] | 82 | 15 | 3 |  |
| Electron-blocking layer (EBL) | HT12 |  |  | 15 |
| Hole transport layer (HTL) | HT3 |  |  | 30 |
| Hole injection layer (HIL) | HT16 |  |  | 5 |

The characteristics of the resulting device were measured and evaluated in the same way as in Example 17. As the initial characteristics associated with the light emission, a green light emission with a maximum external quantum efficiency (E.Q.E.) of 6.7% was obtained. The device was subjected to a continuous operation test at a current density of 50 mA/cm². The time when the percentage of luminance degradation reached 5% (LT95) was measured to be 148 hours.

Examples 24 to 40 and Comparative Example 2

Organic light-emitting devices were produced in the same way as in Example 23, except that the compounds listed in Table 6 were used as appropriate. The characteristics of the resulting devices were measured and evaluated in the same way as in Example 23. Table 6 presents the measurement results.

TABLE 6

|  | HTL | EBL | Host | Assist | Light-emitting material | HBL | ETL | E.Q.E [%] | LT95 [h] | Emission color |
|---|---|---|---|---|---|---|---|---|---|---|
| Example 24 | HT3 | HT12 | EM11 | B-2 | GD6 | ET12 | ET2 | 6.8 | 155 | green |
| Example 25 | HT3 | HT11 | EM11 | B-14 | GD6 | ET12 | ET2 | 6.7 | 159 | green |
| Example 26 | HT3 | HT12 | EM10 | C-13 | GD7 | ET12 | ET2 | 6.8 | 154 | green |
| Example 27 | HT2 | HT11 | EM9 | D-12 | GD7 | ET12 | ET2 | 6.7 | 150 | green |
| Example 28 | HT2 | HT10 | EM10 | G-1 | GD6 | ET16 | ET5 | 6.8 | 128 | green |
| Example 29 | HT3 | HT11 | EM14 | E-15 | GD9 | ET12 | ET2 | 6.6 | 158 | green |
| Example 30 | HT3 | HT12 | EM11 | G-2 | GD1 | ET11 | ET2 | 6.3 | 113 | green |
| Example 31 | HT3 | HT12 | EM32 | B-2 | GD4 | ET11 | ET2 | 6.2 | 95 | green |
| Example 32 | HT2 | HT11 | EM11 | I-2 | RD1 | ET16 | ET7 | 5.5 | 178 | red |
| Example 33 | HT2 | HT12 | EM11 | I-15 | RD1 | ET12 | ET2 | 4.2 | 180 | red |
| Example 34 | HT3 | HT10 | EM9 | I-6 | RD1 | ET12 | ET2 | 5.3 | 185 | red |
| Example 35 | HT2 | HT12 | EM14 | I-4 | RD1 | ET11 | ET5 | 5.2 | 182 | red |
| Example 36 | HT3 | HT10 | EM9 | D-6 | RD1 | ET12 | ET2 | 5.1 | 154 | red |
| Example 37 | HT2 | HT12 | EM14 | G-11 | RD1 | ET11 | ET5 | 4.3 | 155 | red |
| Example 38 | HT3 | HT11 | EM11 | I-12 | RD2 | ET11 | ET2 | 5.3 | 125 | red |
| Example 39 | HT3 | HT12 | EM14 | I-4 | RD2 | ET12 | ET2 | 5.3 | 105 | red |
| Example 40 | HT3 | HT11 | EM9 | H-3 | RD2 | ET12 | ET2 | 4.0 | 110 | red |
| Comparative example 1 | HT3 | HT11 | EM11 | comparative compound 1 | GD9 | ET12 | ET2 | 4.3 | 70 | green |

As described in Table 6, the maximum external quantum efficiency (E.Q.E.) in Comparative example 2 was as low as 4.3%. The 5% degradation lifetime (LT95) in Comparative example 2 was 70 hours, indicating poor durability characteristics. The reason for the low efficiency is that the large difference between $S_1$ and $T_1$ of comparative compound 1 results in the absence of an emission component based on delayed fluorescence. In addition, the reason for this is presumably due to concentration quenching caused by molecular association because of the high molecular aspect ratio of comparative compound 1. The reason for the poor durability is presumably that comparative compound 1 is prone to molecular association, poor film properties, and crystallization due to the high molecular aspect ratio thereof.

In contrast, the devices containing the compounds according to embodiments of the present disclosure exhibited high efficiency and good durability characteristics. Each of the compounds according to embodiments of the present disclosure contains a carbonyl group-containing fused ring as a basic skeleton and an amino group as a substituent and thus has a small energy gap between $S_1$ and $T_1$ and a low molecular aspect ratio. Accordingly, it is thought that concentration quenching could be reduced to result in high-efficiency light emission based on delayed fluorescence. In addition, the presence of an amino group as a substituent that reduces the degree of molecular flatness in the basic skeleton having a high degree of flatness is thought to have resulted in a film having a low molecular aspect ratio and a high degree of amorphous nature, exhibiting good durability characteristics.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2020-183750 filed Nov. 2, 2020, which is hereby incorporated by reference herein in its entirety.

What is claimed is:

1. An organic compound represented by formula [1] or [2]:

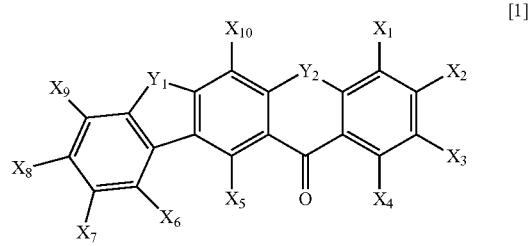

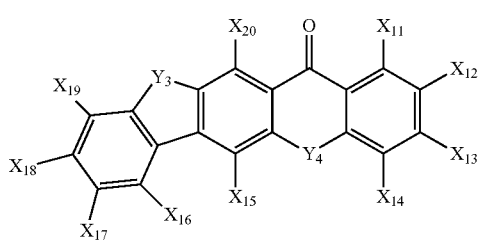

where in formula [1] or [2],
$X_1$ to $X_{20}$ are each independently selected from a hydrogen atom, a halogen atom, a substituted or unsubstituted alkyl group, a substituted or unsubstituted alkoxy group, a substituted or unsubstituted amino group, a substituted or unsubstituted aromatic hydrocarbon group, a substituted or unsubstituted heterocyclic group, a substituted or unsubstituted aryloxy group, a substituted or unsubstituted heteroaryloxy group, a silyl group, and a cyano group,
wherein at least one of $X_1$ to $X_{10}$ and at least one of $X_{11}$ to $X_{20}$ are substituted or unsubstituted amino groups or are groups containing substituted or unsubstituted amino groups, and groups bonded to nitrogen atoms of the substituted or unsubstituted amino groups are optionally taken together to form a ring structure;
$Y_1$ and $Y_3$ are each oxygen, sulfur, selenium, tellurium, a carbonyl group, or a $CR_1R_2$ group,
wherein $R_1$ and $R_2$ are each independently selected from a hydrogen atom, a halogen atom, a substituted or unsubstituted alkyl group, a substituted or unsubstituted alkoxy group, a substituted or unsubstituted amino group, a substituted or unsubstituted aromatic hydrocarbon group, a substituted or unsubstituted heterocyclic group, a substituted or unsubstituted aryloxy group, a substituted or unsubstituted heteroaryloxy group, a silyl group, and a cyano group;
$Y_2$ and $Y_4$ are each oxygen, sulfur, selenium, or tellurium, and
$Y_1$ and $Y_2$ are either same as each other or different from each other, and $Y_3$ and $Y_4$ are either same as each other or different from each other.

2. The organic compound according to claim 1, wherein the organic compound has a molecular aspect ratio of 5.0 or less.

3. The organic compound according to claim 1, wherein at least one of $X_6$ to $X_9$ and at least one of $X_{16}$ to $X_{19}$ are each a substituted or unsubstituted amino group or are each a group containing a substituted or unsubstituted amino group.

4. The organic compound according to claim 3, wherein at least one of $X_6$ to $X_9$ and at least one of $X_{16}$ to $X_{19}$ are each a substituted or unsubstituted amino group.

5. The organic compound according to claim 1, wherein at least one of $X_6$ to $X_9$ and at least one of $X_{16}$ to $X_{19}$ are each an amino group having any of structures:

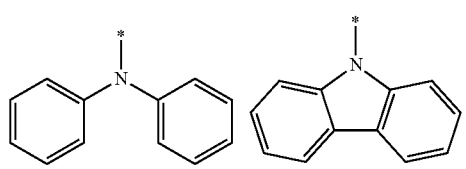

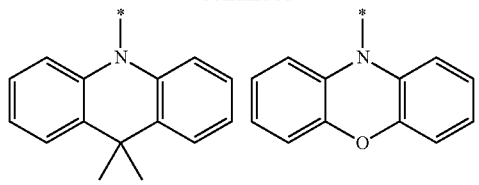

117
-continued
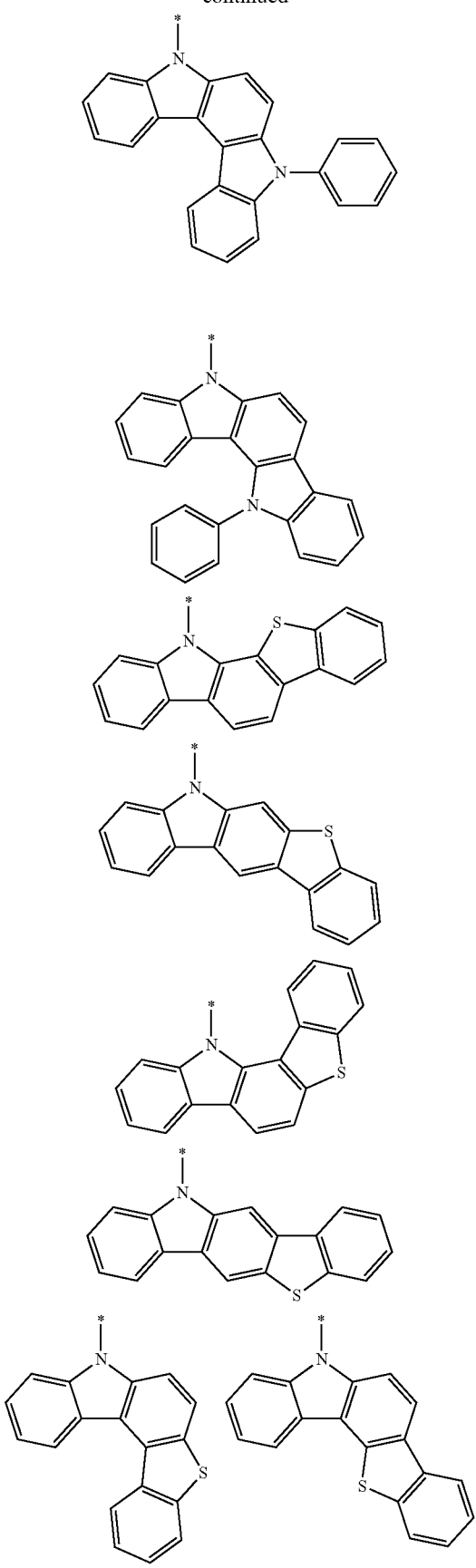
118
-continued
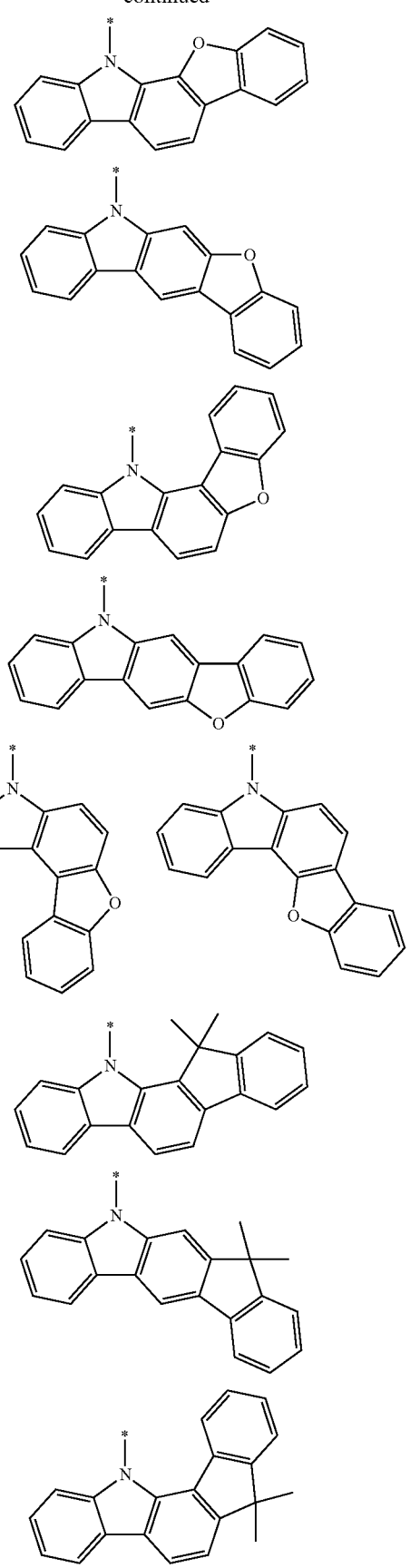

-continued

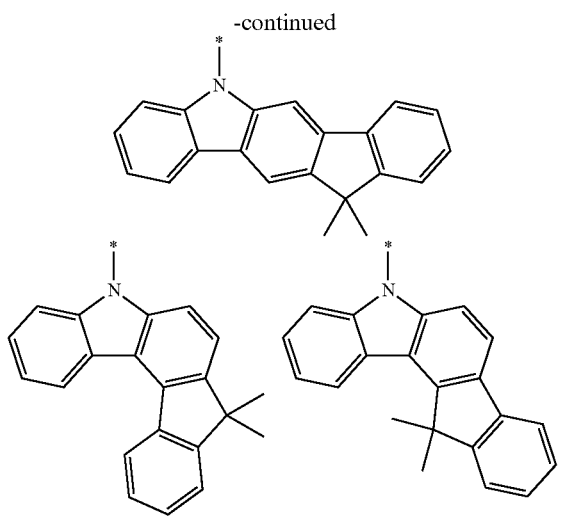

where each * represents a binding position.

6. The organic compound according to claim 1, wherein $Y_1$ and $Y_3$ are each oxygen, sulfur, or a $CR_1R_2$ group, and $Y_2$ and $Y_4$ are each oxygen or sulfur.

7. The organic compound according to claim 1, wherein $X_1$ to $X_4$ and $X_{11}$ to $X_{14}$ are each a hydrogen atom, a substituted or unsubstituted alkyl group, a phenyl group, a biphenyl group, a naphthyl group, a pyridyl group, a pyrazinyl group, a triazinyl group, fluorine, or a cyano group.

8. An organic light-emitting device, comprising:
an anode;
a cathode; and
at least one organic compound layer disposed between the anode and the cathode,
wherein at least one layer of the at least one organic compound layer contains the organic compound according to claim 1.

9. The organic light-emitting device according to claim 8, wherein the layer containing the organic compound is a light-emitting layer.

10. The organic light-emitting device according to claim 9, wherein the light-emitting layer further contains a host material.

11. The organic light-emitting device according to claim 10, wherein the host material is a hydrocarbon compound.

12. The organic light-emitting device according to claim 10, wherein the light-emitting layer further contains a light-emitting material.

13. The organic light-emitting device according to claim 12, wherein the light-emitting material is a hydrocarbon compound.

14. The organic light-emitting device according to claim 9, wherein the light-emitting layer emits green light or red light.

15. A display apparatus, comprising:
multiple pixels, at least one of the multiple pixels including:
the organic light-emitting device according to claim 8; and
a transistor connected to the organic light-emitting device.

16. A photoelectric conversion apparatus, comprising:
an optical unit including multiple lenses;
an image pickup device that receives light passing through the optical unit; and
a display unit that displays an image captured by the image pickup device,
wherein the display unit includes the organic light-emitting device according to claim 8.

17. An electronic apparatus, comprising:
a display unit including the organic light-emitting device according to claim 8;
a housing provided with the display unit; and
a communication unit being disposed in the housing and communicating with an outside.

18. A lighting device, comprising:
a light source including the organic light-emitting device according to claim 8; and
a light diffusion unit or an optical filter that transmits light emitted from the light source.

19. A moving object, comprising:
a lighting unit including the organic light-emitting device according to claim 8; and
a body provided with the lighting unit.

20. An exposure light source for an electrophotographic image-forming apparatus, comprising:
the organic light-emitting device according to claim 8.

* * * * *